(12) United States Patent
Hahn et al.

(10) Patent No.: US 7,592,188 B2
(45) Date of Patent: Sep. 22, 2009

(54) LIVE CELL BIOSENSORS

(75) Inventors: Klaus M. Hahn, Chapel Hill, NC (US); Alexei Toutchkine, Arlington, MA (US)

(73) Assignee: The Scripps Research Institute, La Jolla, CA (US)

( * ) Notice: Subject to any disclaimer, the term of this patent is extended or adjusted under 35 U.S.C. 154(b) by 66 days.

(21) Appl. No.: 11/079,907

(22) Filed: Mar. 14, 2005

(65) Prior Publication Data

US 2006/0029946 A1 Feb. 9, 2006

Related U.S. Application Data

(60) Provisional application No. 60/552,663, filed on Mar. 12, 2004.

(51) Int. Cl.
| | |
|---|---|
| G01N 21/91 | (2006.01) |
| G01N 21/64 | (2006.01) |
| G01N 33/533 | (2006.01) |
| C09B 69/00 | (2006.01) |
| A61K 38/00 | (2006.01) |

(52) U.S. Cl. .................. 436/800; 435/172; 435/546; 514/2; 106/31.27; 106/31.15

(58) Field of Classification Search ............... 435/125, 435/70.2, 548
See application file for complete search history.

(56) References Cited

U.S. PATENT DOCUMENTS

| | | | |
|---|---|---|---|
| 4,036,945 | A | 7/1977 | Haber |
| 4,331,647 | A | 5/1982 | Goldenberg |
| 4,816,567 | A | 3/1989 | Cabilly et al. |
| 5,733,743 | A | 3/1998 | Johnson et al. |
| 5,750,373 | A | 5/1998 | Garrard et al. |
| 5,814,468 | A * | 9/1998 | Siiman et al. ............... 435/7.21 |
| 5,880,270 | A | 3/1999 | Berninger et al. |
| 6,290,957 | B1 | 9/2001 | Lowman et al. |
| 6,649,421 | B1 * | 11/2003 | Eigenthaler et al. ......... 436/548 |
| 7,070,943 | B2 * | 7/2006 | Darzynkiewicz et al. ..... 435/7.2 |
| 2002/0094534 | A1 | 7/2002 | Greene et al. |

FOREIGN PATENT DOCUMENTS

| | | |
|---|---|---|
| EP | 0949269 A1 | 10/1999 |
| WO | WO-02/08245 A2 | 1/2002 |
| WO | WO-02/28890 A1 | 4/2002 |
| WO | WO-03003666 A1 | 1/2003 |
| WO | WO-03/033666 A2 | 4/2003 |
| WO | WO-2005/088308 A3 | 9/2005 |

OTHER PUBLICATIONS

Bart et al. (1997) Environmental immunoassay for the explosive RDX using a fluorescent dye-labeled antigen and the continuous-flow immunosensor, vols. 38-39, pp. 411-418.*
Brown et al. (1984)The stimulation of pp60v-src kinase activity by vanadate in intact cells accompanies a new phosphorylation state of the enzyme. J. Biol. Chem. vol. 259, No. 15, pp. 9580-9586.*
Tansey et al. (1994) Ca(2+)-dependent phosphorylation of myosin light chain kinase decreases the Ca2+ sensitivity of light chain phosphorylation within smooth muscle cells. J. Biol. Chem. vol. 269, No. 13, pp. 9912-9920.*
Marvin et al. (1998) Engineering Biosensors by Introducing Fluorescent Allosteric Signal Transducers: Construction of a Novel Glucose Sensor, J. Am. Chem. Soc. vol. 120, pp. 7-11.*
Gok et al. (2004) Binding of fluorescein isothiocyanate to insulin: a fluorimetric labeling study. J. Fluoresc. vol. 14, No. 2, pp. 203-206.*
Fluorescent Dyes (2006, updated) www.ab-direct.com. p. 1.*
HIV type, groups and subtypes (2007, update) http://wwww.avert.org/hivtypes.htm., pp. 1-5.*
Prendergast et al. (1983) Synthesis, spectral properties, and use of 6-acryloyl-2-dimethylaminonaphthalene (Acrylodan). A thiol-selective, polarity-sensitive fluorescent probe. J. Bio.1Chem. vol. 258, No. 12, pp. 7541-7544.*
Batard et al. (2002) Use of phycoerythrin and allophycocyanin for fluorescence resonance energy transfer analyzed by flow cytometry: advantages and limitations, Cytometry, vol. 48, No. 2, pp. 97-105.*
Garofalo et al. (2002) Ganglioside GM3 activates ERKs in human lymphocytic cells, J. Lipid Res, vol. 43, No. 6, pp. 971-978.*
Wilder et al. (2006) Recognition of the tumor suppressor protein p53 and other protein targets by the calcium-binding protein S100B, Biochim. Biophys. Acta., vol. 1763, No. 11, pp. 1284-1297.*
Cheng et al. (2007) Separation distance dependent fluorescence enhancement of fluorescein isothiocyanate by silver nanoparticles, Chem. Commun. (Camb), vol. 21, No. 3, pp. 21, pp. 248-250.*
Wilk et al. (1999) Evolution of a light-harvesting protein by addition of new subunits and rearrangement of conserved elements: crystal structure of a cryptophyte phycoerythrin at 1.63-A resolution, Proc. Natl. Acad. Sci. U S A., vol. 96, No. 16, pp. 8901-8906.*
Czurylo et al. (1997) Does calponin interact with caldesmon, J. Biol. Chem., vol. 272, No. 51, pp. 32067-32070.*
Ludeman et al. (2001) Structure of a serpin-enzyme complex probed by cysteine substitutions and fluorescence spectroscopy, Biophys. J., vol. 80, No. 1, pp. 491-497.*

(Continued)

*Primary Examiner*—Jon P Weber
*Assistant Examiner*—Samuel W Liu
(74) *Attorney, Agent, or Firm*—Schwegman, Lundberg & Woessner, P.A.

(57) ABSTRACT

The invention provides dyes, biosensors, and methods for using the dyes and biosensors to detect selected target molecules. The biosensors have a binding domain and a dye, or a dye which is attached directly to the target of interest. Binding domains contemplated by the invention include biomolecules or fragments of biomolecules that interact with target molecules of interest and can be specific to a given conformational state or covalent modification of the molecule (e.g. phosphorylation). In one embodiment, the binding domain of a biosensor is a single chain variable fragment (scFv) with a dye of the invention linked to a CDR3 region. The invention also provides environmentally sensitive dyes useful for detecting changes in the binding, conformational change, or posttranslational modification of the selected target.

56 Claims, 22 Drawing Sheets
(3 of 22 Drawing Sheet(s) Filed in Color)

OTHER PUBLICATIONS

Olympus (2007, updated) "Fluorochrome data tables", http://www.olympusmicro.com/primer/techniques/fluorescence/fluorotable2.html, pp. 1-6.*
Pierce (2007, updated) "Sulfo-SMCC", http://www.piercenet.com/Objects/View.cfm?type=ProductFamily&ID=02030378&Format=Print, p. 1.*
International Search Report for corresponding PCT Application No. PCT/US2005/008426 (Nov. 4, 2005), 6 pgs.
Abdul-Manan, Norzehan, et al., "Structure of Cdc42 in Complex With the GTPase-Binding Domain of the 'Wiskott-Aldrich Syndrome' Protein," *Nature*, 399(6734), (1999),379-383.
Alzari, P. M., et al., "Three-Dimensional Structure of Antibodies", *Annual Review of Immunology*, 6, (1988),555-580.
Bebbington, C. R., et al., "High-Level Expression of a Recombinant Antibody From Myeloma Cells Using a Glutamine Synthetase Gene as an Amplifiable Selectable Marker", *Bio/Technology*, 10, (Feb. 1992), 169-175.
Benniston, Andrew C., et al., "Spin-Orbital Coupling Effects on the Photophysical Properties and Photocytotoxicity of Merocyanine Dyes", *J. Chem. Soc., Faraday Trans.*, 93(15), (1997),2491-2501.
Berridge, Michael J., "Calcium Oscillations", *The Journal of Biological Chemistry*, 265(17), (1990),9583-9586.
Binley, James M., et al., "Redox-Triggered Infection by Disulfide-Shackled Human Immunodeficiency Virus Type I Pseudovirions", *Journal of Virology*, 77(10), (May 2003),5678-5684.
Bishop, Anne L., et al., "Rho GTPases and their effector proteins", *Biochem. J.*, 348(Pt. 2), (2000),241-255.
Boder, Eric T., et al., "Directed Evolution of Antibody Fragments With Monovalent Femtomolar Antigen-Binding Affinity", *Proc. Natl. Soc. Sci. USA*, 97(20), (Sep. 26, 2000),10701-10705.
Bright, G. R. et al., "Fluorescence Ratio Imaging Microscopy", *Methods in Cell Biology*, 30, (1989),157-192.
Burton, Dennis R., et al., "Human Antibodies From Combinatorial Libraries", *Advances in Immunology*, 57, (1994),191-280.
Chamberlain, Chester, et al., "Watching Proteins in the Wild: Fluorescence Methods to Study Protein Dynamics in Living Cells", *Traffic*, 1(10), (Oct. 2000),755-762.
Chiswell, David J., et al., "Phage Antibodies: Will New 'Coliclonal' Antibodies Replace Monoclonal Antibodies?", *Trends in Biotechnology*, 10, (1992),80-84.
Clackson, Tim, et al., "Making Antibody Fragments Using Phage Display Libraries", *Nature*, 352(6336), (Aug. 15, 1991),624-628.
Collis, Abigail V., et al., "Analysis of the Antigen Combining Site: Correlations Between Length and Sequence Composition of the Hypervariable Loops and the Nature of an Antigen", *Journal of Molecular Biology*, 325, (2003),337-354.
Collman, James P., et al., "Metal Ion Facilitation of Atom-Transfer Oxidation-Reduction Reactions", *Journal of the American Chemical Society*, 89(18), (Aug. 30, 1967),4809-4811.
Correa, Paul E., et al., "Selective Autoxidation of Electron-Rich Substrates Under Elevated Oxygen Pressures", *J. Org. Chem.*, 53, (1988),1695-1702.
Cunningham, Brian C., et al., "Production of an Atrial Natriuretic Peptide Variant That is Specific for Type A Receptor", *The EMBO Journal*, 13(11), (1994),2508-2515.
Cwirla, Steven E., et al.,"Peptides on phage: a vast library of peptides for identifying ligands", *Proc Natl Acad Sci U S A*, 87(16), (Aug. 1990),6378-6382.
Del Pozo, Miguel A., et al., "Integrins regulate GTP-Rac localized effector interactions through dissociation of Rho-GDI", *Nature Cell Biology*, 4(3), (Mar. 2002),232-9.
Demas, J. N., et al., "The Measurement of Photoluminescence Quantum Yields. A Review", *The Journal of Physical Chemistry*, 75(8), (Apr. 15, 1971),991-1024.
Der Maur, Adrian A., et al., "Direct in Vivo Screening of Intrabody Libraries Constructed on a Highly Stable Single-Chain Framework", *The Journal of Biological Chemistry*, 277(47), (Nov. 22, 2002),45075-45085.
Etienne-Manneville, Sandrine, "Cdc42—The Centre of Polarity", *Journal of Cell Science*, 117(8), (2004),1291-1300.
Feldhaus, Michael J., et al., "Flow-cytometric isolation of human antibodies from a nonimmune *Saccharomyces cerevisiae* surface display library", *Nature Biotechnology*, 21(2), (Feb. 2003),163-170.
Flanagan, James H., et al., "Functionalized Tricarbocyanine Dyes as Near-Infrared Fluorescent Probes for Biomolecules", *Bioconjugate Chem.*, 8(5), (1997),751-756.
Foote, Christopher S., et al., "Chemistry of Singlet Oxygen. XIV. A Reactive Intermediate in Sulfide Photooxidation", *Journal of the American Chemical Soceity*, 93(15), (Jul. 28, 1971),3795-3796.
Gardiner, Elisabeth M., et al., "Spatial and Temporal Analysis of Rac Activation During Live Neutrophil Chemotaxis", *Current Biology*, 12(23), (Dec. 10, 2002),2029-2034.
Glogauer, M., et al., "Introduction of Large Molecules Into Viable Fibroblasts by Electroporation: Optimization of Loading and Identification of Labeled Cellular Compartments", *Experimental Cell Research*, 200(2), (1992),227-234.
Hahn, Klaus M., et al., "A Calcium-Sensitive Fluorescent Alalog of Calmodulin Based on a Novel Calmodulin-Binding Fluorophore", *Journal of Biological Chemistry*, 265(33), (Jan 29, 1990),20335-20345.
Hahn, Klaus, et al., "Live-Cell Fluorescent Biosensors for Activated Signaling Proteins", *Current Opinion in Cell Biology*, 14, (2002),167-172.
Hanes, Jozef, et al., "In vitro Selection and Evolution of Functional Proteins by Using Ribosome Display", *Proc Natl Acadd Sci USA*, 94(10), (May 13, 1997),4937-4942.
Hanes, Jozef , et al., "Picomolar Affinity Antibodies From a Fully Synthetic Naive Library Selected and Evolved by Ribosome Display", *Nature Biotechnology*, 18(12), (Dec. 2000),1287-1291.
Hawkins, Robert E., "Selection of Phage Antibodies by Binding Affinity. Mimicking Affinity Maturation.", *Journal of Molecular Biology*. 226(3), (1992)889-896.
Higgs, Henry N., et al., "Activation by Cdc42 and $PIP_2$ of Wiskott-Aldrich Syndrome Protein (WASp) Stimulates Actin Nucleation by Arp2/3 Complex", *The Journal of Cell Biology*, 150(6), (Sep. 18, 2000),1311-1320.
Hoffman, Gregory R., et al., "Structure of the Rho family GTP-binding protein Cdc42 in complex with the multifunctional regulator RhoGDI", *Cell*, 100(3), (Feb. 4, 2000),345-356.
Holmes, Margaret A., et al., "Structural Consequences of Humanizing an Antibody.", *Journal of Immunology* , 158(5), (1997),2192-2201.
Hoogenboom, Hennie R., et al., "Building Antibodies From Their Genes", *Immunological Reviews*, 130, (Dec. 1992),41-68.
Ischenko, A. A., "Structure and Spectral-Luminescent Properties of Polymethine Dyes", *Russian Chemical Reviews*, 60(8), (1991),865-884.
Itoh, Reina E., et al., "Activation of Rac and Cdc42 Video Imaged by Fluorescent Resonance Energy Transfer-Based Single-Molecule Probes in the Membrane of Living Cells", *Molecular and Cellular Biology*, 22(18), (2002),6582-6591.
Iwatani, Shintaro, et al., "Mechanical and Chemical Properties of Cysteine-Modified Kinesin Molecules", *Biochemistry*, 38(32), (Aug. 10, 1999), 10318-10323.
Jobbing, Stephen A., et al., "Immunomodulation of Enzyme Function in Plants by Single-Domain Antibody Fragments", *Nature Biotechnology*, 21, (Jan. 2003),77-80.
Johnson, George, et al., "Kabat Database and its Applications: 30 Years After the First Variability Plot", *Nucleic Acids Research*, 28(1), (2000),214-218.
Jones, T. A., et al., "[10] Electron-Density Map Interpretation", *Methods in Enzymology*, 277(Part B), (1987),173-208.
Jones, Peter T., et al., "Replacing the Complementarity-Determining Regions in a Human Antibody With Those From a Mouse", *Nature*, 321(6069), (May 29, 1986),522-525.
Kanony, Claire, et al., "Photobleaching of Asymmetric Cyanines Used for Fluorescence Imaging of Single DNA Molecules", *Journal of the American Chemical Society*, 123, (2001),7985-7995.
Kim, Annette S., et al., "Autoinhibition and Activation Mechanisms of the Wiskott-Aldrich Syndrome protein", *Nature*, 404(6774), (Mar. 9, 2000), 151-158.

Knappik, Achim, et al., "Fully Synthetic Human Combinatorial Antibody Libraries (HuCAL) Based on Modular Consensus Frameworks and CDRs Randomized With Trinucelotides", *Journal of Molecular Biology*, 296, (2000), 57-86.

Knaus, Ulla G., "Purification and Characterization of Rac 2. A Cytosolic GTP-Binding Protein that Regulates Human Neutrophil NADPH Oxidase", *Journal of Biological Chemistry*, 267(33), (Nov. 25, 1992),23575-23582.

Köhler, G., et al., "Continuous Cultures of Fused Cells Secreting Antibody of Predefined Specificity", *Nature*, 256(5517), (Aug. 7, 1975),495-497.

Kozma, Robert, et al., "The Ras-Related Protein Cdc42Hs and Bradykinin Promote Formation of Peripheral Actin Microspikes and Filopodia in Swiss 3T3 Fibroblasts", *Molecular and Cellular Biology*, 15(4), (Apr. 1995),1942-1952.

Kraynov, Vadim S., et al., "Localized Rac Activation Dynamics Visualized in Living Cells", *Science*, 290(5490), (Oct. 13, 2000),333-336.

Kwong, Peter D., et al., "Structuree of an HIV gp120 Envelope Glycoprotein in Complex With the CD4 Receptor and a Neutralizing Human Antibody", *Nature*, 393, (Jun. 18, 1998),648-659.

Larrick, James W., et al., "PCR Amplification of Antibody Genes", *Methods: a Companion to Methods in Enzymology*, 2(2), (1991),106-110.

Lednev, I. K., et al., "A Raman Spectroscopic Study of Photochromic Benzothiazolium Dyes", *Spectrochimica Acta*, 49A(8), (1993),1055-1063.

Lippincott-Schwartz, Jennifer, et al., "Development and Use of Fluorescent Protein Markers in Living Cells", *Science*, 300, (Apr. 4, 2003),87-91.

Lippincott-Schwartz, Jennifer, et al., "Studying Protein Dynamics in Living Cells", *Nature Reviews*, 2(6), (Jun. 2001),444-456.

Lowman, Henry B., et al., "Selecting High-Affinity Binding Proteins by Monovalent Phage Display", *Biochemistry*, 30(45), (Nov. 12, 1991),10832-10838.

Lu, Liangde, et al., "Exciton and Charge-Transfer Interactions in Nonconjugated Merocyanine Dye Dimers: Novel Solvatochromic Behavoir for Tethered Bichromophores and Excimers", *Journal of the American Chemical Society*, 121, (1999),8146-8156.

Machesky, Laura M., et al., "Signaling to Actin Dynamics", *Journal of Cell Biology*, 146(2), (Jul. 26, 1999),267-272.

Mandel, Debabrata, et al., "Photophysical Processes of Merocyanine 540 in Solutions and in Organized Metals", *J. Phys. Chem. A*, 103, (1999),8156-8159.

Manning, W. B., et al., "Synthesis of 6-Aminobenzothiazoles from p-Benzoquinone Imine Derivatives", *Synthesis*, 5, (May 1978),363.

Marks, James D., "By-Passing Immunization. Human Antibodies From V-Gene Libraries Displayed on Phage.", *Journal of Molecular Biology*, 222(3), (1991),581-597.

McNeil, Paul L., et al., "A Method for Incorporating Macromolecules Into Adherent Cells", *The Journal of Cell Biology*, 98(4), (Apr. 1984),1556-1564.

McNeil, Paul L., et al., "Glass Beads Load Macromolecules Into Living Cells", *Journal of Cell Science*, 88(Part 5), (Dec. 1987),669-678.

Miller, Peter J., et al., "Cdc42p GTPase Is Involved in Controlling Polarized Cell Growth in *Schizosaccharomyces pombe*", *Molecular and Cellular Biology*, 14(2), (Feb. 1994),1075-1083.

Mochizuki, Naoki, et al., "Spatio-Temporal Images of Growth-Factor-Induced Activation of Ras and Rap1", *Nature*, 411, (Jun. 28, 2001),1065-1068.

Morrison, Sherie L., "Chimeric Human Antibody Molecules: Mouse Antigen-Binding Domains With Human Constant Region Domains", *Proc. Natl. Acad. Sci. USA*, 81(21), (Nov. 1984),6851-6855.

Moulard, Maxime, et al., "Broadly Cross-Reactive HIV-1-Neutralizing Human Monoclonal Fab Selected for Binding to gp120-CD4-CCR5 Complexes", *Proc. Natl. Acad. Sci. USA*, 99(10), (May 14, 2002),6913-6918.

Mujumdar, Ratnakar B., et al., "Cyanine Dye Labeling Reagents Containing Isothiocyanate Groups", *Cytometry*, 10(1), (1989),11-19.

Nakahara, Hiroo, et al., "Two-Dimensional Arrangement of Chromophores in *J* Aggregates of Long-Chain Merocyanines and Its Effect on Energy Transfer in Monolayer Systems", *J. Phys. Chem.*, 90, (1986)6144-6148.

Nalbant, Perihan, et al., "Activation of Endogenous Cdc42 Visualized in Living Cells", *Science*, 305, (Sep. 10, 2004),1615-1619.

Narayanan, Narasimhachari, et al., "A New Method for the Synthesis of Heptamethine Cyanine Dyes: Synthesis of New Near-Infrared Fluorescent Labels", *J. Org. Chem.*, 60, (1995),2391-2395.

Nizak, Clement, et al., "Recombinant Antibodies to the Small GTPase Rab6 as Conformation Sensors", *Science*, 300(5621), (May 9, 2003),984-987.

Nobes, C. D., "Rho, rac and cdc42 GTPases: Regulators of Actin Structures, Cell Adhesion and Motility", *Biochemical Society Transations*, 23(3), (Aug. 1995),456-459.

Okada, Craig Y., et al., "Introduction of Macromolecules Into Cultured Mammalian Cells by Osmotic Lysis of Pinocytic Vesicles", *Cell*, 29(1), (May 1982),33-41.

Onganer, Yavuz, et al., "Dynamical Solvation Effects on the Cis-Trans Isomerization Reaction: Photoisomerization of Merocyanine 540 in Polar Solvents", *J. Phys. Chem.*, 97, (1993),2344-2354.

Pack, Peter, et al., "Improved Bivalent Miniantibodies, With Identical Avidity as Whole Antibodies, Produced by High Cell Density Fermentation of *Escherichia coli*", *Bio/Technology*. 11(11), (Nov. 1993),1271-1277.

Park, Ro D., et al., "Hypertonic Sucrose Inhibition of Endocytic Transport Suggests Multiple Early Endocytic Compartments", *Journal of Cellular Physiology*, 135(3), (1988),443-450.

Parmley, Stephen F., et al., "Antibody-Selectable Filamentous fd Phage Vectors: Affinity Purification of Target Genes", *Gene*, 73(2), (Dec. 1988),305-318.

Pestic-Dragovich, Lidija, et al., "A Myosin I Isoform in the Nucleus", *Science*, 290(5490), (Oct. 13, 2000),337-341.

Presta, Leonard G., "Antibody Engineering", *Current Opinion in Structural Biology*, 2(4), (1992),593-596.

Proba, Karl, et al., "Antibody scFv Fragments Without Disulfide Bonds Made by Molecular Evolution", *Journal of Molecular Biology*, 275, (1998),245-253.

Rader, Christoph, et al., "Phage Display of Combinatorial Antibody Libraries", *Current Opinion in Biotechnology*, 8(4), (Aug. 1997),503-508.

Regitz, Manfred, "Reaktionen aktiver Methylenverbindungen mit Azidne, V—Uber ein a-Diazo-b-keto-sulfon", *Chemische Berichte*, 98(1), (1965),36-45.

Renard, M., et al., "Deriving Topological Constraints From Functional Data for the Design of Reagentless Fluorescent Immunosensors", *J. Mol. Biol.*, 326(1), (2003),167-175.

Renard, Martial, et al., "Knowledge-Based Design of Reagentless Fluorescent Biosensors From Recombinant Antibodies", *J. Mol. Biol.*, 318(2), (2002),429-442.

Riechmann, Lutz, et al., "Reshaping Human Antibodies for Therapy.", *Nature*, 332(6162), (Mar. 24, 1988),323-327.

Russell, Stephen J., "Retroviral Vectors Displaying Functional Antibody Fragments", *Nucleic Acids Research*, 21(5), (1993),1081-1085.

Saphire, Erica O., et al., "Crystal Structure of a Neutralizing Human IgC Against HIV-1: A Template for Vaccine Design", *Science*, 293, (Aug. 10, 2001),1155-1159.

Schaffitzel, Christine, et al., "Ribosome Display: An in vitro Method for Selection and Evolution of Antibodies From Libraries", *Journal of Immunological Methods*, 231, (1999),119-135.

Schneckenburger, H., et al., "Laser-assisted optoporation of single cells", *Journal of Biomedical Optics*, 7(3), (Jul. 2002),410-416.

Scott, Jamie K., "Discovering Peptide Ligands Using Epitope Libraries", *Trends in Biochemical Sciences*, 17(7), (Jul. 1992),241-245.

Seth; Abhinav, et al., "Rational Design of Genetically Encoded Fluorescence Resonance Energy Transfer-Based Sensors of Cellular Cdc42 Signalling", *Biochemistry*, 42(14), (Apr. 15, 2003),3997-4008.

Sloan, David J., et al., "Structure-Based Engineering of Environmentally Sensitive Flurophores for Monitoring Protein-Protein Interactions", *Protein Engineering*, 11(9), (1998),819-823.

Soper, Steven A., et al., "Steady-State and Picosecond Laser Fluorescence Studies of Nonradiative Pathways in Tricarbocyanin Dyes: Implications to the Design of Near-IR Fluorochromes With High Fluorescence Efficiencies", *Journal of the American Chemical Society*, 116, (1994),3744-3752.

Soughayer, Joseph S., et al., "Characterization of Cellular Optoporation With Distance", *Analytical Chemistry*, 72(6), (Mar. 15, 2000),1342-1347.

Subauste, M. C., et al., "A Catalytic Antibody Produces Fluorescent Tracers of Gap Junction Communication in Living Cells", *The Journal of Biological Chemistry*, 276(52), (2001),49164-49168.

Tanakka, Tomoyuki, et al., "*De novo* Production of Diverse Intracellular Antibody Libraries", *Nucleic Acids Research*, 31(5)(e23), (2003),10 pgs.

Teruel, Mary N., et al., "A Versatile Microporation Technique for the Transfection of Cultured CNS Neurons", *Journal of Neuroscience Methods*, 93, (1999),37-48.

Teruel, Mary N., et al., "Parallel Single-Cell Monitoring of Receptor-Triggered Membrane Translocation of a Calcium-Sensing Protein Module", *Science*, 295, (Mar. 8, 2002),1910-1912.

Ting, Alice Y., et al., "Genetically Encoded Fluorescent Reporters of Protein Tyrosine Kinase Activities of Living Cells", *Proc. Natl. Acad. Sci. USA*, 98(26), (Dec. 18, 2001),15003-15008.

Toomre, Derek, et al., "Lighting Up the Cell Surface With Evanescent Wave Microscopy", *Trends in Cell Biology*, 11(7), (Jul. 2001),298-303.

Torchilin, Vladimir P., et al., "Cell Transfection in vitro and in vivo With Nontoxic TAT Peptide-Liposome-DNA Complexes", *Proc. Natl. Acad. Sci. USA*, 100(4), (Feb. 18, 2003),1972-1977.

Toutchkine, Alexei, et al., "Solvent-Sensitive Dyes to Report Protein Conformational Changes in Living Cells", *Journal of the American Chemical Society*, 125(14), (Apr. 4, 2003),4132-4145.

Trinkaus-Randall, V., et al., "Role of Calcium and Calmodulin in Hemidesmosome Formation In Vitro", *The Journal of Cell Biology*, 98, (Apr. 1984),1565-1571.

Tse, Eric, et al., "Intracellular Antibody-Caspase-Mediated Cell Killing: An Approach for Application in Cancer Therapy", *Proc. Natl. Acad. Sci. USA*, 97(22), (Oct. 24, 2000),12266-12271.

Turro, Nicholas J., "The Role of Intersystem Crossing Steps in Singlet Oxygen Chemistry and Photo-Oxidations", *Tetrahedron*, 41(11), (1985),2089-2098.

Valdes-Aguilera, Oscar, et al., "Aggregation Phenomena in Xanthene Dyes", *Acc. Chem. Res.*, 22, (1989),171-177.

Vaswani, Surender K., et al., "Humanized Antibodies as Potential Therapeutic Drugs", *Annals of Allergy, Asthma, & Immunology*. 81(2), (1998),105-119.

Verveer, Peter J., et al., "Quantitative Imaging of Lateral ErbB1 Receptor Signal Propagation in the Plasma Membrane", *Science*, 290(5496), (2000),1567-1570.

Vignal, Emmanuel, et al., "Characterization of TCL, a New GTPase of the Pho Family Related to TC10 and Cdc42", *The Journal of Biological Chemistry*, 275(46), (2000),36457-36464.

Visintin, Michela, et al., "The Intracelluar Antibody Capture Technology (IACT): Towards a Consensus Sequence for Intracellular Antibodies", *Journal of Molecular Biology*, 317, (2002),73-83.

Watanabe, Yasumasa, et al., "Persulfoxide and Thiadioxirane Intermediates in the Reaction of Sulfides and Singlet Oxygen", *Journal of American Chemical Society*, 113, (1991),2677-2682.

Whitlow, Marc, et al., "Single-Chain Fv Proteins and Their Fusion Proteins", *Methods: a Companion to Methods in Enzymology*, 2(2), (1991),97-105.

Williams, David A., et al., "Calcium Gradients in Single Smooth Muscle Cells Revealed by the Digital Imaging Microscope Using Fura-2", *Nature*, 318(6046), (Dec. 12, 1985),558-561.

Winter, Greg, et al., "Making Antibodies by Phage Display Technology", *Annual Review of Immunology*, 12, (1994),433-455.

Wouters, Fred S., et al., "Imaging Biochemistry Inside Cells", *Trends in Cell Biology*, 11(5), (May 2001),203-211.

Würthner, Frank, et al., "Dipolar Dye Aggregates: A Problem for Nonlinear Optics, but a Chance for Supramolecular Chemistry", *Angew. Chem. Int. Ed.*, 39(11), (2000),1978-1981.

Yang, Yonghui, et al., "HIV-1 TAT-Mediated Protein Transduction and Subcellular Localization Using Novel Expression Vectors", *FEBS Letters*, 532, (2002),36-44.

Zaccolo, Manuela, et al., "A Genetically Encoded, Fluorescent Indicator for Cyclic AMP in Living Cells", *Nature Cell Biology*, 2(1), (Jan. 2000),25-29.

Zelphati, Olivier et al., "Intracellular Delivery of Proteins With a New Lipid-Mediated Delivery System", *The Journal of Biological Chemistry*1, 276(37), (2001),35103-35110.

Zhang, Jin, et al., "Creating New Fluorescent Probes for Cell Biology", *Nature Reviews*, 3(12), (Dec. 2002),906-918.

Zhang, Jin, et al., "Genetically Encoded Reporters of Protein Kinase A Activity Reveal Impact of Substrate Testing", *Proc. Natl. Acad. Sci. USA*, 98(26), (Dec. 18, 2001),14997-15002.

Zombeck, Alan, et al., "Novel Catalytic Oxidations of Terminal Olefins by Cobalt(II)-Schiff Base Complexes", *Journal of the American Chemical Society*, 104, (1982),6782-6784.

Chamberlain, K. M., et al., "Watching Proteins in the Wild: Fluorescence Methods to Study Protein Dynamics in Living Cells", *Traffic*, 1(10), (Oct. 2000),755-762.

Hahn, K. M., et al., "A calcium-sensitive fluorescent analog of calmodulin based on a novel calmodulin-binding fluorophore,", *J. Biol. Chem.*, 265(33), (Nov. 25, 1990),20335-45.

Machesky, L. M., et al., "Signaling to actin dynamics", *J Cell Biol.*, 146(2), (Jul. 26, 1999),267-72.

\* cited by examiner

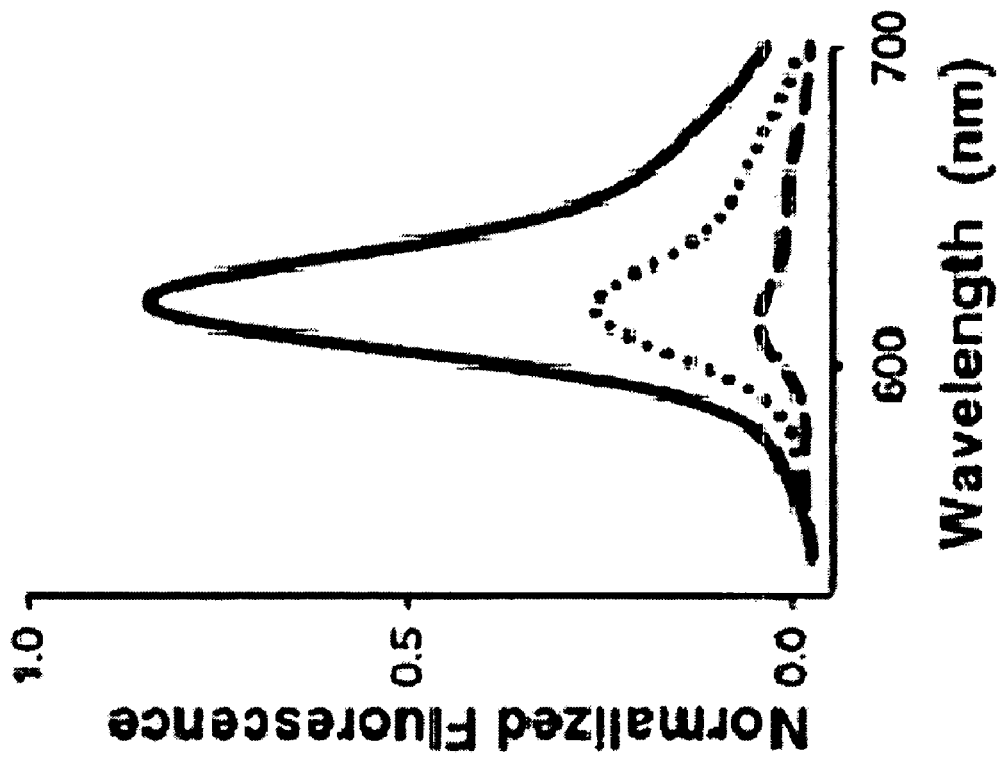
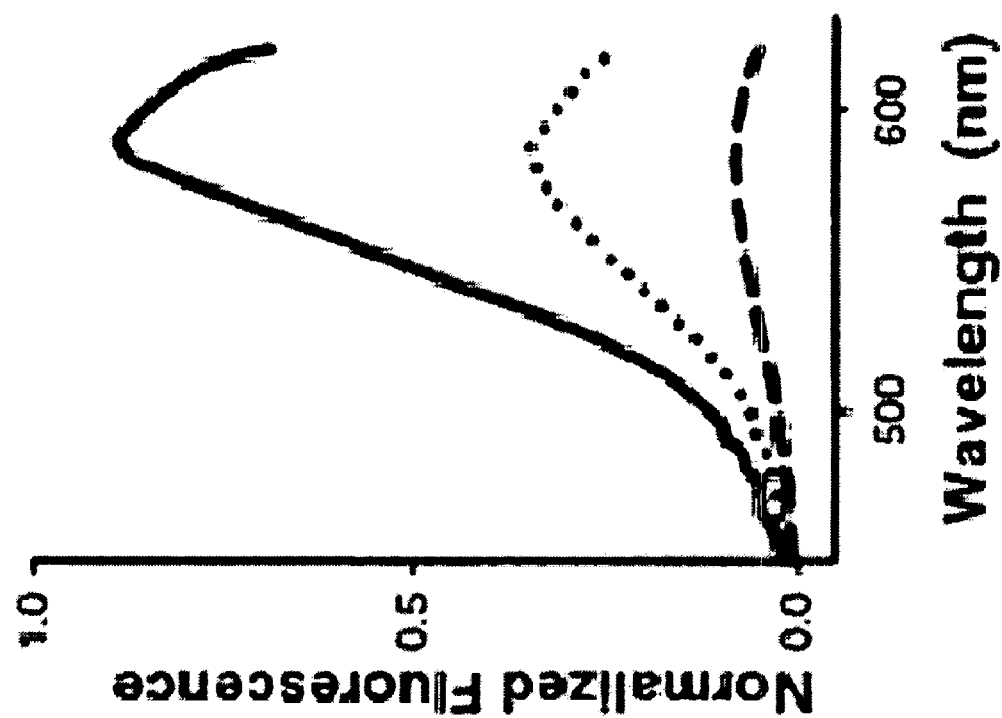
FIG. 5A
FIG. 5B

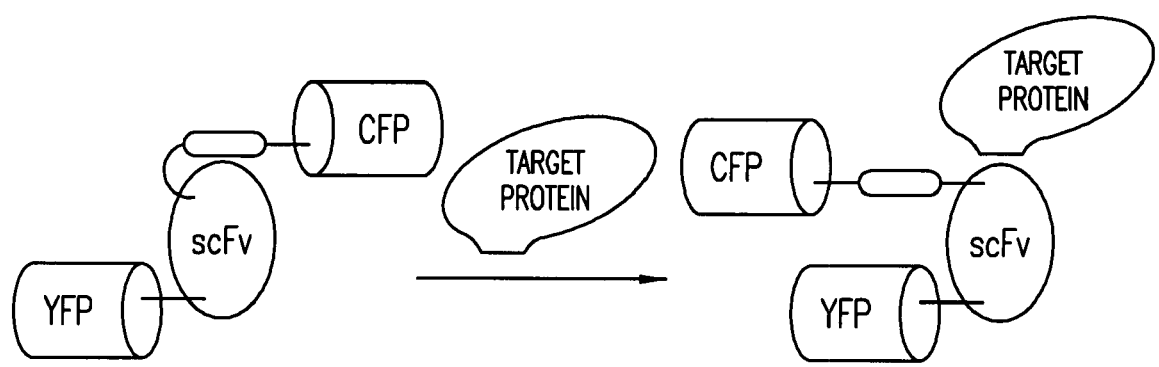
FIG. 14D1
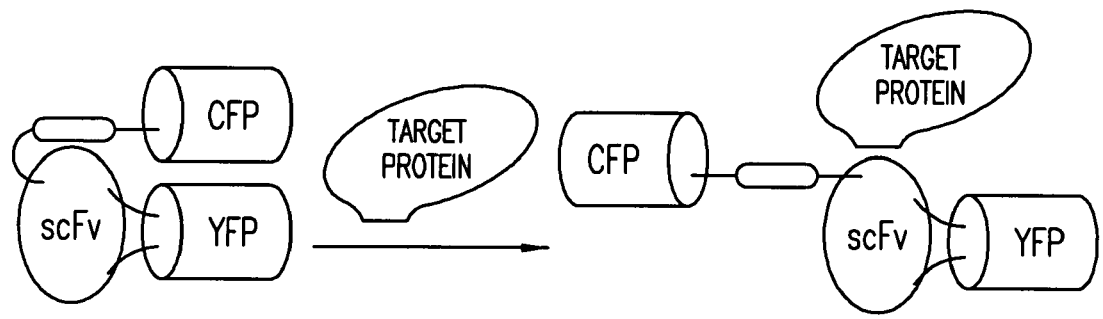
FIG. 14D2

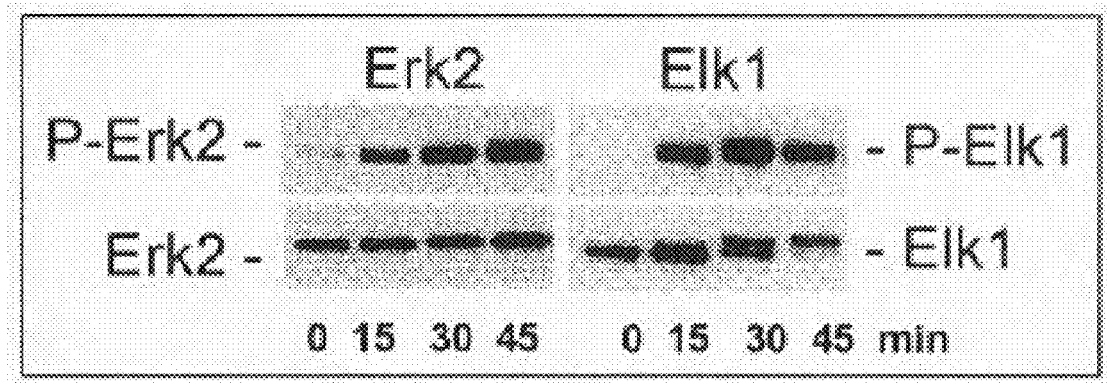
FIG. 15B1
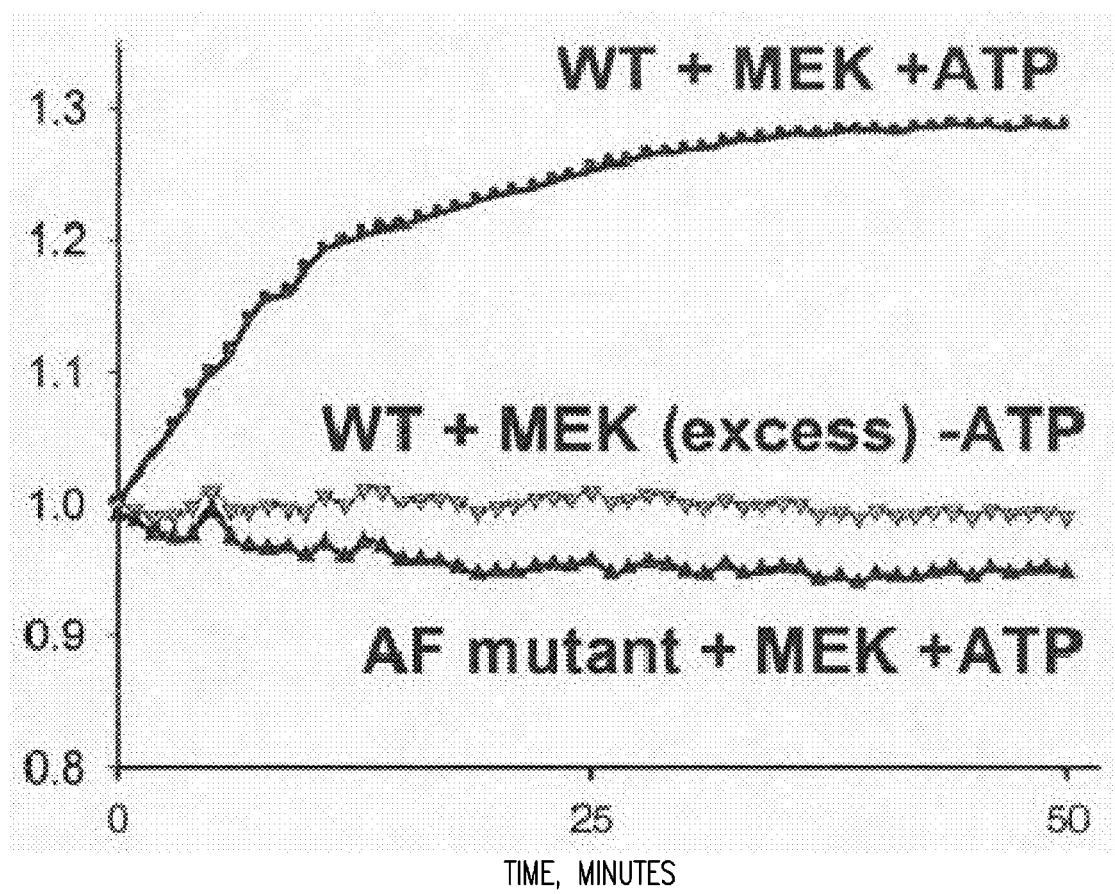
FIG. 15B2

SEQUENCE LISTING

```
<160> NUMBER OF SEQ ID NOS: 28

<210> SEQ ID NO 1
<211> LENGTH: 142
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 21-45
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 61-85
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 118-142
<223> OTHER INFORMATION: Xaa = any amino acid or no amino acid for up to
```

22 of the 25 Xaa, wherein one or more Xaa can be cysteine

<400> SEQUENCE: 1

Leu Thr Gln Ser Pro Gly Thr Leu Ser Leu Ser Ala Gly Glu Arg Ala
1               5                   10                  15

Thr Leu Ser Cys Xaa Xaa Xaa Xaa Xaa Xaa Xaa Xaa Xaa Xaa Xaa Xaa
            20                  25                  30

Xaa Xaa Xaa Xaa Xaa Xaa Xaa Xaa Xaa Xaa Xaa Xaa Trp Tyr Gln
        35                  40                  45

Gln Lys Pro Gly Gln Ala Pro Arg Leu Leu Ile Tyr Xaa Xaa Xaa Xaa
    50                  55                  60

Xaa Xaa Xaa Xaa Xaa Xaa Xaa Xaa Xaa Xaa Xaa Xaa Xaa Xaa Xaa Xaa
65                  70                  75                  80

Xaa Xaa Xaa Xaa Xaa Gly Ile Pro Asp Arg Phe Ser Gly Ser Gly Ser
                85                  90                  95

Gly Thr Asp Phe Thr Leu Thr Ile Gly Arg Leu Glu Pro Glu Asp Leu
            100                 105                 110

Ala Val Tyr Tyr Cys Xaa Xaa Xaa Xaa Xaa Xaa Xaa Xaa Xaa Xaa Xaa
        115                 120                 125

Xaa Xaa Xaa Xaa Xaa Xaa Xaa Xaa Xaa Xaa Xaa Xaa Xaa
    130                 135                 140

<210> SEQ ID NO 2
<211> LENGTH: 168
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 30-54
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 69-93
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 126-150
<223> OTHER INFORMATION: Xaa = any amino acid or no amino acid for up to
      22 of the 25 Xaa, wherein one or more Xaa can be cysteine

<400> SEQUENCE: 2

Gln Val Gln Leu Val Gln Ser Gly Ala Glu Val Lys Lys Pro Gly Ser
1               5                   10                  15

Ser Val Gln Val Ser Cys Lys Ala Ser Gly Gly Thr Phe Xaa Xaa Xaa
            20                  25                  30

Xaa Xaa Xaa Xaa Xaa Xaa Xaa Xaa Xaa Xaa Xaa Xaa Xaa Xaa Xaa
        35                  40                  45

Xaa Xaa Xaa Xaa Xaa Trp Val Arg Gln Ala Pro Gly His Gly Leu
    50                  55                  60

Glu Trp Met Gly Xaa Xaa Xaa Xaa Xaa Xaa Xaa Xaa Xaa Xaa Xaa Xaa
65                  70                  75                  80

Xaa Xaa Xaa Xaa Xaa Xaa Xaa Xaa Xaa Xaa Xaa Xaa Arg Val Thr
                85                  90                  95

Phe Thr Ala Asp Gln Ala Thr Ser Thr Ala Tyr Met Glu Leu Thr Asn
            100                 105                 110

Leu Arg Ser Asp Asp Thr Ala Val Tyr Tyr Cys Ala Arg Xaa Xaa Xaa
        115                 120                 125

```
Xaa Xaa Xaa Xaa Xaa Xaa Xaa Xaa Xaa Xaa Xaa Xaa Xaa Xaa
    130                 135                 140

Xaa Xaa Xaa Xaa Xaa Xaa Trp Gly Gln Gly Thr Leu Val Thr Val Ser
145                 150                 155                 160

Ser Pro Arg Gly Pro Ala Gly Gln
                165

<210> SEQ ID NO 3
<211> LENGTH: 18
<212> TYPE: PRT
<213> ORGANISM: Artificial Sequence
<220> FEATURE:
<223> OTHER INFORMATION: A synthetic peptide

<400> SEQUENCE: 3

Gly Gly Gly Gly Ser Gly Gly Gly Ser Gly Gly Gly Gly Ser Arg
 1               5                  10                  15

Ser Ser

<210> SEQ ID NO 4
<211> LENGTH: 328
<212> TYPE: PRT
<213> ORGANISM: Artificial Sequence
<220> FEATURE:
<223> OTHER INFORMATION: A synthetic peptide
<220> FEATURE:
<221> NAME/KEY: SITE
<222> LOCATION: 21-45
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 61-85
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 118-142
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 190-214
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: 229-253
<223> OTHER INFORMATION: Xaa = any amino acid or no amino acid for up to
      22 of the 25 Xaa, wherein one or more Xaa can be cysteine
<220> FEATURE:
<221> NAME/KEY: SITE
<222> LOCATION: (286)...(310)
<223> OTHER INFORMATION: Xaa = any amino acid or no amino acid for up to
      22 of the 25 Xaa, wherein one or more Xaa can be cysteine

<400> SEQUENCE: 4

Leu Thr Gln Ser Pro Gly Thr Leu Ser Leu Ser Ala Gly Glu Arg Ala
 1               5                  10                  15

Thr Leu Ser Cys Xaa Xaa Xaa Xaa Xaa Xaa Xaa Xaa Xaa Xaa Xaa
                20                  25                  30

Xaa Xaa Xaa Xaa Xaa Xaa Xaa Xaa Xaa Xaa Xaa Xaa Xaa Trp Tyr Gln
        35                  40                  45

Gln Lys Pro Gly Gln Ala Pro Arg Leu Leu Ile Tyr Xaa Xaa Xaa Xaa
 50                  55                  60

Xaa Xaa Xaa Xaa Xaa Xaa Xaa Xaa Xaa Xaa Xaa Xaa Xaa Xaa Xaa Xaa
65                  70                  75                  80
```

Xaa Xaa Xaa Xaa Xaa Gly Ile Pro Asp Arg Phe Ser Gly Ser Gly Ser
            85                  90                  95

Gly Thr Asp Phe Thr Leu Thr Ile Gly Arg Leu Glu Pro Glu Asp Leu
            100                 105                 110

Ala Val Tyr Tyr Cys Xaa Xaa Xaa Xaa Xaa Xaa Xaa Xaa Xaa
            115                 120                 125

Xaa Xaa Xaa Xaa Xaa Xaa Xaa Xaa Xaa Xaa Xaa Xaa Gly Gly
        130                 135                 140

Gly Gly Ser Gly Gly Gly Ser Gly Gly Gly Ser Arg Ser Ser
145                 150                 155                 160

Gln Val Gln Leu Val Gln Ser Gly Ala Glu Val Lys Pro Gly Ser
                165                 170                 175

Ser Val Gln Val Ser Cys Lys Ala Ser Gly Gly Thr Phe Xaa Xaa Xaa
            180                 185                 190

Xaa Xaa Xaa Xaa Xaa Xaa Xaa Xaa Xaa Xaa Xaa Xaa Xaa Xaa
        195                 200                 205

Xaa Xaa Xaa Xaa Xaa Xaa Trp Val Arg Gln Ala Pro Gly His Gly Leu
        210                 215                 220

Glu Trp Met Gly Xaa Xaa Xaa Xaa Xaa Xaa Xaa Xaa Xaa Xaa Xaa
225                 230                 235                 240

Xaa Xaa Xaa Xaa Xaa Xaa Xaa Xaa Xaa Xaa Xaa Xaa Arg Val Thr
            245                 250                 255

Phe Thr Ala Asp Gln Ala Thr Ser Thr Ala Tyr Met Glu Leu Thr Asn
            260                 265                 270

Leu Arg Ser Asp Asp Thr Ala Val Tyr Tyr Cys Ala Arg Xaa Xaa Xaa
            275                 280                 285

Xaa Xaa Xaa Xaa Xaa Xaa Xaa Xaa Xaa Xaa Xaa Xaa Xaa Xaa Xaa
        290                 295                 300

Xaa Xaa Xaa Xaa Xaa Xaa Trp Gly Gln Gly Thr Leu Val Thr Val Ser
305                 310                 315                 320

Ser Pro Arg Gly Pro Ala Gly Gln
            325

<210> SEQ ID NO 5
<211> LENGTH: 109
<212> TYPE: PRT
<213> ORGANISM: Artificial Sequence
<220> FEATURE:
<223> OTHER INFORMATION: A synthetic peptide

<400> SEQUENCE: 5

Thr Cys Thr Leu Thr Gln Ser Pro Gly Thr Leu Ser Leu Ser Ala Gly
1               5                   10                  15

Glu Arg Ala Thr Leu Ser Cys Arg Ala Ser Gln Ser Val Ser Ser Gly
            20                  25                  30

Ser Leu Ala Trp Tyr Gln Gln Lys Pro Gly Gln Ala Pro Arg Leu Leu
        35                  40                  45

Ile Tyr Gly Ala Ser Thr Arg Ala Thr Gly Ile Pro Asp Arg Phe Ser
    50                  55                  60

Gly Ser Gly Ser Gly Thr Asp Phe Thr Leu Thr Ile Gly Arg Leu Glu
65                  70                  75                  80

Pro Glu Asp Leu Ala Val Tyr Tyr Cys Gln Gln Tyr Gly Thr Ser Pro
            85                  90                  95

Tyr Thr Phe Gly Gln Gly Thr Lys Val Asp Ile Lys Arg
            100                 105

```
<210> SEQ ID NO 6
<211> LENGTH: 12
<212> TYPE: PRT
<213> ORGANISM: Artificial Sequence
<220> FEATURE:
<223> OTHER INFORMATION: A synthetic peptide

<400> SEQUENCE: 6

Arg Ala Ser Gln Ser Val Ser Ser Gly Ser Leu Ala
 1               5                  10

<210> SEQ ID NO 7
<211> LENGTH: 7
<212> TYPE: PRT
<213> ORGANISM: Artificial Sequence
<220> FEATURE:
<223> OTHER INFORMATION: A synthetic peptide

<400> SEQUENCE: 7

Gly Ala Ser Thr Arg Ala Thr
 1               5

<210> SEQ ID NO 8
<211> LENGTH: 20
<212> TYPE: PRT
<213> ORGANISM: Artificial Sequence
<220> FEATURE:
<223> OTHER INFORMATION: A synthetic peptide

<400> SEQUENCE: 8

Gln Gln Tyr Gly Thr Ser Pro Tyr Thr Phe Gly Gln Gly Thr Lys Val
 1               5                  10                  15

Asp Ile Lys Arg
            20

<210> SEQ ID NO 9
<211> LENGTH: 12
<212> TYPE: PRT
<213> ORGANISM: Artificial Sequence
<220> FEATURE:
<223> OTHER INFORMATION: A synthetic peptide

<400> SEQUENCE: 9

Arg Ala Ser Gln Ser Val Ser Ser Gly Cys Leu Ala
 1               5                  10

<210> SEQ ID NO 10
<211> LENGTH: 7
<212> TYPE: PRT
<213> ORGANISM: Artificial Sequence
<220> FEATURE:
<223> OTHER INFORMATION: A synthetic peptide

<400> SEQUENCE: 10

Gly Ala Ser Cys Arg Ala Thr
 1               5

<210> SEQ ID NO 11
<211> LENGTH: 20
<212> TYPE: PRT
<213> ORGANISM: Artificial Sequence
<220> FEATURE:
<223> OTHER INFORMATION: A synthetic peptide

<400> SEQUENCE: 11
```

Gln Gln Tyr Gly Thr Ser Pro Cys Thr Phe Gly Gln Gly Thr Lys Val
1               5                   10                  15

Asp Ile Lys Arg
            20

<210> SEQ ID NO 12
<211> LENGTH: 138
<212> TYPE: PRT
<213> ORGANISM: Artificial Sequence
<220> FEATURE:
<223> OTHER INFORMATION: A synthetic peptide

<400> SEQUENCE: 12

Gln Val Gln Leu Val Gln Ser Gly Ala Glu Val Lys Lys Pro Gly Ser
1               5                   10                  15

Ser Val Gln Val Ser Cys Lys Ala Ser Gly Gly Thr Phe Ser Met Tyr
            20                  25                  30

Gly Phe Asn Trp Val Arg Gln Ala Pro Gly His Gly Leu Glu Trp Met
        35                  40                  45

Gly Gly Ile Ile Pro Ile Phe Gly Thr Ser Asn Tyr Ala Gln Lys Phe
    50                  55                  60

Arg Gly Arg Val Thr Phe Thr Ala Asp Gln Ala Thr Ser Thr Ala Tyr
65                  70                  75                  80

Met Glu Leu Thr Asn Leu Arg Ser Asp Asp Thr Ala Val Tyr Tyr Cys
                85                  90                  95

Ala Arg Asp Phe Gly Pro Asp Trp Glu Asp Gly Asp Ser Tyr Asp Gly
            100                 105                 110

Ser Gly Arg Gly Phe Phe Asp Phe Trp Gly Gln Gly Thr Leu Val Thr
        115                 120                 125

Val Ser Ser Pro Arg Gly Pro Ala Gly Gln
    130                 135

<210> SEQ ID NO 13
<211> LENGTH: 6
<212> TYPE: PRT
<213> ORGANISM: Artificial Sequence
<220> FEATURE:
<223> OTHER INFORMATION: A synthetic peptide

<400> SEQUENCE: 13

Ser Met Tyr Gly Phe Asn
1               5

<210> SEQ ID NO 14
<211> LENGTH: 17
<212> TYPE: PRT
<213> ORGANISM: Artificial Sequence
<220> FEATURE:
<223> OTHER INFORMATION: A synthetic peptide

<400> SEQUENCE: 14

Gly Ile Ile Pro Ile Phe Gly Thr Ser Asn Tyr Ala Gln Lys Phe Arg
1               5                   10                  15

Gly

<210> SEQ ID NO 15
<211> LENGTH: 22
<212> TYPE: PRT
<213> ORGANISM: Artificial Sequence
<220> FEATURE:
<223> OTHER INFORMATION: A synthetic peptide

```
<400> SEQUENCE: 15

Asp Phe Gly Pro Asp Trp Glu Asp Gly Asp Ser Tyr Asp Gly Ser Gly
1               5                   10                  15

Arg Gly Phe Phe Asp Phe
            20

<210> SEQ ID NO 16
<211> LENGTH: 6
<212> TYPE: PRT
<213> ORGANISM: Artificial Sequence
<220> FEATURE:
<223> OTHER INFORMATION: A synthetic peptide

<400> SEQUENCE: 16

Ser Met Tyr Gly Cys Asn
1               5

<210> SEQ ID NO 17
<211> LENGTH: 17
<212> TYPE: PRT
<213> ORGANISM: Artificial Sequence
<220> FEATURE:
<223> OTHER INFORMATION: A synthetic peptide

<400> SEQUENCE: 17

Gly Ile Ile Pro Cys Phe Gly Thr Ser Asn Tyr Ala Gln Lys Phe Arg
1               5                   10                  15

Gly

<210> SEQ ID NO 18
<211> LENGTH: 17
<212> TYPE: PRT
<213> ORGANISM: Artificial Sequence
<220> FEATURE:
<223> OTHER INFORMATION: A synthetic peptide

<400> SEQUENCE: 18

Gly Ile Ile Pro Ile Phe Gly Thr Ser Asn Tyr Ala Gln Lys Phe Cys
1               5                   10                  15

Gly

<210> SEQ ID NO 19
<211> LENGTH: 22
<212> TYPE: PRT
<213> ORGANISM: Artificial Sequence
<220> FEATURE:
<223> OTHER INFORMATION: A synthetic peptide

<400> SEQUENCE: 19

Asp Cys Gly Pro Asp Trp Glu Asp Gly Asp Ser Tyr Asp Gly Ser Gly
1               5                   10                  15

Arg Gly Phe Phe Asp Phe
            20

<210> SEQ ID NO 20
<211> LENGTH: 22
<212> TYPE: PRT
<213> ORGANISM: Artificial Sequence
<220> FEATURE:
<223> OTHER INFORMATION: A synthetic peptide

<400> SEQUENCE: 20

Asp Phe Gly Pro Asp Trp Glu Asp Cys Asp Ser Tyr Asp Gly Ser Gly
1               5                   10                  15
```

```
Arg Gly Phe Phe Asp Phe
            20

<210> SEQ ID NO 21
<211> LENGTH: 22
<212> TYPE: PRT
<213> ORGANISM: Artificial Sequence
<220> FEATURE:
<223> OTHER INFORMATION: A synthetic peptide

<400> SEQUENCE: 21

Asp Phe Gly Pro Asp Trp Glu Asp Gly Asp Cys Tyr Asp Gly Ser Gly
1               5                   10                  15

Arg Gly Phe Phe Asp Phe
            20

<210> SEQ ID NO 22
<211> LENGTH: 22
<212> TYPE: PRT
<213> ORGANISM: Artificial Sequence
<220> FEATURE:
<223> OTHER INFORMATION: A synthetic peptide

<400> SEQUENCE: 22

Asp Phe Gly Pro Asp Trp Glu Asp Gly Asp Ser Tyr Asp Cys Ser Gly
1               5                   10                  15

Arg Gly Phe Phe Asp Phe
            20

<210> SEQ ID NO 23
<211> LENGTH: 354
<212> TYPE: DNA
<213> ORGANISM: Artificial Sequence
<220> FEATURE:
<223> OTHER INFORMATION: A synthetic oligonucleotide

<400> SEQUENCE: 23
gctaccgtgg cccaggcggc cgagcgcgat attgtgctga cgcagtctcc aggcaccctg      60
tctttgtctg caggggaaag agccaccctc tcctgcaggg ccagtcagag tgttagcagc     120
ggctccttag cctggtacca gcagaaacct ggtcaggctc ccaggctcct catctacggt     180
gcatccacca gggccactgg catcccagac aggttcagtg gcagtgggtc tgggacagac     240
ttcactctca caatcggcag actggagcct gaagatctcg cagtatatta ctgtcagcag     300
tatggtacct caccgtacac ttttggccag gggaccaaag tggatatcaa acgt           354

<210> SEQ ID NO 24
<211> LENGTH: 417
<212> TYPE: DNA
<213> ORGANISM: Artificial Sequence
<220> FEATURE:
<223> OTHER INFORMATION: A synthetic oligonucleotide

<400> SEQUENCE: 24
tcccaggtcc agcttgtgca gtctggggct gaggtgaaga agcctgggtc ctcggtgcag      60
gtctcctgca aggcctctgg aggcaccttc agcatgtatg gtttcaactg ggtgcgacag     120
gcccctggac atggcttga gtggatggga gggatcatcc ctatctttgg tacatcaaac     180
tacgcacaga gttccgggg cagagtcacg tttaccgcgg accaagccac gagcacagcc     240
tacatggagc tgaccaacct gcgatctgac gacacggccg tctattattg tgcgagagat     300
tttggccccg actgggaaga cggtgattcc tatgatggta gtggccgggg gttctttgac     360
```
ttctggggcc agggaaccct ggtcaccgtc tcctcacctc gtgggccggc cgggcag    417

<210> SEQ ID NO 25
<211> LENGTH: 51
<212> TYPE: DNA
<213> ORGANISM: Artificial Sequence
<220> FEATURE:
<223> OTHER INFORMATION: A synthetic oligonucleotide

<400> SEQUENCE: 25
ggtggcggtg gctcgggcgg tggcggttca ggtggcggtg gctctagatc t    51

<210> SEQ ID NO 26
<211> LENGTH: 18
<212> TYPE: PRT
<213> ORGANISM: Artificial Sequence
<220> FEATURE:
<223> OTHER INFORMATION: A synthetic peptide

<400> SEQUENCE: 26

Gly Gly Gly Gly Ser Gly Gly Gly Gly Ser Gly Gly Gly Gly Ser Arg
1               5                   10                  15

Ser Ser

<210> SEQ ID NO 27
<211> LENGTH: 120
<212> TYPE: PRT
<213> ORGANISM: Homo sapiens

<400> SEQUENCE: 27

Asp Ile Gln Asn Pro Asp Ile Thr Ser Ser Arg Tyr Arg Gly Leu Pro
1               5                   10                  15

Ala Pro Gly Pro Ser Pro Ala Asp Lys Lys Arg Ser Gly Lys Lys Lys
            20                  25                  30

Ile Ser Lys Ala Asp Ile Gly Ala Pro Ser Gly Phe Lys His Val Ser
        35                  40                  45

His Val Gly Trp Asp Pro Gln Asn Gly Phe Asp Val Asn Asn Leu Asp
    50                  55                  60

Pro Asp Leu Arg Ser Leu Phe Ser Arg Ala Gly Ile Ser Glu Ala Gln
65                  70                  75                  80

Leu Thr Asp Ala Glu Thr Ser Lys Leu Ile Tyr Asp Phe Ile Glu Asp
                85                  90                  95

Gln Gly Gly Leu Glu Ala Val Arg Gln Glu Met Arg Gln Glu Pro
            100                 105                 110

Leu Pro Pro Pro Pro Pro Ser
        115                 120

<210> SEQ ID NO 28
<211> LENGTH: 502
<212> TYPE: PRT
<213> ORGANISM: Homo sapiens

<400> SEQUENCE: 28

Met Ser Gly Gly Pro Met Gly Gly Arg Pro Gly Gly Arg Gly Ala Pro
1               5                   10                  15

Ala Val Gln Gln Asn Ile Pro Ser Thr Leu Leu Gln Asp His Glu Asn
            20                  25                  30

Gln Arg Leu Phe Glu Met Leu Gly Arg Lys Cys Leu Thr Leu Ala Thr
        35                  40                  45

```
-continued

Ala Val Val Gln Leu Tyr Leu Ala Leu Pro Pro Gly Ala Glu His Trp
 50                  55                  60

Thr Lys Glu His Cys Gly Ala Val Cys Phe Val Lys Asp Asn Pro Gln
 65                  70                  75                  80

Lys Ser Tyr Phe Ile Arg Leu Tyr Gly Leu Gln Ala Gly Arg Leu Leu
                 85                  90                  95

Trp Glu Gln Glu Leu Tyr Ser Gln Leu Val Tyr Ser Thr Pro Thr Pro
                100                 105                 110

Phe Phe His Thr Phe Ala Gly Asp Cys Gln Ala Gly Leu Asn Phe
                115                 120                 125

Ala Asp Glu Asp Glu Ala Gln Ala Phe Arg Ala Leu Val Gln Glu Lys
130                 135                 140

Ile Gln Lys Arg Asn Gln Arg Gln Ser Gly Asp Arg Arg Gln Leu Pro
145                 150                 155                 160

Pro Pro Pro Thr Pro Ala Asn Glu Glu Arg Arg Gly Gly Leu Pro Pro
                165                 170                 175

Leu Pro Leu His Pro Gly Gly Asp Gln Gly Gly Pro Pro Val Gly Pro
                180                 185                 190

Leu Ser Leu Gly Leu Ala Thr Val Asp Ile Gln Asn Pro Asp Ile Thr
                195                 200                 205

Ser Ser Arg Tyr Arg Gly Leu Pro Ala Pro Gly Pro Ser Pro Ala Asp
210                 215                 220

Lys Lys Arg Ser Gly Lys Lys Ile Ser Lys Ala Asp Ile Gly Ala
225                 230                 235                 240

Pro Ser Gly Phe Lys His Val Ser His Val Gly Trp Asp Pro Gln Asn
                245                 250                 255

Gly Phe Asp Val Asn Asn Leu Asp Pro Asp Leu Arg Ser Leu Phe Ser
                260                 265                 270

Arg Ala Gly Ile Ser Glu Ala Gln Leu Thr Asp Ala Glu Thr Ser Lys
                275                 280                 285

Leu Ile Tyr Asp Phe Ile Glu Asp Gln Gly Gly Leu Glu Ala Val Arg
                290                 295                 300

Gln Glu Met Arg Arg Gln Glu Pro Leu Pro Pro Pro Pro Pro Pro Ser
305                 310                 315                 320

Arg Gly Gly Asn Gln Leu Pro Arg Pro Pro Ile Val Gly Gly Asn Lys
                325                 330                 335

Gly Arg Ser Gly Pro Leu Pro Pro Val Pro Leu Gly Ile Ala Pro Pro
                340                 345                 350

Pro Pro Thr Pro Arg Gly Pro Pro Pro Gly Arg Gly Gly Pro Pro
                355                 360                 365

Pro Pro Pro Pro Ala Thr Gly Arg Ser Gly Pro Leu Pro Pro Pro
370                 375                 380

Pro Pro Gly Ala Gly Gly Pro Pro Met Pro Pro Pro Pro Pro Pro
385                 390                 395                 400

Pro Pro Pro Pro Ser Ser Gly Asn Gly Pro Ala Pro Pro Pro Leu Pro
                405                 410                 415

Pro Ala Leu Val Pro Ala Gly Gly Leu Ala Gly Gly Gly Arg Gly
                420                 425                 430

Ala Leu Leu Asp Gln Ile Arg Gln Gly Ile Gln Leu Asn Lys Thr Pro
                435                 440                 445

Gly Ala Pro Glu Ser Ser Ala Leu Gln Pro Pro Pro Gln Ser Ser Glu
450                 455                 460
```

```
Gly Leu Val Gly Ala Leu Met His Val Met Gln Lys Arg Ser Arg Ala
465             470             475             480

Ile His Ser Ser Asp Glu Gly Glu Asp Gln Ala Gly Asp Glu Asp Glu
                485             490             495

Asp Asp Glu Trp Asp Asp
            500
```

LIVE CELL BIOSENSORS

This application claims benefit of the filing date of U.S. Provisional Application Ser. No. 60/552,663, filed Mar. 12, 2004, the contents of which are incorporated herein in their entirety.

GOVERNMENT FUNDING

The invention described herein was made with United States Government support under Grant Numbers R01-AG-15430 and R01-GM-57464 awarded by the National Institutes of Health. The United States Government has certain rights in this invention.

FIELD OF THE INVENTION

The invention relates to environmentally-sensitive dyes, use of the dyes to report protein activities, biosensor molecules that can bind to selected targets, and methods for detecting target biomolecules and protein activities, for example, within living cells.

BACKGROUND OF THE INVENTION

Cell behavior is regulated through transient activation of protein activities at specific subcellular locations. Our ability to study translocation of proteins has been greatly enhanced by advances in the microscopy of fluorescent protein analogues within living cells. However, in many cases, localized protein activities are controlled not by translocating proteins to the site of action, but by localized activation of a small portion of the protein pool. Hahn, K.; Toutchkine, A. *Curr. Opin. Cell Biol.* 2002, 14, 167-172; Wouters, F. S.; Verveer, P. J.; Bastiaens, P. I. *Trends Cell Biol.* 2001, 11, 203-211. Such behaviors are not apparent when studying protein translocations or when using in vitro biochemical approaches. Furthermore, the outcome of signaling protein activation can depend on subtle variations in activation kinetics that are not discernible in the population averages generated by biochemical techniques. For precise quantification of rapid activation kinetics and of the level of protein activation, it is also necessary to measure protein activity in living cells. Wouters, F. S.; Verveer, P. J.; Bastiaens, P. I. *Trends Cell Biol.* 2001, 11, 203-211; Williams, D. A.; Fogarty, K. E.; Tsien, R. Y.; Fay, F. S. *Nature* 1985, 318, 558-561; Berridge, M. J. *J. Biol. Chem.* 1990, 265, 9583-9586.

Protein activity in living cells has occasionally been observed using FRET (fluorescence resonance energy transfer). Similarly, the interactions between two proteins have been observed by tagging each with different fluorophores that undergo FRET when the proteins associate. FRET biosensors have also been built, which bind to a protein only when it adopts a specific conformation. These approaches can be useful, but FRET-based techniques suffer from limitations that prevent the study of many important targets. Proteins undergoing conformational changes often cannot be "sampled" by a biosensor because the protein is bound to a competing ligand or is incorporated in a multi-protein complex, where it is blocked from biosensor access. However, it is precisely such large, unstable complexes that are difficult to reproduce in vitro and whose transient formation in specific locations must be studied in intact cells. Even when a protein is not sterically blocked, derivatization with a fluorophore near regions of conformational change for FRET can affect biological activity. Finally, because FRET is generated through indirect excitation, it produces a relatively weak fluorescence signal. Such a low signal leads to low sensitivity and to the need for complicated methods to differentiate the real signal from autofluorescence or fluorescence of the FRET donor.

Therefore, a need exists for tools that can do more than monitor protein movements, and do so without the above-mentioned disadvantages of FRET. There is a need for biosensors that can be used to detect and quantify diverse protein activities, including changing subcellular locations, conformational changes, activation states, posttranslational modifications, and/or small ligand binding of proteins in vivo.

SUMMARY OF THE INVENTION

The invention provides dyes and biosensors that can be used to detect and quantify changing subcellular locations, conformational changes, activation states, posttranslational modifications, and/or ligand binding of proteins in vivo.

For example, the dyes of the invention can be compounds of any one of formulae 1-5:

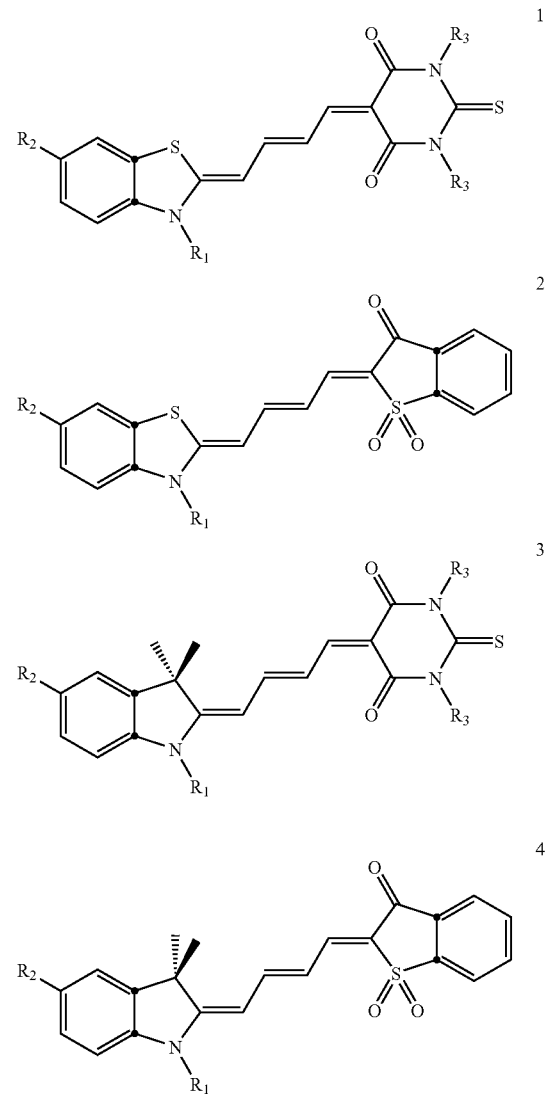

-continued

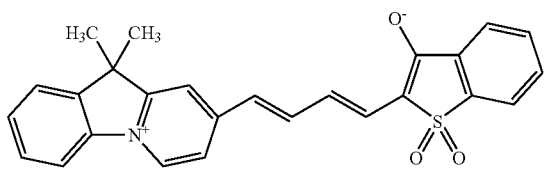

wherein:
R₁ is lower alkyl, —(CH₂)₃—SO₃⁻, —(CH₂)₃—NH—CO—CH₂—I or —(CH₂)₃—N⁺(CH₃)₂—(CH₂)₂—NCS; and
R₂ is H, —NH₂, —SO₃⁻, CH₃CONH—, ICH₂CONH—, HO(CH₂)₂—S—CH₂CONH—; SuOCOCH₂OCH₂CON(CH₃)— or a protecting group; and
R₃ is lower alkyl or tolyl-acetonitrile.

As used herein, Su means succinimidyl ester.

These dyes undergo changes in fluorescence properties as a function of their environment, and so can be used to detect protein activities. Such changes include altered fluorescence intensity, lifetime, excitation or emission maxima, altered shape of excitation or emission maxima, or fluorescence lifetime.

The invention also provides a biosensor binding domain comprising a single chain variable fragment (scFv) of an antibody with an attachment site for a dye on the scFv. In some embodiments, the attachment site for the dye within the biosensor binding domain is a cysteine.

For example, the biosensors of the invention include single chain variable fragments having SEQ ID NO: 1, SEQ ID NO: 2 or SEQ ID NO: 4 and a label or dye, wherein

```
                                        SEQ ID NO:1
is
LTQSPGTLSLSAGERATLSC(X)ₙWYQQKPGQAP
RLLIY(X)ₙGIPDRFSGSGSGTDFTLTIGRLEPEDLAVYYC(X)ₙ;

SEQ ID NO:2
is
QVQLVQSGAEVKKPGSSVQVSCKASGGTF(X)ₙWVRQAPG
HGLEWMG(X)ₙRVTFTADQATSTAYMELTNLRSDDTAVYY
CAR(X)ₙWGQGTLVTVSSPRGPAGQ;
and SEQ ID NO:4
is
LTQSPGTLSLSAGERATLSC(X)ₙWYQQKPGQA
PRLLIY(X)ₙGIPDRFSGSGSGTDFTLTIGRLEPEDLAVYYC(X)ₙG
GGGSGGGGSGGGGSRSSQVQLVQSGAEVKKPGSSVQVSCKASGGTF
(X)ₙWVRQAPGHGLEWMG(X)ₙRVTFTADQATSTAYMELT
NLRSDDT AVYYCAR(X)ₙWGQGTLVTVSSPRGPAGQ;
``` wherein each X separately represents a variable amino acid, n is an integer between about 3 and about 25, and wherein one or more X amino acid can be a cysteine that provides an attachment site for the dye.

One aspect of the invention is a biosensor comprising a binding domain and a dye, wherein the binding domain is a single chain variable fragment (scFv) of an antibody with an attachment site for a dye within a complementarity determining region 3 (CDR3) region of the scFv.

Another aspect of the invention is a biosensor for detecting human immunodeficiency virus (HIV) comprising a binding domain that can bind to HIV and an attached dye, wherein the binding domain comprises a CDR fragment consisting essentially of a peptide having sequence RASQSVSSGCLA (SEQ ID NO: 9), GASCRAT (SEQ ID NO: 10), QQYGTSPCTFGQGTKVDIKR (SEQ ID NO: 11), SMYGCN (SEQ ID NO: 16), GIIPCFGTSNYAQKFRG (SEQ ID NO: 17), GIIPIFGTSNYAQKFCG (SEQ ID NO: 18), DCGPDWEDGDSYDGSGRGFFDF (SEQ ID NO: 19), DFGPDWEDCDSYDGSGRGFFDF (SEQ ID NO: 20), DFGPDWEDGDCYDGSGRGFFDF (SEQ ID NO: 21) or DFGPDWEDGDSYDCSGRGFFDF (SEQ ID NO: 22).

Another aspect of the invention is a method of detecting a selected target molecule comprising contacting the selected target molecule with a biosensor and observing a signal produced by this interaction. The biosensor comprises a binding domain and a dye, wherein the dye fluorescence is affected by the binding event. The binding domain can be a single chain variable fragment (scFv) of an antibody with an attachment site for a dye within a CDR3 region of the scFv, a modified fragment of a naturally occurring protein, or other entity that binds to a specific state of the targeted protein or polypeptide.

Another aspect of the invention is a method of detecting a selected target molecule within a cell comprising contacting the cell with a biosensor and observing whether a signal produced by the biosensor is changed, wherein the biosensor comprises a binding domain and a dye, and wherein the binding domain is a single chain variable fragment (scfv) of an antibody with an attachment site for a dye on the scFv.

Another aspect of the invention is a method of detecting a selected target molecule comprising contacting a test sample that may contain the selected target molecule with a biosensor and observing whether a signal produced by the biosensor becomes localized within the sample, wherein the biosensor comprises a binding domain and a dye, and wherein the binding domain is a single chain variable fragment (scFv) of an antibody with an attachment site for a dye within a CDR3 region of the scFv.

Another aspect of the invention is a kit comprising a biosensor and instructions for using the biosensor for detecting, monitoring or observing a selected target molecule, wherein the biosensor comprises a binding domain and a dye, and wherein the binding domain is a single chain variable fragment (scFv) of an antibody with an attachment site for a dye within a CDR3 region of the scFv.

Another aspect of the invention is a kit comprising a dye and instructions for using the dye, wherein the dye is a compound of formula 1, 2, 3, 4 or 5, depicted above. The kit can further comprise instructions for attaching the dye to a selected protein, polypeptide, or nucleic acid.

DESCRIPTION OF THE FIGURES

"37 CFR § 1.84(a)(2)(iii) states that "An amendment to the specification to insert (unless the specification contains or has been previously amended to contain) the following language as the first paragraph of the brief description of the drawings: The patent or application file contains at least one drawing executed in color. Copies of this patent or patent application publication with color drawing(s) will be provided by the Office upon request and payment of the necessary fee".

FIG. 5A-B provides normalized excitation and emission spectra of the I-SO dye 4b in different solvents: butanol (-), methanol (•••), and water( - - - ). Excitation spectra acquired with emission at 640 nm. Emission spectra acquired with excitation at 530 nm. C(4b) =0.01 /M.

FIG. 6A provides absorbance spectra of S-TBA dye 1b ($C_0$=1 µM) in butanol after different irradiation times: 0, 3, 23, 47, 74, and 120 h. FIG. 6B graphically illustrates the concentration decay of S-TBA dye 1b in butanol.

FIG. 9A provides a model of the biosensor. An environmentally-sensitive dye (circle) is covalently attached to the binding site of an antibody fragment (scFv). When the scFv binds to its target antigen, the dye (star) undergoes a large increase in fluorescence intensity.

FIG. 11A shows the maximal fluorescence response of various S—SO-conjugated scFv X5 polypeptides. Each of the scFv X5-S—SO conjugates was titrated with increasing concentrations of gp120/sCD4 and the emission intensity was measured at 625 nm. The fluorescence intensity at saturation was normalized to the intensity of the free scFv conjugate. FIG. 11B provides a graph showing the fluorescence intensity of various concentrations of gp120/sCD4 as detected using the H96C scFv X5 mutant conjugated to S—SO dye. The fluorescence intensity was measured at 625 nm. Ovalbumin or sCD4 alone produced no response. FIG. 11C provides the excitation and emission spectra of H96-scFv X5-S—SO before and after binding to gp120/sCD4. FIG. 11D shows the increase in fluorescence emission of scFv X5 conjugated to either S—SO or I—SO, at saturation with gp120/sCD4. The fluorescence intensity was measured at 625 nm (S—SO) or 630 nm (I—SO), then normalized to the intensity of the free scFv conjugate.

FIG. 12A provides a ribbon model of Fv X5 highlighting the dye attachment sites. Side chains that were replaced by cysteines and coupled with dye are illustrated in ball-and-stick form. The coloring corresponds to the S—SO fluorescence response at these positions upon target binding (red=5.9-fold change, orange=2- to 3-fold change, yellow=0.2- to 1.0-fold change, gray=no dye attachment). β-strands are illustrated as arrows, and loops as tubes.

FIG. 13A shows that X5 conjugated to dye at position H96 detects gp120 expressed on the surface of HEK 293T cells. Cells were transfected with gp120 and EGFP, or with EGFP alone. They were resuspended 36 hours post-transfection, then incubated with sCD4 and two different concentrations of the scFv conjugate. Fluorescence intensity was measured at 625 nm (S—SO) and 510 nm (EGFP), without washing the cells before measurement. The mean ratio of S—SO/EGFP fluorescence is shown for the cells expressing gp120, as a percentage increase over those expressing EGFP alone. Fluorescence was more than twice as high for cells expressing gp120. Results are representative of two separate experiments. FIG. 13B provides a photomicrograph verifying surface expression of gp120 on 293T cells. Fixed cells were incubated with an antibody against gp120, followed by a phycoerythrin-conjugated anti-F(ab')$_2$ secondary antibodies. FIG. 13C provides a photomicrograph of mock-transfected control cells that were exposed to sCD4.

FIGS. 14A-D present schematic diagrams of exemplary modular biosensor configurations. FIG. 14A shows a configuration in which an affinity molecule with a binding domain 140 is attached to target molecule 141 through linker 142. Dye 143 is attached to the target and provides a changed signal 144, when the domain binds to the target. The changed signal is typically produced by a change in the conformation, phosphorylation, ligand binding etc. that is "sensed" by the dye 143. FIG. 14B shows a configuration of a modular biosensor wherein the dye is linked to the binding domain. FIG. 14C shows a configuration of a modular biosensor wherein both the binding domain and target molecule segments of the sensor have an attached reporter dye for FRET. In some embodiments, it is advantageous to omit linker 142, so that the binding domain and reporter are not attached to each other. FIG. 14D1 and 14D2 illustrate two ways scFv-based biosensors interact with target molecules to produce positive signal changes or negative signal changes.

FIG. 15B1-2 show that attachment of the dye did not perturb phosphorylation of Erk2 (FIG. 15B1), or the ability of the labeled Erk2 to phosphorylate its substrate Elk1 (FIG. 15B2).

DETAILED DESCRIPTION OF THE INVENTION

Figure 1:
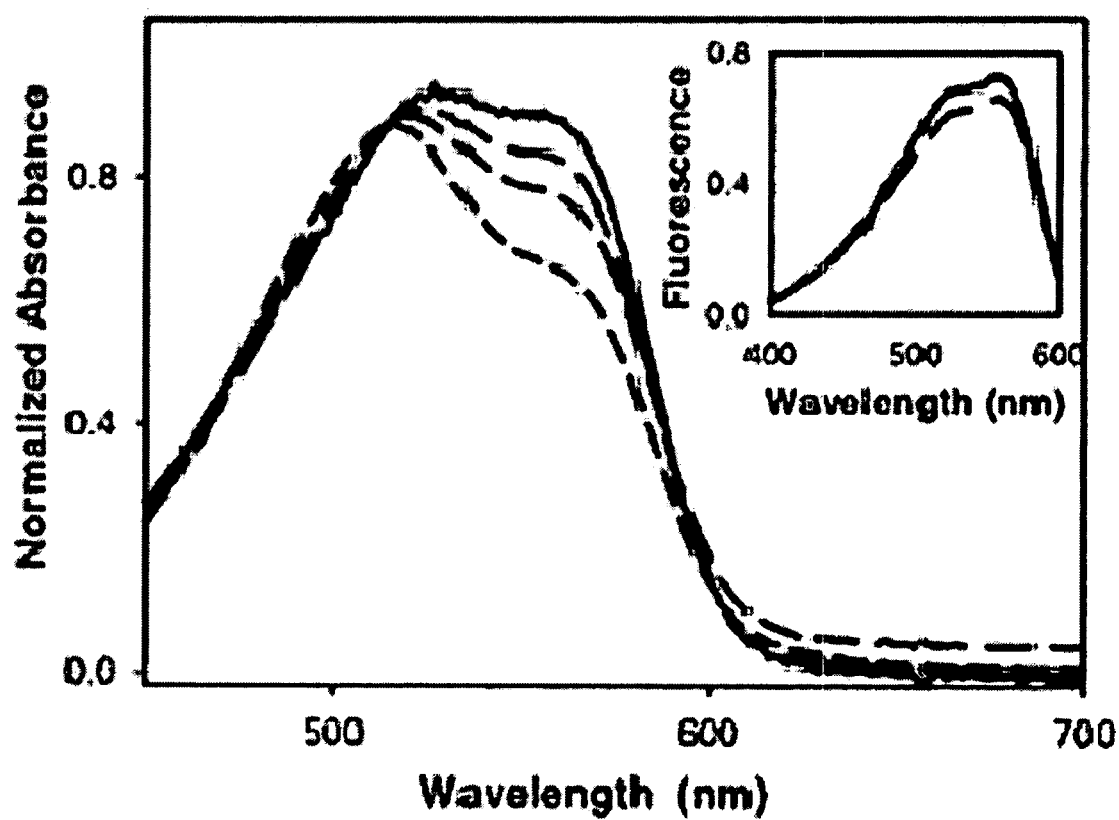
FIG. 1 provides absorbance and fluorescence (excitation) spectra of S-TBA dye 1c at different concentrations in water. Concentrations: 1.25 µM (-), 2.5 µM (- -), 12.5 µM (- - -), 25 µM (- - - ). Inset: Excitation spectra of dye 1c in water at 1.25 µM (-) and 2.5 µM (- -).
Figure 2A:
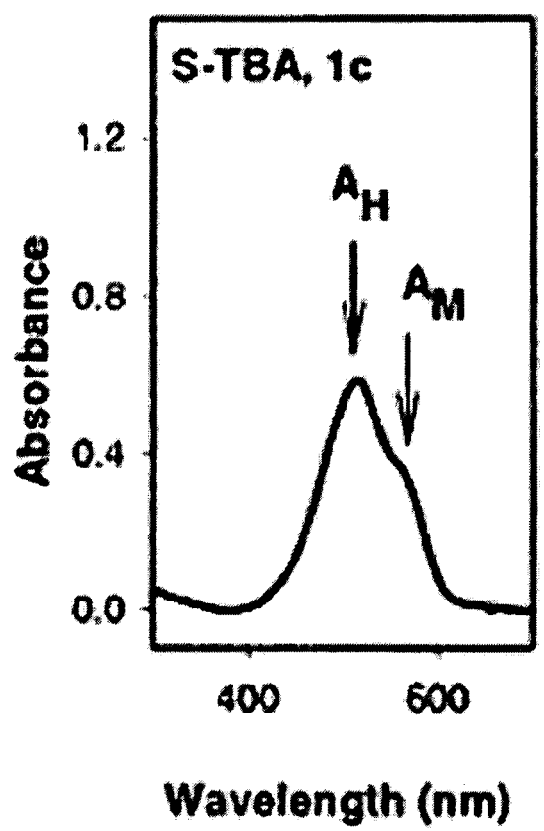
FIG. 2A-D provides absorbance spectra for dyes 1c (FIG. 2A), 2b (FIG. 2B), 3b (FIG. 2C), and 4b (FIG. 2D) in water. All concentrations were equal to 1.0 µM. $A_H$=absorbance due to aggregation; $A_M$=absorbance of monomer.
Figure 2B:
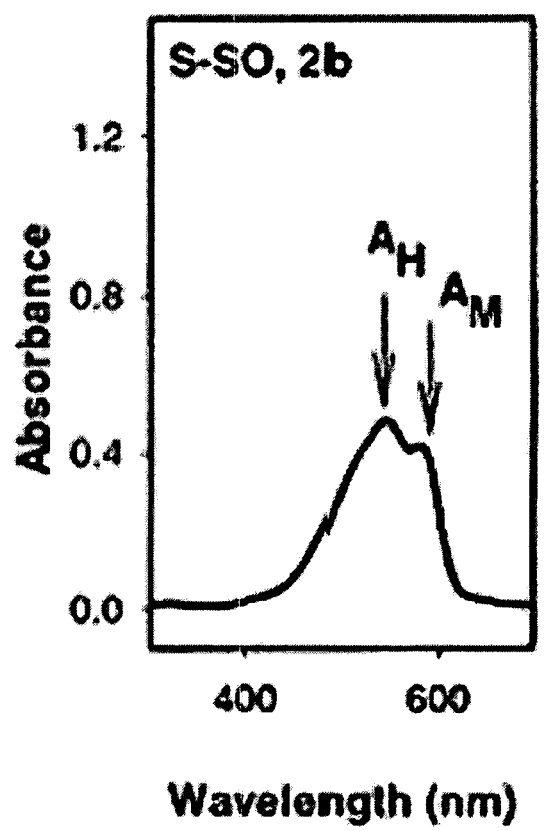
Figure 2C:
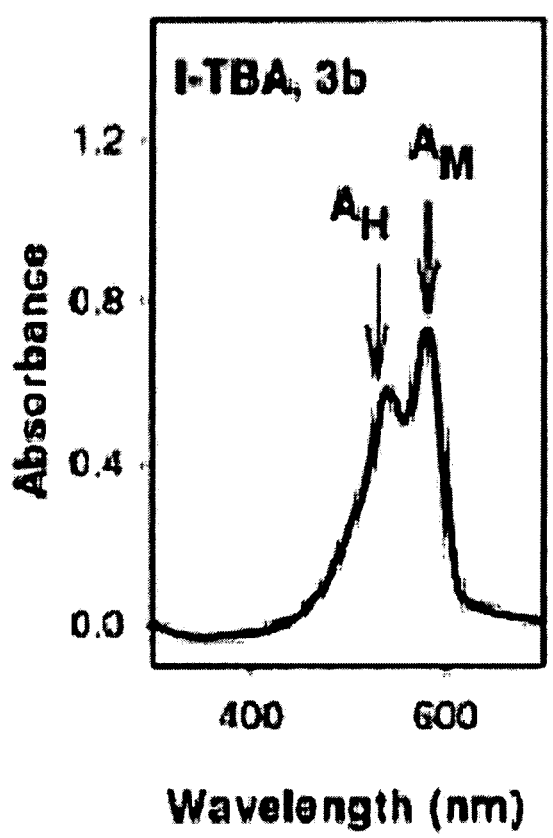
Figure 2D:
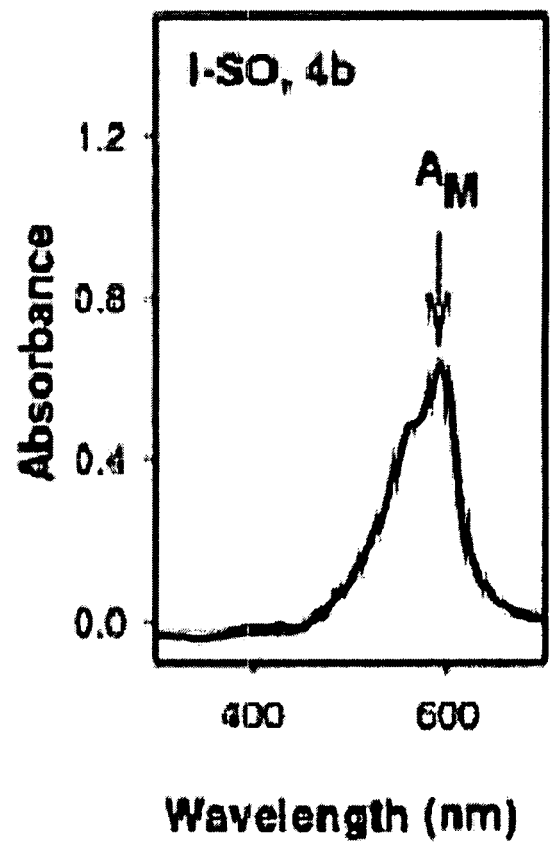

The invention is directed to biosensor molecules that can bind to and detect target molecules. The invention is also directed to the detection of such binding events using environmentally sensitive dyes with valuable properties for homogenous assays and live cell imaging. The invention is further directed towards direct attachment of the dyes to the protein of interest, where protein activity and/or conformational changes result in a change in the fluorescence of the dye. Biosensor molecules of the invention can include a binding domain and an environmentally sensitive dye, a protein of interest and an environmentally sensitive dye, or modular binding domains/target proteins linked or not linked, containing dyes for FRET or environmentally sensitive dye(s). The environmentally sensitive dyes can be attached to the binding domain or target at one or more locations. Optimized locations for attaching dyes to single chain variable fragments (scFv's) binding domains and to specific modified naturally occurring protein domains are provided. The biosensors of the invention are particularly well adapted for observing the function of target molecules within living cells.

The present invention provides various methods to examine protein activity, structure, or protein-protein interactions. Methods and biosensors of the invention can report protein localization, protein activation and/or report specific aspects of changing protein structure or interaction. The biosensors have specific features enabling them to be used in living cells. In many cases they can be used for homogeneous assays. For example, the activity of a protein in a complex mixture, such as cell lysate, can be determined simply by adding and detecting the biosensors without additional steps such as wash steps, and the like. The biosensors can be constructed to provide signals in a FRET format, or preferably, as in an environmentally sensitive single dye response. Environmentally sensitive dyes and their use in old or new biosensor approaches are an important aspect of the invention.

The invention provides biosensor binding domains having specific affinity for target molecules in a specific state of phosphorylation. For example, the binding domain of the biosensor can have specific affinity for a binding site produced upon a protein when that protein binds to a guanosine triphosphate, activating the signal transduction protein. Optionally, the biosensor has significantly lower affinity for the inactive form of the protein (e.g., the protein bound to guanosine diphosphate instead of guanosine triphosphate). Thus, for example, an environmentally sensitive dye of the biosensor can occupy a position on the binding domain near the binding site such that, upon binding to its target, the binding environment alters the fluorescent signal from the dye. The position can provide significant signal change in the dye without significantly inhibiting the biological activity of the targeted protein. Detection of the activated target in this embodiment does not necessarily require conformational changes in the target or the presence of third molecules interacting with the target.

The biosensors of the invention can also detect protein-protein interactions. Such interactions can be high affinity interactions, such as, e.g., interactions between antigens and antibodies, or they can be lower affinity interactions, such as, for example, interactions between enzymes and substrates, signal cascade members, or members of protein complexes. In a protein-protein interaction between two members, one member can be considered the "target" and the other the biosensor "probe." While the distinction between target and probe is somewhat arbitrary, because the two interact each other, these terms are used to facilitate discussion of protein interaction. Generally, as used herein, the target can be the molecule of interest to be detected and the probe can be a member introduced to interrogate a sample for the presence of the target in a state or form of interest. In a typical protein-protein biosensor of the invention, one member of the pair has a binding domain complimentary to a binding site of the second pair member. One or both of the protein-protein interaction pair members can include an attached environmentally sensitive dye. The protein-protein interaction pair members can be full-length, naturally occurring proteins, synthetic analogs of naturally occurring proteins, recombinant analogs of naturally occurring proteins, or fragments thereof. Biosensors comprising protein-protein interactions can have environmentally sensitive dyes at one or more positions on one or both members such that the dyes are between the members during binding. In such a situation, binding can cause significant changes in signal from the dye without significantly inhibiting the binding interaction between the members. More desirable or optimal dye positions can be identified by screening alternative positions for improved signal and/or binding function in biosensor systems of the invention.

In other embodiments, the biosensor can have specific affinity for a target molecule in a specific conformation, bound to a specific ligand, or with a specific posttranslational modification other than phosphorylation.

In one embodiment, a biosensor molecule was generated that included an HIV-1 neutralizing antibody Fab fragment (X5), which binds to HIV envelope protein gp120 after forming a complex with the host cell receptor CD4. See Moulard, M. et al., Broadly Cross-reactive HIV-1-neutralizing Human Monoclonal Fab Selected for Binding to gp120-CD4-CCR5 Complexes. *Proc Natl Acad Sci USA* 99, 6913-6918 (2002). The variable domains from the heavy ($V_H$) and light chain ($V_L$) of the X5 antibody fragment were tethered together to be expressed as a single chain variable fragment (scFv). Based on sequence data and the crystal structure of the free Fab fragment, several merocyanine dyes were attached to eleven different positions of this scFv X5 binding domain. Biosensors were obtained that responded with up to a 6-fold increase in fluorescence intensity upon gp120 binding in vitro. Expression of gp120 was visualized on living cells. This work demonstrates that the combination of such binding domains with such environmentally sensitive dyes can be successfully used to identify and define the level and/or location of subcellular targets in live cell dyes. The ability to monitor such properties over time enables the probes to follow kinetics of protein activity. Moreover, according to the invention, scFv binding domains are remarkably tolerant to the incorporation of dyes at a wide range of sites and many if not all scFv molecules can readily be used as binding domains with environmentally sensitive dyes incorporated at convenient sites selected by one of skill in the art. In a second embodiment, a fragment of WASP which binds only to the activated state of Cdc42 was used to detect Cdc42 activation. The fragment was covalently derivatized with I—SO or S—SO dyes. Upon binding to Cdc42 this led to a large increase in fluorescence intensity. The biosensor revealed the level of Cdc42 activity in vitro, in cell lysates, and in living cells.

Environmentally Sensitive Dyes

The invention provides environmentally sensitive dyes that have one or more aromatic rings and one or more nonplanar substituents that project out of the plane of the aromatic ring. The dye is "environmentally sensitive" because a signal from the dye changes when the dye is exposed to a change in environment, for example, a hydrophobicity, hydrogen bonding, polarity, or conformational change. Thus, a signal from an environmentally sensitive dye of the invention detectably changes upon exposure to a change in solvent, change in hydrogen bonding, change in the hydrophobicity of the environment, changed polarity or polarization, or change affecting the conformation of the dye. In one embodiment, the signal provided by the environmentally sensitive dye increases when the dye is exposed to an environment that is more hydrophobic. In another embodiment, the signal provided by the environmentally sensitive dye increases when the dye is exposed to an environment where there is increased hydrogen binding between the dye and a component of the environment. Such an increase in hydrophobicity or an increase in hydrogen bonding can occur when a biosensor of the invention binds to a target protein or subcellular component. In other embodiments, the signal provided by the environmentally sensitive dye decreases when the dye is exposed to an environment that is more hydrophilic. In further embodiments, the signal provided by the environmentally sensitive dye decreases when the dye is exposed to an environment that has less hydrogen binding. Such an increase in hydrophilicity or a decrease in hydrogen binding can occur when a biosensor of the invention is exposed to an aqueous environment or when such a biosensor becomes unbound from a target protein or subcellular component.

The aromatic rings that can be used in the dyes of the invention include aromatic hydrocarbon radicals of 6-20 carbon atoms derived by the removal of one hydrogen atom from a single carbon atom of a parent aromatic ring system. Typical aromatic rings include, but are not limited to, radicals derived from benzene, substituted benzene, naphthalene, anthracene, biphenyl, and the like. Fused ring systems are also contemplated, including fused rings with heteroatoms such as nitrogen, sulfur or oxygen. Examples of aromatic rings that can be used include indole, indoline, benzothiophene, dihydrobenzothiophene and the like.

Dyes of the invention can have many properties that make them particularly suitable for detection of targets and interactions in living cells. The dyes are, for example, bright, with long wavelengths outside of cellular autofluorescence background frequencies and that are less damaging to cells. Addition or deletion of parts of the aromatic system can shift excitation and/or emission wavelengths of the dyes so that more than one event can be monitored in a cell at the same time. The dyes of the invention can be designed to have enhanced water solubility, e.g., by attaching groups that sterically block aggregation without unduly increasing hydrophobicity. This is in contrast to the old and less desirable technique of enhancing water solubility using highly charged groups that can affect protein interaction. Dyes of the invention can be detected in cells by observing changes in intensity, a change in the shape or maxima of the excitation or emission peak, and/or dye lifetime, to permit ratio imaging and other techniques that can eliminate effects of uneven illumination, cell thickness etc.

Several dyes with excellent spectral properties were previously developed by the inventors, but reaction between these dyes and proteins led to attachment of multiple dyes, even when labeling was done at low dye concentrations. Moreover, the fluorescence of the "over-labeled" conjugates was weak. This suggested that the dyes were forming non-fluorescent H-aggregates in water, as reported previously for other merocyanines. Wurthner et al., *Angewandte Chemie, International Edition in English* 39, 1978-1981 (2000); Lu et al., L., *J. Am. Chem. Soc.* 121, 8146-8156 (1999); Valdes-Aguilera et al., *Acc. Chem. Res.* 22, 171-177 (1989). The essentially planar dyes previously developed are thought to be aggregating to reduce the exposure of their hydrophobic surfaces to water.

In the present invention, such aggregation was greatly decreased by incorporating bulky, non-planar substituents with tetragonal geometry in the aromatic rings, to make stacking unfavorable. This innovation led to dyes with good water solubility while retaining substantial hydrophobic character. These dyes can be responsive to protein conformational changes induced in the sensor itself, conformational changes in target molecules, binding of sensor to target to protein-protein interactions, and the like. The structure and spectra of one such dye is shown below, where the out-of-plane substituents are two the methyl groups bound to the carbon and the two oxygen atoms bound to the sulfur atom.

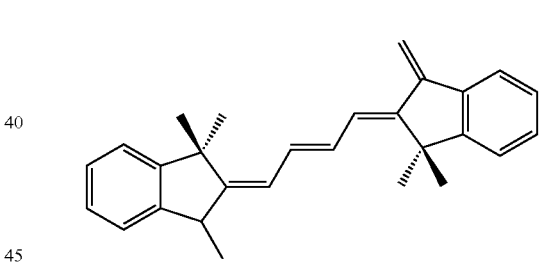

The $R_1$ group can be, e.g., any functional group that inhibits stacking of the aromatic rings and/or enhances water solubility. For example, well suited $R_1$ groups often provide significant steric hindrance to ring stacking without reducing water solubility of the dye molecule. The $R_1$ group can have, e.g., an aliphatic nature from single carbon to about 6 carbons. In a preferred embodiment, the $R_1$ group can have a polar or weakly charged character. Particularly preferred $R_1$ groups include, e.g., alkyl groups, alkyleneaminoalkyls, alkylenesulfate, —$(CH_2)_3$—$N^+(CH_3)_2$—$(CH_2)_2$—NCS, —$(CH_2)_3$—NH—CO—$CH_2$—I, —$(CH_2)_3$—$SO_3$, and/or the like. This compound is a compound having formula 4, described below.

To respond to solvent polarity, dyes of the invention can have a strong dipole that is influenced by the solvent environment. Merocyanine dyes of the invention can have an extended zwitterion structure with a polarized ground state (shown below).

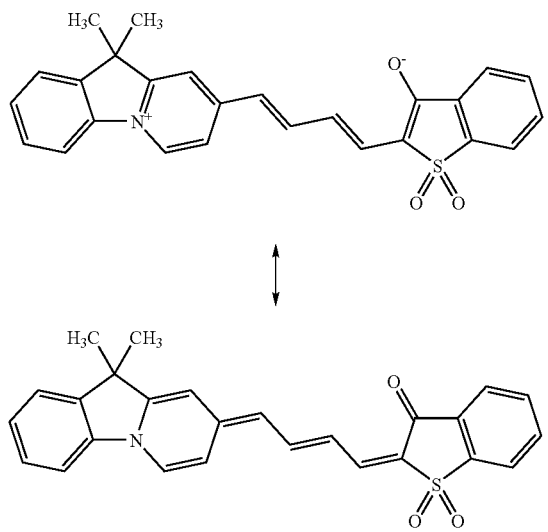

This exemplary dye can show a strong solvent-dependent excitation wavelength shift, while retaining bright fluorescence. Although the blue-shifted form has a broadened spectrum, a broad band filter can be used in the microscope for efficient excitation. The above fluorophore could be derivatized with side chains to prevent aggregation, improve solubility, affect interactions with proteins, and enable covalent attachment to proteins, as described for the other dyes in the application.

Dyes having, e.g., formulae 1-5, are an aspect of the invention. The invention provides these unique merocyanine dyes as general structures, as the structures with generally described R groups, and as specific structures with particularly preferred R groups. Preferred merocyanine dyes of the invention have one or more groups arranged in tetragonal geometry from rings of the dye. In many cases, the R groups include groups with one or more carbons providing significant steric hindrance to ring stacking, and/or polar to weak ionic character to enhance water solubility. Dyes of the invention can be compatible with aqueous chemistries or aqueous/organic solvent combinations used to prepare biosensors. The dyes can have reactive groups and/or protected groups to facilitate processes for binding dyes to binding domains. Biosensors of the invention, comprising, e.g., dyes linked to binding domains, can be compatible with and move freely in intracellular and/or extracellular environments of living sells. Dyes on the biosensors can exist, e.g., in or near binding regions between a sensor and target to provide a detectable signal without significantly interfering with binding.

Formula 1, above, is also referred to herein as S-TBA. A number of specific dye compounds can be made according to formula 1. Groups $R_1$, $R_2$ and/or $R_3$, can be provided with one carbon to 6 carbon groups providing steric hindrance and/or water solubility enhancement, as described above. Preferred embodiments of structure 1 include, e.g., compounds 1a-1h. The substituents present on each of dye compounds 1a-1h are as follows:

1a: $R_1$=—$(CH_2)_3$—$N^+(CH_3)_2$—$(CH_2)_2$—NCS; $R_2$=H; $R_3$=butyl.
1b: $R_1$=ethyl; $R_2$=H; $R_3$=methyl.
1c: $R_1$=—$(CH_2)_3$—$SO_3^-$; $R_2$=H; $R_3$=methyl.
1d: $R_1$=—$(CH_2)_3$—$SO_3^-$; $R_2$=FmocNH—; $R_3$=methyl.
1e: $R_1$=—$(CH_2)_3$—$SO_3^-$; $R_2$=$NH_2$; $R_3$=methyl.
1f: (S-TBA-IAA): $R_1$=—$(CH_2)_3$—$SO_3^-$; $R_2$=$ICH_2CONH_2$; $R_3$=methyl.
1g: $R_1$=—$(CH_2)_3$—$SO_3^-$; $R_2$=$CH_3CONH$—; $R_3$=methyl.
1h: $R_1$=—$(CH_2)_3$—$SO_3^-$; $R_2$=$HO(CH_2)_2$—S—$CH_2CONH$—; $R_3$=methyl.

Formula 2 is as follows.

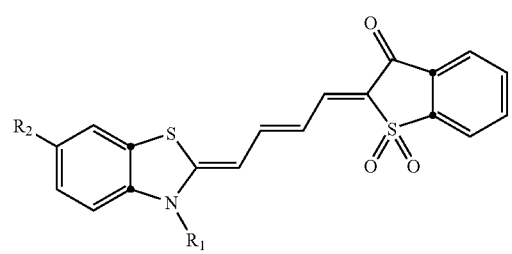

Structure 2 is also referred to herein as S—SO. Groups $R_1$ and/or $R_2$, can be provided with one carbon to 6 carbon groups providing steric hindrance and/or water solubility enhancement, as described above. A number of specific dye compounds can be made based 6n formula 2, including, e.g., those with structures 2a-2g. The substituents present on each of dye compounds 2a-2g are as follows:

2a: $R_1$=ethyl; $R_2$=H.
2b: $R_1$=—$(CH_2)_3$—$SO_3^-$; $R_2$=H.
2c: $R_1$=—$(CH_2)_3$—$SO_3^-$; $R_2$=FmocNH—.
2d: $R_1$=—$(CH_2)_3$—$SO_3^-$; $R_2$=$NH_2$.
2e: (S—SO—IAA): $R_1$=—$(CH_2)_3$—$SO_3^-$; $R_2$=$ICH_2CONH$—.
2f: (S—SO—OSu): $R_1$=—$(CH_2)_3$—$SO_3^-$; $R_2$=$SuOCOCH_2OCH_2CON(CH_3)$—.
2g: $R_1$=—$(CH_2)_3$—$SO_3^-$; $R_2$=$HO(CH_2)_2S$—$CH_2CONH$—.

Formula 3 is as follows.

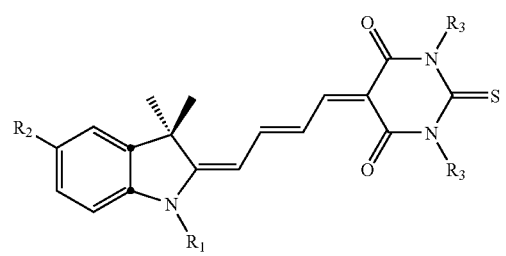

wherein:

R$_1$ is lower alkyl, —(CH$_2$)$_3$—SO$_3^-$, —(CH$_2$)$_3$—NH—CO—CH$_2$—I or —(CH$_2$)$_3$—N$^+$(CH$_3$)$_2$—(CH$_2$)$_2$—NCS; and R$_2$ is H, —NH$_2$, —SO$_3^-$, CH$_3$CONH—, ICH$_2$CONH—, HO(CH$_2$)$_2$—S—CH$_2$CONH—; SuOCOCH$_2$OCH$_2$CON(CH$_3$)— or a protecting group; and R$_3$ is lower alkyl or tolyl-acetonitrile.

In some embodiments, the compounds of formula 3 have the following structure:

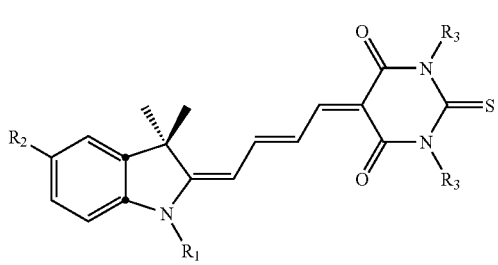

3

Structure 3 is also referred to herein as I-TBA. Groups R$_1$ and/or R$_2$, can be provided with one carbon to 6 carbon groups providing steric hindrance and/or water solubility enhancement, as described above. A number of different dye compounds can be made based on formula 3, including those, e.g., with structures 3a-3b. The substituents present on each of dye compounds 3a-3b are as follows:

3a: R$_1$=ethyl; R$_2$=H.
3b: R$_1$=—(CH$_2$)$_3$—SO$_3^-$; R$_2$=H.

Formula 4 is as follows.

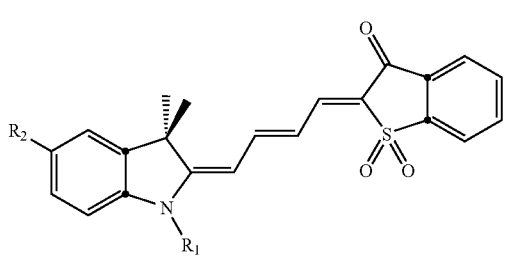

4

Structure 4 is also referred to herein as I—SO. Groups R$_1$ and/or R$_2$, can be provided with one carbon to 6 carbon groups providing steric hindrance and/or water solubility enhancement, as described above. A number of different dye compounds can be made based on formula 4, including, e.g., those with structures 4a-4g. The substituents present on each of dye compounds 4a-4g were as follows:

4a: R$_1$=methyl; R$_2$=H.
4b: R$_1$=—(CH$_2$)$_3$—SO$_3^-$; R$_2$=H.
4c: R$_1$=—(CH$_2$)$_3$—SO$_3^-$; R$_2$=FmocNH—.
4d: R$_1$=—(CH$_2$)$_3$—SO$_3^-$; R$_2$=NH$_2$.
4e: (I—SO—IAA): R$_1$=—(CH$_2$)$_3$—SO$_3^-$; R$_2$=ICH$_2$CONH—.
4f: (I—SO—OSu): R$_1$=—(CH$_2$)$_3$—SO$_3^-$; R$_2$=SuOCOCH$_2$OCH$_2$CON(CH$_3$)—.
4g: R$_1$=—(CH$_2$)$_3$—SO$_3$—; R$_2$=HO(CH$_2$)$_2$S—CH$_2$CONH—.

Formula 5 is as follows.

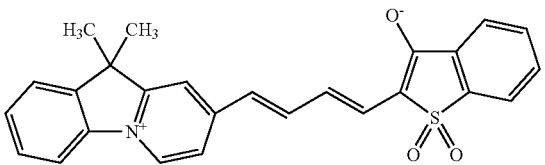

Figure 8:
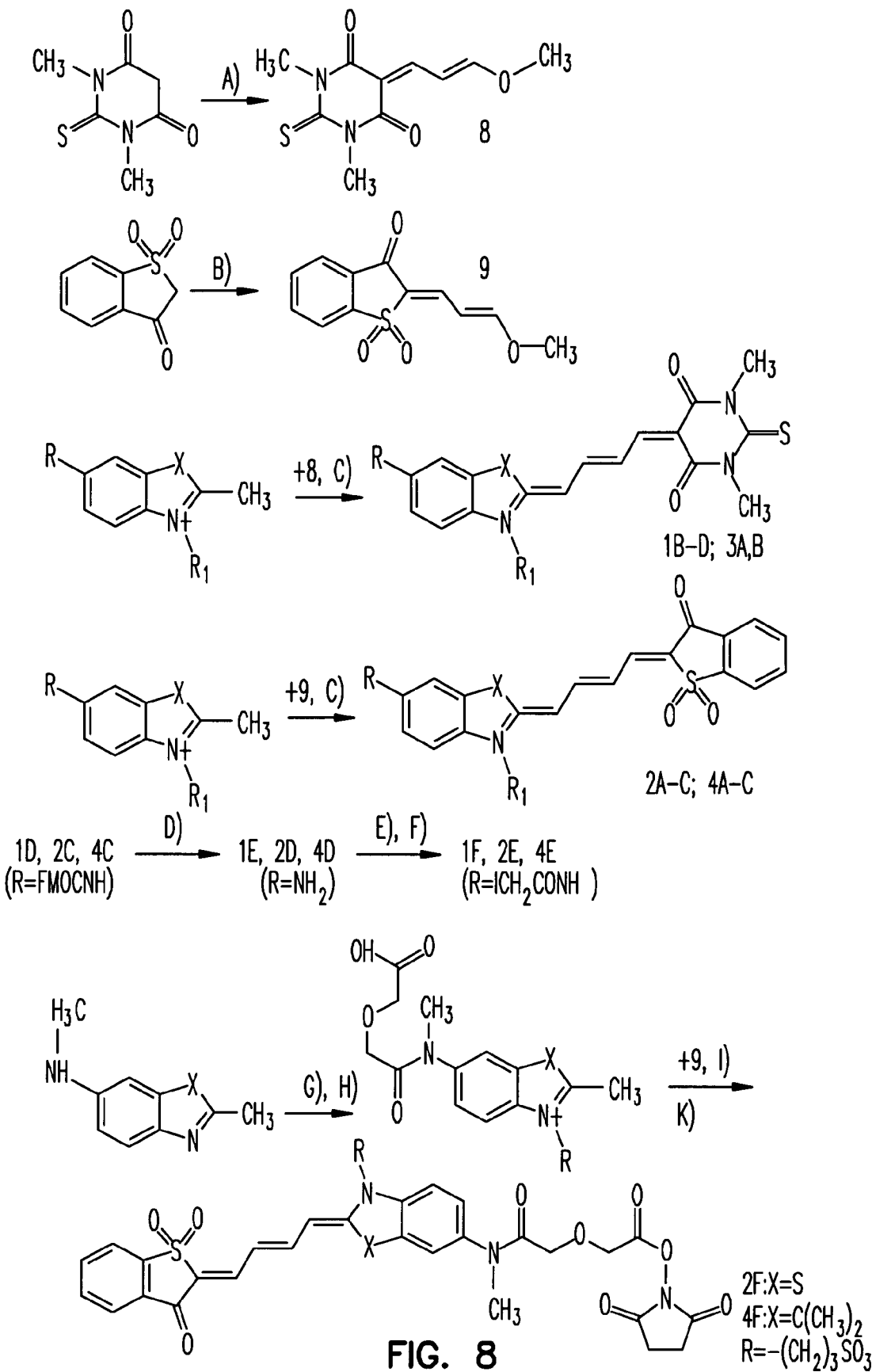
FIG. 8 illustrates a synthetic route to the dyes of the invention. Conditions for the following steps were as follows: (a) 1,3,3-trimethoxypropene, methanol (MEOH), reflux. (b) 1,3,3-trimethoxypropene, 90° C. (c) sodium acetate(AcONa), MeOH—$CHCl_3$, reflux. (d) AcONa, dimethylsulfoxide (DMSO) 100° C. (e) $ClCH_2COCl$/$Et_3N$, dimethylformamide (DMF),–40° C. (f) NaJ, MeOH, reflux. (g) Diglycolic anhydride, $CHCl_3$,reflux. (h) propanesulfone, $C_6H_6$, 75° C. (i) AcONa, acetic acid (AcOH), 80° C. (k) O—(N-Succinimidyl)-1,1,3,3-tetramethyl uranium tetrafluoroborate) (TSTU) diisopropylethylamine (($i$-$Pf$)$_2$EtN), DMF, room temperature (rt). Further description of the synthesis of these compounds is provided in Example 1.

These compounds can be synthesized, e.g., as shown in FIG. 8. A description of the materials and methods used for synthesis can be found in the Examples.

The environmentally-sensitive dyes of the invention can be many times brighter than other dyes used previously to study antibody-antigen and other protein-protein interactions in vitro. See Renard, M., Belkadi, L. & Bedouelle, H. Deriving Topological Constraints from Functional Data for the Design of Reagentless Fluorescent Immunosensors; *J Mol Biol* 326, 167-175 (2003); Sloan, D. J. & Hellinga, H. W. Structure-based Engineering of Environmentally Sensitive Fluorophores for Monitoring Protein-protein Interactions. *Protein Eng* 11, 819-823 (1998); Iwatani, S., Iwane, A. H., Higuchi, H., Ishii, Y. & Yanagida, T. Mechanical and Chemical Properties of Cysteine-modified Kinesin Molecules. *Biochemistry* 38, 10318-10323 (1999).

The quantum yield for many of the environmentally sensitive dyes of the invention are very high, e.g., in hydrophobic environments. For example, for many of the present dyes in a hydrophobic environment or solvent, the quantum yield is greater than about 0.4, or about 0.5, or about 0.6, or about 0.7, or about 0.80. In some embodiments, the dyes of the invention have a quantum yield that is greater than about 0.90. The I—SO dye, having formula 4, can have a quantum yield of about 0.97 with an extinction coefficient of about 143,000 in dimethylformamide. Such a high extinction coefficient and quantum yield can provide, e.g., strong direct signals from biosensors of the invention. These high quantum yields and extinction coefficients can allow detections from very small amounts of biosensor, minimally perturbing the biological activity of the endogenous proteins being studied, and enabling high resolution kinetic studies by obtaining many images before photo-bleaching.

Use of biosensors with environmentally-sensitive dyes can provide important advantages over currently available affinity probe schemes, such as those that involve imaging antibodies labeled with non-environmentally sensitive dyes. See, Nizak, C. et al. *Science* 300, 984-987 (2003). For example, a change in fluorescence intensity or wavelength of emission can be quantified in near real time, as compared to visualization of target retrospectively by radioactive or ELISA formats. In many cases the fleeting presence of target cannot be observed by methods with delayed detection.

In another aspect, two or more dyes with different emissions wavelengths can be employed to enable imaging of multiple protein activities in the same cell, e.g., at the same time. The biosensors of the invention typically include one or more fluorophores in order to facilitate detection of a binding event, e.g. using ratiometric measurements. While a single dye is preferred, in some cases, it may be desirable to provide more than one dye molecule on the binding domain of the biosensor to facilitate monitoring of a binding event.

The unique dyes in biosensors of the invention can be linked to binding domains and/or targets. In the case of biosensors consisting of a target molecule of interest, the environmentally sensitive dyes of the invention can be linked to the target at a position that changes a signal from the dye on, e.g., changes to the target conformation, ligand binding to the target, protein-protein interactions with the target, phosphorylation of the target, or posttranslational modification of the target. The environmentally sensitive dyes of the invention can be linked to the target of interest in biosensors using the techniques of dye linkage discussed below in the Conjugation of Dyes to Binding Domains section below. Preferred positions for linkage, to provide, e.g., improved signal intensity or minimal perturbation of normal biological activity, can be identified using screening techniques discussed herein, such as in the Conjugation of Dyes to Binding Domains section below.

Binding Domains

The invention provides biosensors that include a binding domain and an environmentally sensitive dye. Binding domains of the invention can include any molecules that bind to a target molecule with suitable specificity. Binding domains of the invention are typically binding regions of affinity molecules known in the biological sciences including, but not limited to, antibodies, antibody fragments, leucine zippers, histones, enhancers, complementary determining regions (CDRs), to single chain variable fragments (scFv's), receptors, ligands, aptamers, lectins and one of several proteins in a protein complex or a protein pair. Binding domains can simply comprise, e.g., either member of a pair of proteins in a protein-protein interaction; the "binding domain" member being identified, e.g., as the member introduced into an assay system to probe for a target of interest. Binding domains of the invention can be binding regions of, e.g., full sized versions of the affinity molecule, fragments of the affinity molecule, or the smallest portion of the affinity molecule providing binding useful in the detection of a target of interest. In many embodiments, the binding domains can have specific affinity to endogenous (e.g., constitutive or inducible, but not recombinant) peptides of a cell. This is an important advantage.

Biosensors of the invention are diverse in their intended target and detection schemes. Biosensors of the invention can be designed with binding domains that bind only to a particular state of a targeted protein. When the biosensor binds to the target a fluorescence change can be signaled to reveal, for example, the level and/or location of protein in the targeted state. Changes over time can be monitored. Biosensors can incorporate binding domains of naturally occurring protein domains with specific binding activity. The binding domains can optionally be, for example, full length affinity proteins, members of protein-protein interaction pairs (or portions thereof), Fv antibody fragments, aptamers, Vh antibody fragments, etc. Signals from the biosensors can depend on FRET systems or, preferably employ a single environmentally-sensitive dye. Single chain variable fragment (scFv) binding domains can be particularly useful in modular biosensors of the invention in which binding domain and/or target modules connected with a linker can be replaced with alternate versions to provide new desired specificities to the sensor. In another preferred aspect, scFvs can be combined with environmentally sensitive dyes of the invention for novel methods of probing living cells.

The invention can involve attachment of the dye to all or part of a protein of interest, e.g., that is subject to changed phosphorylation states and/or protein-ligand interactions, where the ligand can be a small molecule or a second protein. This can provide a relatively simple biosensor type using the dyes of the invention. Dyes of the invention can be covalently attached to the protein of interest to provide a signal associated with the phosphorylation state and/or protein-protein interaction. This type of detection is in contrast to previously described detections (Hahn et al., Solvent-sensitive Dyes to Report Protein Conformational Changes in Living Cells, J Am Chem Soc 125, 4132-4145 (2003)) wherein the biosensors detect a conformational change in the target protein induced by the action of a third element. For example, in Hahn, K. M. et al., J. Biol. Chem. 265, pp 20335-20345, (1990), a conformational change is induced by calcium in a calmodulin target and detectable as a signal from an attached dye. In the present invention, detection is extended to conformational changes induced by phosphorylation, and does not necessarily require induction of a conformational change in the protein of interest. In one embodiment, a dye was attached to the MAP kinase ERK2. Upon phosphorylation-induced conformational change of ERK2, a covalently attached dye underwent a conformational change. An important advantage of this technique is that proteins within multiprotein complexes can be monitored in situations where other types of biosensors, foe example, those requiring a domain to find the target protein, would be blocked. Environmentally sensitive dyes of the invention are particularly well suited to such biosensor applications. Previous dyes were not suitable for many proteins as they were insoluble except in high percentage aqueous organic solvents. Furthermore, dyes of the invention can allow detections from a single dye, e.g., without the use of two fluorophores, as in FRET, to provide direct excitation and a brighter signal.

Binding domains can comprise polypeptide or nucleic acid sequences. For example, binding domains can be single stranded DNA (sDNA), double stranded DNA (dsDNA), RNA, nucleic acids with modified bases, and the like. In one embodiment, the binding domain is an oligonucleotide probe and the target is a complimentary target nucleic acid. In another embodiment, the binding domain is a dsDNA strand specific to a target enhancer protein target. Environmentally sensitive dyes of the invention can be linked to nucleic acids, by any technique known in the art, such as by reaction of linker groups on the dye to reactive groups available on modified bases on the nucleic acid.

In some preferred embodiments, the binding domain comprises a polypeptide or peptide sequence. Affinity specificity of peptide binding domains can be provided by a short sequence of amino acids (e.g., 3 to 20 residues), or the specificity can rely on contributions of amino acid side chains brought in proximity by the primary, secondary, tertiary, and/or quaternary structural conformations of one or more affinity proteins. Binding domains made from peptides can have can have natural amino acid side chains, modified side chains, or the like that provide reactive groups specifically reactive with linkers on dyes of the invention. Alternately, the dye of the invention can have reactive groups specifically reactive with linker groups present on the binding domain to link the dye to the domain. The position of a dye on a domain can be determined by the location of a reactive group or linker moiety on the domain, as will be discussed further below. In some embodiments, the binding domain has one or more cysteine residues reactive with groups on the dyes, for example, iodoacetamido groups on the dyes. In a common embodiment of the invention, the biosensors comprise binding domains which are members of the immunoglobulin family of proteins, or derivatives thereof. For example, the binding domain can be a complete immunoglobulin, fragment, single chain variable fragment (scFv), a heavy or light chain variable region, a CDR peptide sequence, and/or the like.

Antibody molecules belong to a family of plasma and cell surface proteins called immunoglobulins, whose basic building block, the immunoglobulin fold or domain, is used in various forms in many molecules of the immune system and other biological recognition systems. A standard antibody is a tetrameric structure consisting of two identical immunoglobulin heavy chains and two identical light chains and has a molecular weight of about 150,000 Daltons.

The heavy and light chains of an antibody consist of different domains. Each light chain has one variable domain (VL) and one constant domain (CL), while each heavy chain has one variable domain (VH) and three or four constant domains (CH). See, e.g., Alzari, P. N., Lascombe, M.-B. & Poljak, R. J. (1988) *Three-dimensional structure of antibodies*. Annu. Rev. Immunol. 6, 555-580. Each domain, consisting of about 110 amino acid residues, is folded into a characteristic β-sandwich structure formed from two β-sheets packed against each other, the immunoglobulin fold. The VH and VL domains each have three complementarity determining regions (CDR1-3) that are loops, or turns, connecting β-strands at one end of the domains. The variable regions of both the light and heavy chains generally contribute to antigen specificity, although the contribution of the individual chains to specificity is not always equal. Antibody molecules have evolved to bind to a large number of molecules through these six randomized loops (CDRs).

Immunoglobulins can be assigned to different classes depending on the amino acid sequences of the constant domain of their heavy chains. There are at least five (5) major classes of immunoglobulins: IgA, IgD, IgE, IgG and IgM. Several of these may be further divided into subclasses (isotypes), for example, IgG-1, IgG-2, IgG-3 and IgG-4; IgA-1 and IgA-2. The heavy chain constant domains that correspond to the IgA, IgD, IgE, IgG and IgM classes of immunoglobulins are called alpha (α), delta (δ), epsilon (ε), gamma (γ) and mu (μ), respectively. The light chains of antibodies can be assigned to one of two clearly distinct types, called kappa (κ) and lambda (λ), based on the amino sequences of their constant domain. The subunit structures and three-dimensional configurations of different classes of immunoglobulins are well known.

The term "variable" in the context of variable domain of antibodies, refers to the fact that certain portions of variable domains differ extensively in sequence from one antibody to the next. The variable domains are for binding and determine the specificity of each particular antibody for its particular antigen. However, the variability is not evenly distributed through the variable domains of antibodies. Instead, the variability is concentrated in three segments called complementarity determining regions (CDRs), also known as hypervariable regions in both the light chain and the heavy chain variable domains.

The more highly conserved portions of variable domains are called framework (FR) regions. The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FR regions and, with the CDRs from another chain, contribute to the formation of the antigen-binding site of antibodies.

An antibody that is contemplated for use in the present invention thus can be in any of a variety of forms, including a whole immunoglobulin, an antibody fragment such as Fv, Fab, and similar fragments, a single chain antibody which includes the variable domain complementarity determining regions (CDR), and the like forms, all of which fall under the broad term "antibody", as used herein. The present invention contemplates the use of any specificity of an antibody, polyclonal or monoclonal. In many embodiments, in the context of methods described herein, an antibody, or fragment thereof is used that is immunospecific for a selected target.

The term "antibody fragment" refers to a portion of a full-length antibody, generally the antigen binding or variable region. Examples of antibody fragments include Fab, Fab', F(ab')$_2$ and Fv fragments. Papain digestion of antibodies produces two identical antigen binding fragments, called Fab fragments, each with a single antigen binding site, and a residual Fc fragment. Fab fragments thus have an intact light chain and a portion of one heavy chain. Pepsin treatment yields an F(ab')$_2$ fragment that has two antigen binding fragments that are capable of cross-linking antigen, and a residual fragment that is termed a pFc' fragment. Fab' fragments are obtained after reduction of a pepsin digested antibody, and consist of an intact light chain and a portion of the heavy chain. Two Fab' fragments are obtained per antibody molecule. Fab' fragments differ from Fab fragments by the addition of a few residues at the carboxyl terminus of the heavy chain CH1 domain including one or more cysteines from the antibody hinge region.

Fv is a small antibody fragment that contains a complete antigen recognition and binding site. This region consists of a dimer of one heavy and one light chain variable domain in a tight, non-covalent association ($V_H$-$V_L$ dimer). It is in this configuration that the three CDRs of each variable domain interact to define an antigen binding site on the surface of the $V_H$-$V_L$ dimer. Collectively, the six CDRs confer antigen binding specificity to the antibody. However, even a single variable domain (or half of an Fv comprising only three CDRs specific for an antigen) has the ability to recognize and bind antigen, although at a lower affinity than the entire binding site. Antibody fragments usefully incorporated into biosensors of the invention can include, e.g., single CDRs, $V_H$ regions, $V_L$ regions, Fv fragments, F(ab) and F(ab')$_2$ fragments Additional fragments can include diabodies, linear antibodies, single-chain antibody molecules, and multispecific antibodies formed from antibody fragments. Antibody fragments used in binding domains of the invention can include, e.g., natural, synthetic, or recombinant versions. Single chain antibodies are genetically engineered molecules containing the variable region of a light chain and a variable region of the heavy chain, linked by a suitable polypeptide linker as a genetically fused single chain molecule. Such single chain antibodies are also referred to as "single-chain Fv" or "scFv" antibody fragments. Generally, the Fv polypeptide further comprises a polypeptide linker between the VH and VL domains that enables the scFv to form the desired structure for antigen binding. For a review of scFv see Pluckthun in The Pharmacology of Monoclonal Antibodies, vol. 113, Rosenburg and Moore eds. Springer-Verlag, N.Y., pp. 269-315 (1994).

In some embodiments of the invention, any antibody or antibody fragment can be used in a binding domain to which dyes can be attached to form a biosensor. In one embodiment, single chain variable fragments are used as binding domains. Any available scFv can be used so long as it binds to a selected target with sufficient affinity to permit detection of a complex formed between the scFv and the selected target. A fluorescent dye can be attached to the selected scFv at any convenient site. However, as described herein, the fluorescence of the attached dye can be influenced by its attachment position. For example, the highest fluorescence responses for the S—SO or I—SO fluorescent dyes having structures 2 and 4, respectively, were obtained from three positions in the CDR3 loop of the heavy chain (H96, H100H, H100E), with conjugation at position H96 giving an almost 6-fold increase (FIG.

11C). It is an aspect of the invention that the environmentally sensitive dye can have a detectable change in signal of, e.g., 50%, 100%, 200%, 500%, 1000%, or more.

Hence, the invention provides scFv molecules with convenient attachment sites for dyes. One scFv X5 light chain that can be employed in the methods of the invention has the following sequence (SEQ ID NO: 1), or conservative substitutions thereof, where each X represents a separate variable or CDR amino acid, n is an integer between about 3 and about 25 and wherein one or more X amino acid can be any linker reactive group, such as a cysteine or derivatized amino acid, that provides an attachment site for a fluorescent dye. In some embodiments, an additional attachment site can be provided by including a threonine-cysteine-threonine (TCT) sequence at the N-terminus. SEQ ID NO: 1 is shown below.

```
LTQSPGTLSLSAGERATLSC (X)ₙWYQQKPGQAPRLLIY (X)ₙGIPDR
FSGSGSGTDFTLTIGRLEPEDLAVYYC (X)ₙ
```

One scFv X5 heavy chain that can be employed in the methods of the invention has the following sequence (SEQ ID NO: 2), or conservative substitutions thereof, where each X represents a separate variable or CDR amino acid, n is an integer between about 3 and about 25 and wherein one or more X amino acid can be a linker reactive group that provides an attachment site for a fluorescent dye.

```
QVQ LVQSGAEVKK PGSSVQVSCK ASGGTF(X)ₙWVR
    QAPGHGLEWM G (X)ₙRVTFTADQ ATSTAYMELT
    NLRSDDTAVY YCAR (X)ₙWGQGT LVTVSSPRGPAGQ
```

In one embodiment, one or two dye molecules are attached to one or two linker reactive residues within the CDR3 region of the scFv heavy chain. For example, the dye(s) can be attached at about position 95 to about position 105. In many embodiments, just one dye molecule is attached to the scFv heavy chain at a residue falling within the CDR3 region of the scFv, for example, at about position 95 to about position 105.

The residue to which the dye is attached is preferably a cysteine. A linker can be employed to associate the affinity sequences in binding domains of the invention. The linker is preferably a flexible chain-like structure such as an aliphatic chain or a polymer. In more preferred embodiments, the linker is a peptide or nucleic acid with significant hydrophilic character. An exemplary peptide sequence for linking a light and heavy chains is provided in (SEQ ID NO: 3): GGGGSGGGGSGGGGSRSS.

Hence, the invention provides a scFv binding domain having the following sequence (SEQ ID NO: 4), or conservative substitutions thereof:

```
LTQSPGTLSL SAGERATLSC (X)ₙWYQQKPGQA
PRLLIY(X)ₙGIPD RFSGSGSGTD FTLTIGRLEP
EDLAVYYC(X)ₙG GGGSGGGGSG GGGSRSS
QVQLVQSGAE VKKPGSSVQV SCKASGGTF(X)ₙ
WVRQAPGHGL EWMG(X)ₙRVTFT ADQATSTAYM
ELTNLRSDDT AVYYCAR(X)ₙWG QGTLVTVSSP
RGPAGQ
``` where each X represents a separate variable or CDR amino acid, n is an integer between about 3 and about 25, and wherein one or more X amino acid can be a linker reactive group, such as a cysteine or amino acid derivative, that provides an attachment site for a fluorescent dye.

As described herein, the scFv X5 light chain employed for imaging HIV interactions with host cells had the following sequence (SEQ ID NO:5), where the residues that were mutated to provide dye attachment sites are identified in bold and by underlining.

```
 1 TCT LTQSPGTLSL SAGERATLSC RASQSVSSGS LAWYQQKPGQ
44     APRLLIYGAS TRATGIPDRF SGSGSGTDFT LTIGRLEPED
84     LAVYYCQQYG TSPYTFGQGT KVDIKR
```

The present invention includes binding domains containing peptides with the sequence of SEQ ID NO: 5, and conservative substitutions thereof; including sequences modified to provide linker reactive residues at locations adapted to provide suitable binding and signals after linkage of environmentally sensitive dyes of the invention. The TCT sequence at the N-terminus was added and is not a natural part of the X5 antibody. The CDR regions of this X5 light chain can include the following peptidyl sequences RASQSVSSGSLA (SEQ ID NO: 6), GASTRAT (SEQ ID NO: 7) and QQYGTSPYTFGQGTKVDIKR (SEQ ID NO: 8). Upon mutation of the residues indicated above for SEQ ID NO:5 to cysteine, one or more of these CDR regions can have the following sequences: RASQSVSSGCLA (SEQ ID NO: 9), GASCRAT (SEQ ID NO: 10) or QQYGTSPCTFGQGTKVDIKR (SEQ ID NO: 11). In other embodiments, one or more such residues can include linker reactive groups other than cysteine.

A scFv X5 heavy chain binding domain can include following sequence (SEQ ID NO: 12), or conservative variations thereof, where the residues that were mutated are identified in bold and by underlining.

```
  1 QVQ LVQSGAEVKK PGSSVQVSCK ASGGTFSMYG FNWVRQAPGH
 44     GLEWMGGIIP IFGTSNYAQK FRGRVTFTAD QATSTAYMEL
 84     TNLRSDDTAV YYCARDFGPD WEDGDSYDGS GRGFFDFWGQ
124 GTLVTVSSPR GPAGQ
```

The CDR regions of this X5 light chain can include the following peptidyl sequences SMYGFN (SEQ ID NO: 13), GIIPIFGTSNYAQKFRG (SEQ ID NO: 14) and DFGPDWEDGDSYDGSGRGFFDF (SEQ ID NO: 15), and conservative variations thereof. Upon mutation of the indicated residues to cysteine, one or more of these CDR regions had the following sequences: SMYGCN (SEQ ID NO: 16), GIIPCFGTSNYAQKFRG (SEQ ID NO: 17), GIIPIFGTSNYAQKFCG (SEQ ID NO: 18), DCGPDWEDGDSYDGSGRGFFDF (SEQ ID NO: 19), DFGPDWEDCDSYDGSGRGFFDF (SEQ ID NO: 20), DFGPDWEDGDCYDGSGRGFFDF (SEQ ID NO: 21) or DFGPDWEDGDSYDCSGRGFFDF (SEQ ID NO: 22). The present invention includes these peptide sequences, conservative substitutions thereof, and/or replacement of one or more cysteine with other linker reactive groups.

A linker chain, as described above can be employed to link the light and heavy chains together. For example the linker can be a peptide with the sequence of SEQ ID NO: 3.

"Conservative amino acid substitutions", in a peptide can include substitution of one or a few amino acids with different amino acids having substantially similar properties to provide a functional peptide. Similarly, owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Such conservative variations of each disclosed sequence are a feature of the present invention.

"Conservative variations" of a particular nucleic acid sequence refers to those nucleic acids which encode identical or essentially identical amino acid sequences (see, Table 1 below). One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence or sequences with accessory functions, are conservative variations of the basic nucleic acid.

TABLE 1

Conservative Substitution Groups

| | | | |
|---|---|---|---|
| Alanine (A) | Serine (S) | Threonine (T) | |
| Aspartic acid (D) | Glutamic acid (E) | | |
| Asparagine (N) | Glutamine (Q) | | |
| Arginine (R) | Lysine (K) | | |
| Isoleucine (I) | Leucine (L) | Methionine (M) | Valine (V) |
| Phenylalanine (F) | Tyrosine (Y) | Trytophan (W) | |

In Table 1, substitution of an amino acid with another amino acid of the same group (i.e., in the same row) can be considered a conservative substitution.

The light X5 chain was encoded by the following nucleic acid (SEQ ID NO: 23), conservative variations thereof, or unique subsequences thereof. In a preferred embodiment of the invention, the nucleotides indicated in bold and with underlining can be mutated to encode alternate amino acid residues, e.g., capable of linkage reactions with dyes of the invention. Optionally, amino acids encoded with codons in bold and with underlining be replaced with linker reactive groups.

```
  1 GCTACCGTGG CCCAGGCGGC CGAGCGCGAT ATTGTGCTGA
 41 CGCAGTCTCC AGGCACCCTG TCTTTGTCTG CAGGGGAAAG
 81 AGCCACCCTC TCCTGCAGGG CCAGTCAGAG TGTTAGCAGC
121 GGCTCCTTAG CCTGGTACCA GCAGAAACCT GGTCAGGCTC
161 CCAGGCTCCT CATCTACGGT GGATCCACCA GGGCCACTGG
201 CATCCAGAC AGGTTCAGTG GCAGTGGGTC TGGGACAGAC
```

-continued
```
241 TTCACTCTCA CAATCGGCAG ACTGGAGCCT GAAGATCTCG
281 CAGTATATTA CTGTCAGCAG TATGGTACCT CACCGTACAC
321 TTTTGGCCAG GGGACCAAAG TGGATATCAA ACGT
```

The heavy X5 chain was encoded by the following nucleic acid sequence (SEQ ID NO: 24), where the nucleotides encoding the residues to be mutated are indicated in bold and with underlining. The present invention includes SEQ ID NO: 24, conservative variations thereof, or unique subsequences thereof. In a preferred embodiment of the invention, the nucleotides indicated in bold and with underlining can be mutated to encode alternate amino acid residues, e.g., capable of linkage reactions with dyes of the invention. Optionally, amino acids encoded with codons in bold and with underlining be replaced with linker reactive groups.

```
  1 TCCCAGGTCC AGCTTGTGCA GTCTGGGGCT GAGGTGAAGA
 41 AGCCTGGGTC CTCGGTGCAG GTCTCCTGCA AGGCCTCTGG
 81 AGGCACCTTC AGCATGTATG GTTTCAACTG GGTGCGACAG
121 GCCCCTGGAC ATGGCCTTGA GTGGATGGGA GGGATCATCC
161 CTATCTTTGG TACATCAAAC TACGCACAGA AGTTCCGGGG
201 CAGAGTCACG TTTACCGCGG ACCAAGCCAC GAGCACAGCC
241 TACATGGAGC TGACCAACCT GCGATCTGAC GACACGGCCG
281 TCTATTATTG TGCGAGAGAT TTTGGCCCCG ACTGGGAAGA
321 CGGTGATTCC TATGATGGTA GTGGCCGGGG GTTCTTTGAC
361 TTCTGGGGCC AGGGAACCCT GGTCACCGTC TCCTCACCTC
401 GTGGGCCGGC CGGGCAG
```

A linker can be employed to attach heavy and light chains described above. The linker can be, e.g., an aliphatic chain or polymer; preferably a peptide with substantial hydrophilic character. An exemplary linker sequence of the invention is encoded by SEQ ID NO: 25, below, and conservative variations thereof.

```
  1 GGTGGCGGTG GCTCGGGCGG TGGCGGTTCA GGTGGCGGTG
 41 GCTCTAGATC T
```

Based on sequence data and the crystal structure of binding domains one or more dyes of the invention can be attached to provide preferred biosensors of the invention. For example, based on the sequence data and the crystal structure of a free Fab fragment, several merocyanine dyes can be attached to a series of one or more different residue positions to create a small but intelligently designed library of biosensor candidates. The resultant library could be screened, as can be appreciated by those in the art, to identify candidates with desired properties, e.g., of signal strength and binding affinity.

In a typical embodiment, the selected residues can be changed to cysteine residues using the following changes or mutations in scFv nucleotide sequence:

```
Cys Mutations: TCC -> TGC, ACC -> TGC, TAC -> TGC,
               TTC -> TGC, ATC -> TGC, CGG -> TGT,
               TTT -> TGT, TCC -> TGC, GGT -> TGT
```

Optionally, selected residues can be mutated to other amino acids useful in linkage chemistries, as discussed above. Furthermore, selected residues can optionally be replaced with other linker reactive moieties, such as unnatural amino acids or derivatized amino acids.

Antibody fragments contemplated by the invention are not necessarily full-length antibodies. However, such antibody fragments can have similar or improved immunological or other properties relative to a full-length antibody. For example, such antibody fragments can be smaller and more stable than full-length antibodies. Such antibody fragments can include about 4 amino acids, 5 amino acids, 6 amino acids, 7 amino acids, 9 amino acids, about 12 amino acids, about 15 amino acids, about 17 amino acids, about 18 amino acids, about 20 amino acids, about 25 amino acids, about 30 amino acids, or more.

In general, an antibody fragment of the invention can have any upper size limit so long as it is has similar or improved properties relative to an antibody that binds with specificity to a desired target molecule. For example, smaller antibody fragments can have less than about 200 amino acids, less than about 175 amino acids, less than about 150 amino acids, or less than about 120 amino acids if the antibody fragment is related to a light chain antibody subunit. Moreover, larger antibody fragments can have less than about 425 amino acids, less than about 400 amino acids, less than about 375 amino acids, less than about 350 amino acids, less than about 325 amino acids or less than about 300 amino acids if the antibody fragment is related to a heavy chain antibody subunit.

Antibodies and antibody fragments directed against selected targets can be prepared by techniques commonly known in the art. In some embodiments, antibody fragments can be prepared from full-length antibodies. Methods for the preparation of polyclonal antibodies are available to those skilled in the art. See, for example, Green, et al., Production of Polyclonal Antisera, in: *Immunochemical Protocols* (Manson, ed.), pages 1-5 (Humana Press); Coligan, et al., Production of Polyclonal Antisera in Rabbits, Rats Mice and Hamsters, in: *Current Protocols in Immunology*, section 2.4.1 (1992), which are hereby incorporated by reference. Such polyclonal antibodies can be cleaved, e.g., by chemical or enzymatic treatment to prepare antibody fragments useful in the present invention.

Monoclonal antibodies, and fragments thereof, can also be employed in the invention. The term "monoclonal antibody" as used herein refers to an antibody obtained from a population of substantially homogeneous antibodies. In other words, the individual antibodies comprising the population are identical except for occasional naturally occurring mutations in some antibodies that may be present in minor amounts. Monoclonal antibodies are highly specific, being directed against a single antigenic site. Furthermore, in contrast to polyclonal antibody preparations that typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody indicates the character of the antibody as being obtained from a substantially homogeneous population of antibodies, and is not to be construed as requiring production of the antibody by any particular method.

The monoclonal antibodies herein specifically include "chimeric" antibodies in which a portion of the heavy and/or light chain is identical or homologous to corresponding sequences in antibodies derived from a particular species or belonging to a particular antibody class or subclass, while the remainder of the chain(s) are identical or homologous to corresponding sequences in antibodies derived from another species or belonging to another antibody class or subclass. Fragments of such antibodies can also be used, so long as they exhibit the desired biological activity. See U.S. Pat. No. 4,816,567; Morrison et al. Proc. Natl. Acad Sci. 81, 6851-55 (1984).

The preparation of monoclonal antibodies likewise is conventional. See, for example, Kohler & Milstein, Nature, 256: 495 (1975); Coligan, et al., sections 2.5.1-2.6.7; and Harlow, et al., in: *Antibodies: A Laboratory Manual*, page 726 (Cold Spring Harbor Pub. (1988)), which are hereby incorporated by reference. Monoclonal antibodies can be isolated and purified from hybridoma cultures by a variety of well-established techniques. Such isolation techniques include affinity chromatography with Protein-A Sepharose, size-exclusion chromatography, and ion-exchange chromatography. See, e.g., Coligan, et al., sections 2.7.1-2.7.12 and sections 2.9.1-2.9.3; Barnes, et al., Purification of Immunoglobulin G (IgG), in: *Methods in Molecular Biology*, Vol. 10, pages 79-104 (Humana Press (1992).

Methods of in vitro and in vivo manipulation of antibodies are available to those skilled in the art. For example, the monoclonal antibodies to be used in accordance with the present invention may be made by the hybridoma method as described above or may be made by recombinant methods, e.g., as described in U.S. Pat. No. 4,816,567. Monoclonal antibodies for use with the present invention may also be isolated from phage antibody libraries using the techniques described in Clackson et al. Nature 352: 624-628 (1991), as well as in Marks et al., J. Mol Biol. 222: 581-597 (1991).

Methods of making antibody fragments are also known in the art (see for example, Harlow and Lane, *Antibodies: A Laboratory Manual*, Cold Spring Harbor Laboratory, New York, (1988), incorporated herein by reference). Antibody fragments of the present invention can be prepared by proteolytic hydrolysis of the antibody or by expression of nucleic acids encoding the antibody fragment in a suitable host: Antibody fragments can be obtained by pepsin or papain digestion of whole antibodies conventional methods. For example, antibody fragments can be produced by enzymatic cleavage of antibodies with pepsin to provide a 5S fragment described as $F(ab')_2$. This fragment can be further cleaved using a thiol reducing agent, and optionally using a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. These methods are described, for example, in U.S. Pat. Nos. 4,036,945 and 4,331,647, and references contained therein. These patents are hereby incorporated by reference in their entireties.

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody. For example, Fv fragments comprise an association of $V_H$ and $V_L$ chains. This association may be noncovalent or the variable chains can be linked by an intermolecular disulfide bond or cross-linked by chemicals such as glutaraldehyde. Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow, et al., *Methods: a Companion to Methods in Enzymology*, Vol. 2, page 97 (1991); Bird, et al., Science 242:423-426 (1988); Ladner, et al, U.S. Pat. No. 4,946, 778; and Pack, et al., *Bio/Technology* 11:1271-77 (1993).

Another form of an antibody fragment is a peptide coding for a single complementarity-determining region (CDR). CDR peptides ("minimal recognition units") are often involved in antigen recognition and binding. CDR peptides can be obtained by cloning or constructing genes encoding the CDR of an antibody of interest. Such genes are prepared, for example, by using the polymerase chain reaction to synthesize the variable region from RNA of antibody-producing cells. See, for example, Larrick, et al., *Methods: a Companion to Methods in Enzymology*, Vol. 2, page 106 (1991).

The amino acid sequence of monoclonal antibodies, polyclonal antibodies, fragments thereof, and such, can be determined by amino acid sequencing methods known in the invention. Amino acid sequences of antibodies and fragments of interest can evaluated for binding sequences, such as, e.g., CDR sequences, useful in biosensors of the invention. Sequences of interest can be directly synthesized or translated into nucleic acid sequences for manipulation by genetic engineering techniques known in the art. Amino acid and nucleic acid sequences thus obtained can be screened for binding characteristics desirable in biosensors of the invention. Optionally, sequences thus obtained can be logically modified and/or randomly mutated to generate additional binding domain candidates that can be screened to identify sequences most useful in particular biosensor systems of interest.

The invention contemplates human and humanized forms of non-human (e.g. murine) antibodies. Such humanized antibodies are chimeric immunoglobulins, immunoglobulin chains or fragments thereof (such as Fv, scFv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity.

In some instances, Fv framework residues of the human immunoglobulin can be replaced by corresponding non-human residues. Furthermore, humanized antibodies can comprise residues that are found neither in the recipient antibody nor in the imported CDR or framework sequences. These modifications can be made to further refine and optimize antibody performance. In general, humanized antibodies will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optionally can comprise at least a portion of an immunoglobulin constant region (Fc), typically that of a human immunoglobulin. For further details, see: Jones et al., Nature 321, 522-525 (1986); Reichmann et al., Nature 332, 323-329 (1988); Presta, Curr. Op. Struct. Biol. 2, 593-596 (1992); Holmes, et al., J. Immunol., 158:2192-2201 (1997) and Vaswani, et al., Annals Allergy, Asthma & Immunol., 81:105-115 (1998).

In the immune system, specific antibodies are selected and amplified from a large library (affinity maturation). The combinatorial techniques employed in immune cells can be mimicked by mutagenesis and generation of combinatorial libraries of binding entities. Variant binding entities, antibody fragments and antibodies therefore can also be generated through display-type technologies. Such display-type technologies include, for example, phage display, retroviral display, ribosomal display, yeast display and other techniques. Techniques available in the art can be used for generating libraries of binding entities, for screening those libraries and the selected binding entities can be subjected to additional maturation, such as affinity maturation. Wright and Harris, supra., Hanes and Plucthau PNAS USA 94:4937-4942 (1997) (ribosomal display), Parmley and Smith Gene 73:305-318 (1988) (phage display), Scott TIBS 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH 10:80-84 (1992), and U.S. Pat. No. 5,733,743.

The invention therefore also provides methods of mutating antibodies, CDRs or binding domains to optimize their affinity, selectivity, binding strength and/or other desirable properties. A mutant binding domain refers to an amino acid sequence variant of a selected binding domain (e.g. a CDR). In general, one or more of the amino acid residues in the mutant binding domain is different from what is present in the reference binding domain. Such mutant antibodies necessarily have less than 100% sequence identity or similarity with the reference amino acid sequence. In general, mutant binding domains have at least 75% amino acid sequence identity or similarity with the amino acid sequence of the reference binding domain. Preferably, mutant binding domains have at least 80%, more preferably at least 85%, even more preferably at least 90%, and most preferably at least 95% amino acid sequence identity or similarity with the amino acid sequence of the reference binding domain.

For example, affinity maturation using phage display can be utilized as one method for generating mutant binding domains. Affinity maturation using phage display refers to a process described in Lowman et al., Biochemistry 30(45): 10832-10838 (1991), see also Hawkins et al., J. Mol Biol. 254: 889-896 (1992). While not strictly limited to the following description, this process can be described briefly as involving mutation of several binding domains or antibody hypervariable regions at a number of different sites with the goal of generating all possible amino acid substitutions at each site. The binding domain mutants thus generated are displayed in a monovalent fashion from filamentous phage particles as fusion proteins. Fusions are generally made to the gene III product of M13. The phage expressing the various mutants can be cycled through several rounds of selection for the trait of interest, e.g. binding affinity or selectivity. The mutants of interest are isolated and sequenced. Such methods are described in more detail in U.S. Pat. Nos. 5,750,373, 6,290,957 and Cunningham, B. C. et al., EMBO J. 13(11), 2508-2515 (1994).

Therefore, in one embodiment, the invention provides methods of manipulating binding entity or antibody polypeptides or the nucleic acids encoding them to generate binding entities, antibodies and antibody fragments with improved binding properties that recognize selected targets.

Such methods of mutating portions of an existing binding entity or antibody involve fusing a nucleic acid encoding a polypeptide that encodes a binding domain to a nucleic acid encoding a phage coat protein to generate a recombinant nucleic acid encoding a fusion protein, mutating the recombinant nucleic acid encoding the fusion protein to generate a mutant nucleic acid encoding a mutant fusion protein, expressing the mutant fusion protein on the surface of a phage, and selecting phage that bind to a target.

Accordingly, the invention provides antibodies, antibody fragments, and binding entity polypeptides that can recognize and bind to selected target molecules. The invention further provides methods of manipulating those antibodies, antibody fragments, and binding entity polypeptides to optimize their binding properties or other desirable properties (e.g., stability, size, ease of use).

Figure 14A:
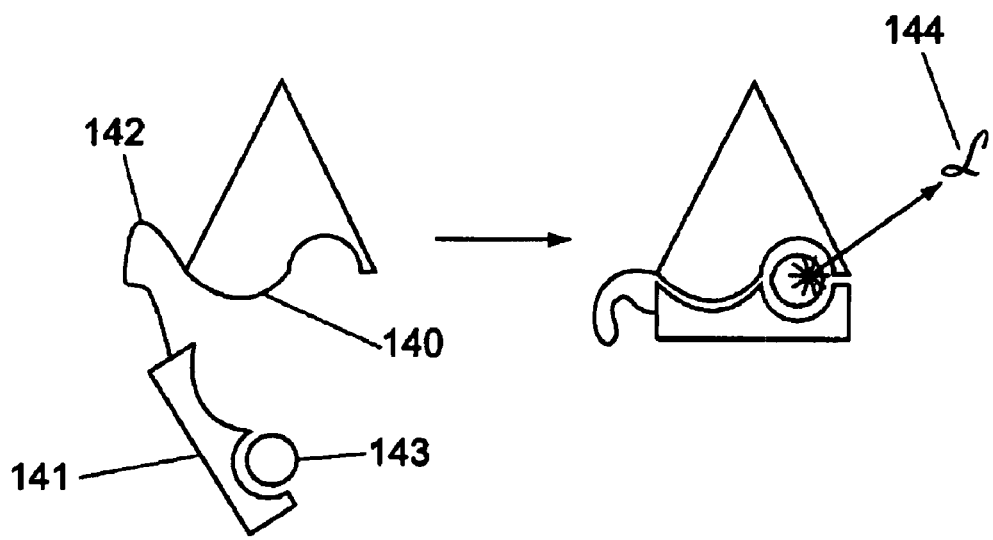
Figure 14B:
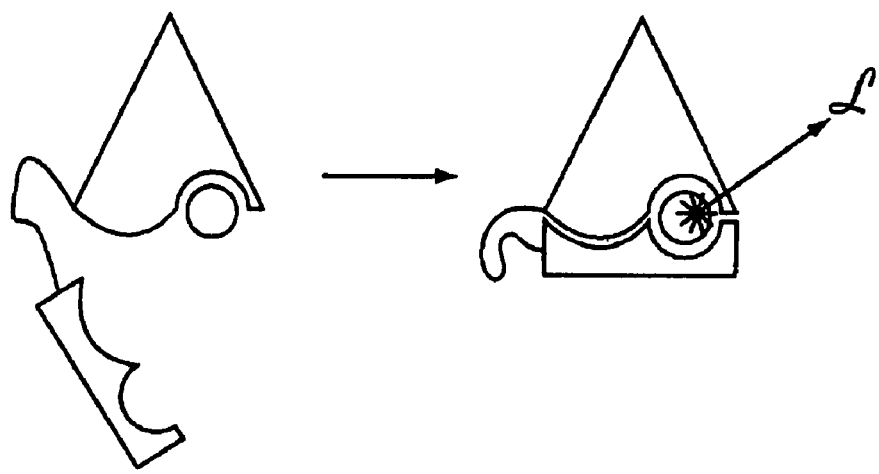
Figure 14C:
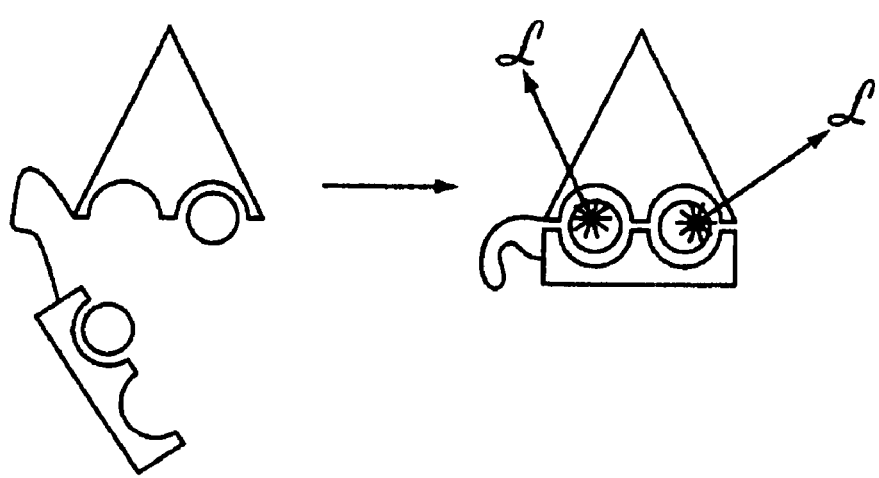

Modular biosensors are an aspect of the invention. Modular biosensors are sensors of unified design that allow certain components to be changed, e.g., to change the target specificity and/or signal character. Modular biosensors typically provide for convenient alteration of binding domain specificity. For example, an affinity molecule can be expressed from a recombinant expression construct, such as an expression vector. The affinity molecule, including binding domain 140 can optionally be expressed in a single peptide chain with linker chain 142 and target molecule 141 (typically a peptide), as shown in FIG. 14. The genetic construct can include unique endonuclease sites bracketing the region encoding the binding domain so that alternate binding domains can be readily inserted into the construct for expression as part of a biosensor. The modular binding domains can be selected, e.g., from a library of binding domains. Optionally, the modules can be encoded scFv domains. The modular systems can include affinity molecules with alternate binding domain sites, alternate dye linkage sites, alternate dye linkage reactive molecules, alternate linked targets, alternate linkers, and/or the like. Alternately, the binding domain can be of broad specificity, and the target domain (i.e. different kinase consensus sequence peptides) can be switched in the modular design.

Conjugation of Dyes to Binding Domains

Dyes of the invention can be linked to binding domains or proteins to prepare biosensors of the invention. In a typical embodiment, the binding domain includes one or more linker reactive group and the dye includes a linker group allowing linkage by simply contacting the binding domain and dye in solution. Alternately, the dye includes the linker reactive group and the binding domain includes the linker group. In another alternative, both the domain and dye include linker reactive groups, and linkage is through a bivalent linker group.

Linker reactive groups can include any chemical groups that react with selected linkers to form one or more chemical bonds. For example, natural amino acids, modified or derivatized amino acids, and/or other residues in a binding domain can provide linker reactive groups, such as amines, sulfhydryls, carboxylic acids, alcohols, aldehydes, and thiols, that can covalently bond to commercially available bivalent linker molecules. Optionally, as described above, linker reactive groups can be provided on dye molecules of the invention.

Linkers can be any type suitable to react with available linker reactive groups in linkage of binding domains of the invention to dyes of the invention. Commercially available linker groups include, e.g., hydroxysuccinimide linkers (reactive with primary amines), maleimides, haloacetyls (e.g., iodoacetamido groups), pyridyl disulfides (reactive with sulfhydryl groups), hydrazines (reactive with aldehydes), ethyldiethylamino propylcarbodiimide (EDC, reactive with carboxyl groups). Linkers typically include a flexible aliphatic or polymer chain of suitable length and hydrophilicity to bridge between linked molecules. Bivalent linker groups can be provided having the same or different linker chemistries at each end. Linkers can include one or more protective group to protect the linker group during storage, handling or other chemistries. The protective group can be removed under defined conditions to allow completion of a linker reaction.

The dyes of the invention can readily be conjugated (linked) to selected binding domains by using linker chemistries described herein, and known by those skilled in the art. Intelligent design of linkage reactions typically starts with selection of a target reactive group in a binding domain, or engineering of a desired reactive group into the binding domain. For example, a binding domain might naturally have a cysteine residue (reactive, e.g., with a haloacetyls linker) at an appropriate location, or can be mutated to include such a cysteine residue. Alternatively, binding domains can have a small number of cysteine residues. Binding domains can be modified or mutated to contain a single or a small number of cysteine residues by procedures available in the art.

The selected binding domain is conjugated to a dye of the invention by adding a sufficient amount (e.g., 10-20 mM) of the dye in DMSO to a sufficient amount of binding domain (e.g. 200 µL of a 200 µM solution of the binding domain). The dye-binding domain mixture can be incubated in buffer at roughly neutral pH (e.g. in sodium phosphate buffer, pH 7.5) to produce a final dye concentration of about 1-2 mM. The reaction mixture is incubated for about 4 hours at room temperature and is then quenched by addition of 1 µL of mercaptoethanol. The reaction mixture can be centrifuged (e.g. at 12,000 rpm) for a short period of time (e.g. 2 min) to remove precipitated materials that might have formed during the reaction. The supernatant from the centrifugation can be further purified using gel filtration (e.g. G25 Sepharose gel filtration). The dye-to-protein ratio can be calculated by measuring protein and dye concentrations using absorbance spectroscopy as described in Haugland, R. P. *Handbook of Fluorescent Probes and Research Chemicals*; Molecular Probes Inc.: Eugene, Oreg., 1996. Aliquots of the biosensors so generated can be stored at −80° C. No significant loss of binding ability is generally observed after even six months of storage. Changes in reaction time, temperature and solvent compositions can be used to influence the extent and position of labeling.

Administration of Biosensors

Biosensors of the invention can be used in vitro and/or in vivo to detect target molecules of interest. In many cases, the biosensors can simply be added to test samples in a homogenous assay, not requiring addition of multiple reagents and/or wash steps before detection of the target.

Biosensors of the invention can typically contact target molecules in vitro by simple addition to a test sample containing the target molecules. Test samples for in vitro assays can be, e.g., molecular libraries, cell lysates, analyte eluates from chromatographic columns, and the like. The in vitro assay often takes place in a chamber, such as, e.g., a well of a multiwell plate, a test tube, an Eppendorf tube, a spectrophotometer cell, conduit of an analytical system, channels of a microfluidic system, and the like. In an exemplary in vitro assay of the invention, an enzyme protein of interest is coated to the bottom of 96-well dishes also containing solutions representing a library of possible enzyme substrates. A biosensor of the invention with specific affinity for enzyme-substrate complex is added to each well. A multiwell scanning fluorometer is used to observe each well for fluorescence. Wells containing enzyme substrate can be identified as those in which fluorescent emissions at the wavelength of the biosensor dye. That is, in this example, the binding domain of the biosensor only binds to enzyme acting on substrate; the binding placing the dye into a binding pocket environment that significantly changes the emissions intensity of the dye.

Where biosensors of the invention are administered to living cells, binding can take place with targets on the cell surface, or the biosensor is transferred into the cell to make contact with an intracellular target molecule. In some cases, the biosensor can penetrate a cell suspected of containing a selected target passively by mere exposure of the cell to a medium containing the biosensor. In other embodiments, the biosensor is actively transferred into the cell by mechanisms known in the art, such as, e.g., poration, injection, transduction along with transfer peptides, and the like.

In some embodiments, one of skill in the art may choose to incorporate a translocation functionality on the biosensor in order to facilitate the translocation or internalization of that biosensor from the outside to inside the cell. As used herein, the term "translocation functionality" refers to a chemical compound, group or moiety that increases the cell's ability to internalize another compound or material, for example, a biosensor. Examples of such translocation functionalities include peptide recognition/transport sequences, liposomal compositions, or the like. Alternative translocation methods and compositions are also utilized in accordance with the present invention to induce uptake of the second component, including, e.g., electroporation, cell permeating compositions containing, e.g. PEG, porins, saponins, streptolysin or the like.

Techniques useful for promoting uptake of biosensors include optoporation, for example, as described in Schneckenburger, H., Hendinger, A., Sailer, R., Strauss, W. S. & Schmitt, M. Laser-assisted optoporation of single cells. *J Biomed Opt* 7, 410-6 (2002); or Soughayer, J. S. et al., Characterization of Cellular Optoporation with Distance. *Anal Chem* 72, 1342-7 (2000). A variety of transduction peptides are also useful for promoting uptake of biosensors including those described in Zelphati, O. et al., Intracellular Delivery of Proteins with a New Lipid-mediated delivery System. *J Biol Chem* 276, 35103-10 (2001); Yang, Y., Ma, J., Song, Z. & Wu, M., HIV-1 TAT-Mediated Protein Transduction and Subcellular Localization Using Novel Expression Vectors. *FEBS Lett* 532, 36-44 (2002); and Torchilin, V. P. et al., Cell Transfection in Vitro and In Vivo with Nontoxic TAT Peptide-liposome-DNA Complexes. *Proc Natl Acad Sci U.S.A.* 100, 1972-7 (2003).

Additional techniques such as electroporation can also be used. Examples of electroporation procedures are provided in Glogauer, M. & McCulloch, C. A., Introduction of Large Molecules into Viable Fibroblasts by Electroporation: Optimization of Loading and Identification of Labeled Cellular Compartments. *Exp Cell Res* 200, 227-34 (1992); Teruel, M. N. & Meyer, T., Parallel Single-cell Monitoring of Receptor-triggered Membrane Translocation of a Calcium-sensing Protein Module. *Science* 295, 1910-2 (2002); and Teruel, M. N., Blanpied, T. A., Shen, K., Augustine, G. J. & Meyer, T., A Versatile Microporation Technique for the Transfection of Cultured CNS Neurons. *J Neurosci Methods* 93, 37-48 (1999).

Another procedure for introducing molecules such as biosensors into cells is the osmotic shock procedure. Examples of osmotic shock procedures include those described in Okada, C. Y. & Rechsteiner, M., Introduction of Macromolecules into Cultured Mammalian Cells by Osmotic Lysis of Pinocytic Vesicles. *Cell* 29, 33-41 (1982); and Park, R. D., Sullivan, P. C. & Storrie, B., Hypertonic Sucrose Inhibition of Endocytic Transport Suggests Multiple Early Endocytic Compartments. *J Cell Physiol* 135, 443-50 (1988).

One of skill in the art may also employ bead/syringe loading to introduce the biosensors of the invention into cells. Bead/syringe loading procedures are described in McNeil, P. L., Murphy, R. F., Lanni, F. & Taylor, D. L., A Method for Incorporating Macromolecules into Adherent Cells, *J. Cell Biol.* 98, 1556-1564 (1984); and McNeil, P. L. & Warder, E., Glass Beads Load Macromolecules into Living Cells. *Journal of Cell Science* 88, 669-678 (1987).

Nucleic acids encoding binding domains of the invention can optionally be introduced into cells in expression plasmids, e.g., by transduction or other forms of transformation. Once inside the living cells, the binding domain can be translated from the nucleic acid to a functional peptide. Dyes of the invention can enter the cell, e.g., by injection of diff-usion to become linked to the expressed binding domain to generate a biosensor in situ.

Optionally, entire biosensor systems can be encoded on a plasmid, including reporter moieties. For example, a sensor of GTPase activation can comprise a nucleic acid encoding, in order: a single peptide chain of the GTPase, one or more reporter moieties, and a domain that binds the activated GTPase. According to the invention reporter moieties are polypeptides that act as signaling entities. The reporter moieties may be any polypeptides that show fluorescence at known wavelengths upon exposure to external light. Examples of reporter moieties include cyan fluorescent protein (CFP) and a yellow fluorescent protein (YFP), which are mutants of the green fluorescent protein (GFP). Exemplary GTPases can include, e.g., Rho, Rac, Arf, CDC42, and the like. On expression, e.g., conditions in a cell that activate the GTPase can allow binding of the domain to the GTPase while changing the distance, orientation or association between the CFP and YFP with a concomitant change in a FRET signal. This arrangement can be advantageous in that important regulatory interactions and membrane localization sequences remain intact because the GTPase is on the end of the biosensor chain, yet a strong FRET signal can still be obtained. A biosensor of this type has been accomplished and used to monitor GTPase activation in living cells. Expressing all the biosensor components as a single genetically-encoded chain can have benefits, such as, e.g., allowing administration of the biosensor by transfection and allowing stable biosensor cell lines to be produced.

Detection of Target-Biosensor Binding Reactions

A wide variety of binding reactions can be detected and monitored using the present biosensors, for example, protein-protein interactions, receptor-ligand interactions, nucleic acid interactions, protein-nucleic acid interactions, and the like. Detection of a target molecule can provide identification of the target in a specified state, quantification of the target, and/or localization of the target. Multiple measurements can allow determination of kinetics. The ability to monitor multiple targets can permit monitoring of the balance between different signaling activities. In the intracellular environment, many of these reaction types are involved in the multiplicity of steps of signal transduction within cells. For example, activation of a particular cellular event is often triggered by the interaction between a cell surface receptor and its ligand. The signal from the receptor is often transmitted along via the binding of enzymes to other proteins, for example, kinases, which then pass the signal on through the cell until the ultimate cell system response is achieved. In many cases, the signal or ultimate response can be detected using biosensors of the invention. For example, signal transduction often involves phosphorylation of system molecules that can be detected directly with the phosphate involved in the binding site, or indirectly through conformational changes induced by the phosphorylation.

In one embodiment, the invention provides methods for identifying the activation status of endogenous proteins in living cells. Biosensors of the invention can permit identification, quantification, and resolution of the spatial, temporal and compartmental regulation of receptor phosphorylation and activation during various processes, for example, endocytosis. In another embodiment, the biosensors and methods of the invention can permit observation of epidermal growth factor receptor (EGFR) effects on the development and progression of breast cancer. In a further embodiment, complex formation between HIV gp120 and CD4 cell receptors can be monitored.

In accordance with the present invention, binding interactions can occur between a biosensor and one or more target molecules or components of the cell. A "target molecule of interest" is a molecule that is known by one of skill in the art and is selected for interaction with a biosensor of the invention. A target molecule often comprises an endogenous unlabeled and/or untagged component of a test solution or cell. Endogenous components can be, e.g., expressed by the cell naturally, or present as a result of introduction of an appropriate genetic construct within the cell. For example, nucleic acid or protein target molecules can be expressed in the cell, either naturally (e.g., constitutively) or by induction of an appropriate genetic construct introduced into the cell line.

Cells Subject to Biosensor Detection

The methods and biosensors of the present invention can be useful in detection of target molecules in or on the surface of virtually any type of biological cell, including, mammalian, bacterial, fungal, yeast, insect, and plant cells. In some embodiments, target molecules can be detected in freshly isolated cells from mammals (e.g., humans), insects, fugal, or bacterial cells. For example, blood cells, such as B cells, T cells, monocytes, and neutrophils, and the like, can be probed with biosensors of the invention. In other embodiments, stably maintained cell lines such as CHO, HEK-293, L-cells, 3T3 cells, COS, or THP-1 cells can be investigated using methods of the invention.

Useful information can be obtained from any type of cell using the biosensors and methods of the invention. For example, mammalian cells, such as human cells or animal cells, that naturally or recombinantly express human proteins can be evaluated to identify potential human therapeutics, observed for interactions between biomolecules, and/or studied for the effects of ligands, drugs, and other molecules on mammalian and human systems. In another example, bacterial or fungal cells can be used to screen for potential antibiotic or anti-fungal agents.

In some embodiments, well characterized cell lines known to provide predictive models of human cell functions can be used to obtain results correlated with human systems in pharmaceutical and medical research. Exemplary cell lines useful in such research include, for example, COS cells, CHO cells, HEK-293 cells, RBL-1, Jurkat, U937, and YB-1 cells.

The cells to be monitored can be provided in either immobilized form or as a suspension culture. Immobilized cells, such as, e.g., cell lawns, tissue slices, or libraries, can be monitored, e.g., by microscopy, scanners, or with imaging systems. The immobilized cells can be monitored live or fixed for detection of target molecules in killed cells.

In many embodiments, cells subject to target molecule detection with biosensors of the invention are in suspension. Suspended cells can be cells from suspension cell culture or cells liberated from tissues or lawns. Suspended cells are particularly well suited to handling and monitoring in fluidic systems, such as cell sorters, cell counters, and microfluidic systems. Cell suspensions can be provided at cell densities appropriate to the handling system and detection method that is being employed. Determination of optimal cell densities is routine for one of ordinary skill in the art. In the case of flow-through embodiments of the invention, cell densities of monitored suspensions generally range from about 1 cell/nl to about 30 cells/nl in , e.g., a reaction vessel or detection channel. In the case of test tube or multiwell plate based reactions, cell densities typically range from about 1,000 cells/mm$^2$ to about 100,000 cells/mm$^2$. Of course, these ranges can vary depending upon, e.g., the cell types used, the type of biosensor employed, the type of interaction to be studied, the relative adherence of the cells to the vessel surfaces, as well as each other factors.

Biosensor Kits

The invention further provides a packaged composition such as a kit or other container for detecting, monitoring or otherwise observing a target molecule. The kit or container can hold a biosensor of the invention and instructions for using the biosensor for detecting, monitoring or otherwise observing a target molecule. The biosensor includes at least one binding domain and a dye. In one embodiment, the kit comprises a container containing a biosensor comprising scFv binding domain and a dye. Alternatively, the kit or container holds a dye of the invention and instructions for using the dye. In some embodiments, kits containing dyes can contain instructions for attaching a dye to a binding domain selected by one of skill in the art.

The kits of the invention can also comprise containers with solutions or tools useful for manipulating or using the dyes or biosensors of the invention. Such tools include buffers, reaction tubes, reagents for coupling dyes of the invention to selected binding domains and the like. In one embodiment, the kit can contain a solution of solvents and/or buffers to facilitate coupling of a dye of the invention to a selected binding domain and/or a solution of mercaptoethanol for quenching the dye-binding domain conjugation reaction. The kit can also contain a container of buffer at roughly neutral pH (e.g. sodium phosphate buffer, pH 7.5).

The following examples are illustrative of the present invention, but are not limiting. Numerous variations and modifications on the invention as set forth can be effected without departing from the spirit and scope of the present invention.

EXAMPLE 1

Synthesis of Dyes

This Example describes the synthesis of useful, water-soluble derivatives of the 1a dye. New analogues were made, for example, by substitution of a quaternary amino group in the 1a dye with a much more hydrophilic sulfonato group (—SO$_3$Na). In some analogues, cysteine-selective iodoacetamido groups were also added (e.g., at R$_2$) for covalent attachment to binding domains.

Dyes having formulae 1-4 were synthesized. Formula 1 is as follows.

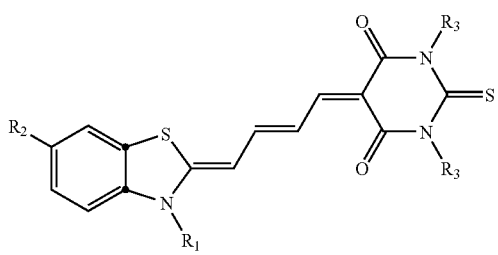

Structure 1 is also referred to herein as S-TBA. A number of different dye compounds were made that had formula 1, including those with structures 1a-1h. The substituents present on each of dye compounds 1a-1h were as follows:

1a: R$_1$=—(CH$_2$)$_3$—N$^+$(CH$_3$)$_2$—(CH$_2$)$_2$—NCS; R$_2$=H; R$_3$=butyl.
1b: R$_1$=ethyl; R$_2$=H; R$_3$=methyl.
1c: R$_1$=—(CH$_2$)$_3$—SO$_3$$^-$; R$_2$=H; R$_3$=methyl.
1d: R$_1$=—(CH$_2$)$_3$—SO$_3$$^-$; R$_2$=FmocNH—; R$_3$=methyl.
1e: R$_1$=—(CH$_2$)$_3$—SO$_3$$^-$; R$_2$=NH$_2$; R$_3$=methyl.
1f: (S-TBA-IAA): R$_1$=—(CH$_2$)$_3$—SO$_3$$^-$; R$_2$=ICH$_2$CONH$_2$; R$_3$=methyl.
1h: R$_1$=—(CH$_2$)$_3$—SO$_3$$^-$; R$_2$=CH$_3$CONH—; R$_3$=methyl.
R$_1$=—(CH$_2$)$_3$—SO$_3$$^-$; R$_2$=HO(CH$_2$)$_2$—S—CH$_2$CONH—; R$_3$=methyl.

Formula 2 is as follows.

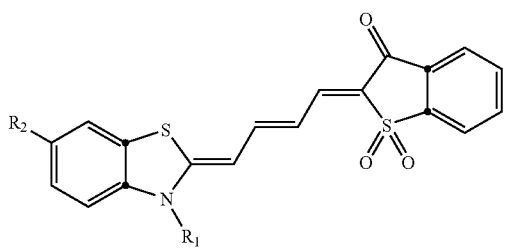

Structure 2 is also referred to herein as S—SO. A number of different dye compounds were made that had formula 2, including those with structures 2a-2g. The substituents present on each of dye compounds 2a-2g were as follows:

2a: R$_1$=ethyl; R$_2$=H.
2b: R$_1$=—(CH$_2$)$_3$—SO$_3$$^-$; R$_2$=H.
2c: R$_1$=—(CH$_2$)$_3$—SO$_3$$^-$; R$_2$=FmocNH—.
2d: R$_1$=—(CH$_2$)$_3$—SO$_3$—; R$_2$=NH$_2$.
2e: (S—SO—IAA): R$_1$=—(CH$_2$)$_3$—SO$_3$$^-$; R$_2$=ICH$_2$CONH—.
2f: (S—SO—OSu): R$_1$=—(CH$_2$)$_3$—SO$_3$—; R$_2$=SuOCOCH$_2$OCH$_2$CON(CH$_3$)—.
2g: R$_1$=—(CH$_2$)$_3$—SO$_3$$^-$; R$_2$=HO(CH$_2$)$_2$S—CH$_2$CONH—.

Formula 3 is as follows.

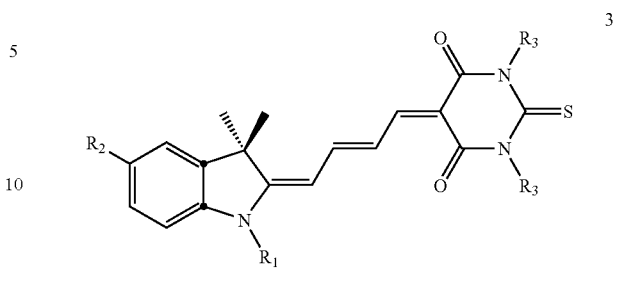

Structure 3 is also referred to herein as I-TBA. A number of different dye compounds were made that had formula 3, including those with structures 3a-3b. The substituents present on each of dye compounds 3a-3b were as follows:

3a: R$_1$=ethyl; R$_2$=H.
3b: R$_1$=—(CH$_2$)$_3$—SO$_3$$^-$; R$_2$=H.

Formula 4 is as follows.

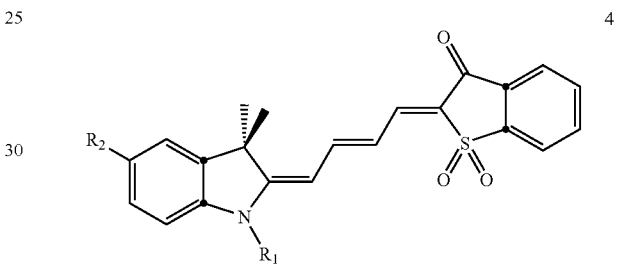

Structure 4 is also referred to herein as I—SO. A number of different dye compounds were made that had formula 4, including those with structures 4a-4g. The substituents present on each of dye compounds 4a-4g were as follows:

4a: R$_1$=methyl; R$_2$=H.
4b: R$_1$=—(CH$_2$)$_3$—SO$_3$$^-$; R$_2$=H.
4c: R$_1$=—(CH$_2$)$_3$—SO$_3$$^-$; R$_2$=FmocNH—.
4d: R$_1$=—(CH$_2$)$_3$—SO$_3$$^-$; R$_2$=NH$_2$.
4e: (I—SO—IAA): R$_1$=—(CH$_2$)$_3$—SO$_3$$^-$; R$_2$=ICH$_2$CONH—.
4f; (I—SO—OSu): R$_1$=—(CH$_2$)$_3$—SO$_3$$^-$; R$_2$=SuOCOCH$_2$OCH$_2$CON(CH$_3$)—.
4g: R$_1$=—(CH$_2$)$_3$—SO$_3$$^-$; R$_2$=HO(CH$_2$)$_2$S—CH$_2$CONH—.

These compounds were synthesized as shown in FIG. 8. A description of the materials and methods used follows.

Materials

Analytical grade reagents were purchased from major suppliers. UV-visible spectra were measured using a Hewlett-Packard 8453 diode array spectrophotometer. Emission and excitation spectra were obtained using a Spex Fluorolog 2 spectrofluorometer at 23° C. Quantum yields were measured using merocyanine 540 (Onganer et al., *J. Phys. Chem.* 1993, 97, 2344-54) as an internal standard. Demas et al., *J. Phys. Chem.* 1971, 75, 991-1024. Solutions were not deaerated because control experiments showed that oxygen did not quench the fluorescence of these dyes, due perhaps to their short lifetimes. Mass spectra were obtained on an IonSpec FT MS spectrometer (MALDI-FT MS), Hewlett-Packard 5890 gas chromatograph equipped with a 5971A mass selective detector (MS-El), and Hewlett-Packard 1100 high-performance liquid chromatograph equipped with a 1100 mass selective detector (MS-ESI). $^1$H spectra of 0.5% solutions in CDCl$_3$ or CD$_3$SOCD$_3$ were recorded on Bruker DRX-400 or DRX-500 spectrometers. The peaks corresponding to the residual protons of CDCl$_3$ (7.27 ppm) or CD$_3$-SOCD$_3$ (2.49 ppm) were used as internal reference. All operations with dyes were performed under dim light. Flasks containing dyes were wrapped with aluminum foil.

3-(2,3,3-Trimethyl-3H-indolium-1-yl)propane-1-sulfonate (5) was prepared as previously reported by Flannagan et al., *Bioconj. Chem.* 1997, 8, 751-756.

3-(2-methyl-1,3-benzothiazol-3-ium-3-yl)propane-1-sulfonate (6) was prepared as previously reported by Lednev et al., *Spectrochim. Acta, Part A* 1993, 49A, 1055-1056.

3-ethyl-2-methyl-1,3-benzothiazol-3-ium iodide (7),66 1-benzothiophen-3(2H)-one 1,1-dioxide was prepared as previously reported by Regitz, M. *Chem. Ber.* 1965, 98, 36-45.

2,3,3-trimethyl-3H-indol-5-amine was prepared as previously reported by Mujumdar et al., *Cytometry* 1989, 10, 11-19.

2-methyl-1,3-benzothiazol-6-amine was prepared as previously reported by Manning, W. B.; Horak, V. *Synthesis* 1978, 5, 363.

Chemical names for compounds were obtaining using ACD/Chem-Sketch software obtained from Advanced Chemistry Development Inc.: Toronto, Canada.

5-[(2E)-3-Methoxyprop-2-enylidenel]-1,3-dimethyl-2-thioxodihydropyrimidine-4,6(1H,51H)-dione (8). 1,3,3-Trimethoxypropene (1.32 g, 10 mmol) was added rapidly to a boiling solution of 1,3-dimethyl-2-thiobarbituric acid (1.29 g, 7.5 mmol) in 10 mL of a CHCl3-MeOH (1:1) mixture. Reflux was continued for 5 min, and the solution was cooled to room temperature. The solid formed was filtered, washed with a small amount of MeOH, and dried. The yield was 1.20 g (75%). $^1$H NMR (400 MHz, CDCl$_3$): δ 3.71 (s, 6H, 2×CH3), 3.96 (s, 3H, OCH$_3$), 7.48 (t, $^3J_{H-H}$) 12.5 Hz, 1H), 7.56 (d, $^3J_{H-H}$) 12.5 Hz, 1H), 8.11 (d, $^3J_{H-H}$) 12.5 Hz, 1H). GC-MS (70 eV) m/e (relative intensity): 240 (100, M$^+$), 209 (25, (M−OCH$_3$)$^+$).

(2E)-2-[(2E)-3-Methoxyprop-2-enylidene]-1-benzothiophen-3(2H)-one 1,1-Dioxide (9). A mixture of 1,3,3-trimethoxypropene (2.64 g, 20 mmol) and 1.82 g (10 mmol) of 1-benzothiophen-3(2H)-one 1,1-dioxide was heated at 90° C. for 12 h. The solid formed was recrystallized from MeOH to give 1.88 g (75% yield) of final product. $^1$H NMR (400 MHz, CDCl$_3$): δ 4.02 (s, 3H, OCH$_3$), 6.51 (t, $^3J_{H-H}$=12.3 Hz, 1H), 7.51-8.11 (m, 6H). GC-MS (70 eV) m/e (relative intensity): 250 (65, M+), 219 (100, (M−OCH$_3$)$^+$).

General Procedure A (Dyes 3a, 4a). 2-Methylene-1,3,3-trimethylindolenine (300 mg, 1.9 mmol) was added at once to a boiling solution of 500 mg (2.00 mmol) of enol ether 8 or 9 in 5.0 mL of a methanol chloroform mixture (1:1). The reaction mixture was stirred at reflux for 30 min. After cooling, the dye separated as a crystalline solid. The dye was additionally purified by recrystallization from methanol.

1,3-Dimethyl-2-thioxo-5-[(2E,4Z)-4-(1,3,3-trimethyl-1,3-dihydro-2H-indol-2-ylidene)but-2-enylidene]dihydropyrimidine-4,6(1H,5,H)-dione (3a). The yield was 75%. $^1$H NMR (500 MHz, CDCl$_3$): δ 1.74 (s, 6H, C(CH$_3$)$_2$), 3.56 (s, 3H, NCH$_3$), 3.88 (s, 6H, 2×CH$_3$), 6.09 (d, $^3J_{H-H}$=12.5 Hz, 1H), 7.06-8.22 (m, 6H). MALDI-FTMS: MH$^+$ found 382.1584, expected 382.1584.

(2Z)-2-[(2E,4Z)-4-(1,3,3-Trimethyl-1,3-dihydro-2H-indol-2-ylidene)-but-2-enylidene]-1-benzothiophen-3(2H)-one 1,1-Dioxide (4a). The yield was 68%. $^1$H NMR (500 MHz, DMSO-d$_6$): δ 1.70 (s, 6H, C(CH$_3$)$_2$), 3.60 (s, 3H, NCH$_3$), 6.33 (d, $^3J_{H-H}$=13.6 Hz, 1H), 6.71 (t, J$_{H-H}$=13.2 Hz, 1H), 7.2-8.0 (m, 8H), 8.28 (t, $^3J_{H-H}$) 13.6 Hz, 1H). MALDI-FTMS: MH$^+$ found 392.1313, expected 392.1315.

General Procedure B (Dyes 1b, 1c, 2a, 2b, 3b, 4b). Indolium or benzothiazolium salt (5, 6, or 7, 1.00 mmol) was added at once to a boiling solution of enol ether 8 or 9 (500 mg, 2.0 mmol) in 5.0 mL of a methanol-chloroform mixture (1:1) followed by addition of 100 mg of sodium acetate. The reaction mixture was stirred at reflux for 30 min. After cooling, the dye separated as a crystalline solid. The dye was additionally purified by recrystallization from methanol.

1,3-Dimethyl-5-[(2E,4E)-4-(3-ethyl-1,3-benzothiazol-2(3H)-ylidene)-but-2-enylidene]-2-thioxodihydropyrimidine-4,6(1H,5H)-dione (1b). The yield was 85%. $^1$H NMR (500 MHz, CDCl$_3$): δ 1.55 (t, $^3J_{H-H}$=6.6 Hz, 3H, CH$_3$), 3.86 (s, 6H, 2×CH$_3$), 4.26 (q, $^3J_{H-H}$=6.6 Hz, 2H, CH$_2$N), 6.27 (d, $^3J_{H-H}$), 12.8 Hz, 1H), 7.40-8.06 (m, 7H). MALDIFTMS: MH$^+$ found 386.0989, expected 386.0991.

Sodium 3-[(2E)-2-[(2E)-4-(1,3-Dimethyl-4,6-dioxo-2-thioxotetrahydro-pyrimidin-5(2H)-ylidene)but-2-enylidene]-1,3-benzothiazol-3(2H)-yl]propane-1-sulfonate (1c). The yield was 82%. $^1$H NMR (500 MHZ, CDCl$_3$): δ 2.03 (p, $^3J_{H-H}$=7.0 Hz, 2H, CH$_2$CH$_2$CH$_2$), 2.60 (t, $^3J_{H-H}$=7.0 Hz, 2H, CH$_2$SO$_3$), 3.58 (s, 6H, 2×CH3), 4.61 (t, $^3J_{H-H}$=7.0 Hz, 2H, CH$_2$N), 6.91 (d, $^3J_{H-H}$=13.6 Hz, 1H), 7.40-8.06 (m, 7H). MALDI-FTMS MH$^+$ found 502.0545; expected 502.0536.

(2Z)-2-[(2E,4E)-4-(3-Ethyl-1,3-benzothiazol-2(3H)-ylidene)but-2-enylidene]-1-benzothiophen-3(2H)-one 1,1-Dioxide (2a). The yield was 70%. $^1$H NMR (400 MHz, DMSO-d$_6$): δ 1.29 (t, $^3J_{H-H}$=6.6 Hz, 3H, CH3), 4.40 (q, $^3J_{H-H}$=6.6 Hz, 2H, CH$_2$N), 6.57 (t, $^3J_{H-H}$=13.6 Hz, 1H), 6.71 (d, $^3J_{H-H}$=13.6 Hz, 1H), 7.3-7.8 (m, 10H). MALDI-FTMS: MH$^+$ found 396.0728, expected 396.0723.

Sodium 3-[(2E)-2-[(2E,4Z)-4-(1,1-Dioxido-3-oxo-1-benzothien-2(3H)-ylidene)but-2-enylidene]-1,3-benzothiazol-3(2H)-yl]propane-1-sulfonate (2b). The yield was 67%. $^1$H NMR (500 MHz, DMSOd$_6$): δ 1.85 (p, $^3J_{H-H}$=7.0 Hz, 2H, CH$_2$CH$_2$CH$_2$), 2.60 (t, $^3J_{H-H}$=7.0 Hz, 2H, CH$_2$SO$_3$), 4.44 (t, $^3J_{H-H}$=7.0 Hz, 2H, CH$_2$N), 6.67 (t, 3J$_{H-H}$=12.8 Hz, 1H), 6.87 (d, $^3J_{H-H}$=13.2 Hz, 1H), 7.40-8.10 (m, 10H). ESI-MS: 490 (M−Na+2H)$^+$.

Sodium 3-{(2Z)-2-[(2E)-4-(1,3-Dimethyl-4,6-dioxo-2-thioxotetrahydro-pyrimidin-5(2H)-yldene)but-2-enyldene]-3,3-dimethyl-2,3-dihydro-1H-indol-1-yl}propane-1-sulfonate (3b). The yield was 70%. $^1$H NMR (500 MHz, CDCl$_3$): δ 1.74 (s, 6H, C(CH$_3$)$_2$), 2.05 (p, $^3J_{H-H}$=7.0 Hz, 2H, CH$_2$CH$_2$CH$_2$), 2.63 (t, $J_{H-H}$=7.0 Hz, 2H, CH$_2$SO$_3$), 3.67 (s, 6H, 2×CH3), 4.34 (t, $^3J_{H-H}$=7.0 Hz, 2H, CH$_2$N), 6.58 (d, $^3J_{H-H}$=12.6 Hz, 1H), 7.2-8.4 (m, 7H). ESI-MS: 490 (M−Na+2H)$^+$.

Sodium 3-{(2Z)-5-2-[(2E,4Z)-4-(1,1-Dioxido-3-oxo-1-benzothien-2(3H)-ylidene)but-2-enylidene]-3,3-dimethyl-2,3-dihydro-1H-indol-1-yl}propane-1-sulfonate (4b). The yield was 65%. $^1$H NMR (500 MHz, DMSO-d$_6$): δ 1.74 (s, 6H, C(CH$_3$)$_2$), 2.05(p, $^3J_{H-H}$=7.0 Hz, 2H, CH$_2$CH$_2$CH$_2$), 2.63 (t, $^3J_{H-H}$=7.0 Hz, 2H, CH$_2$SO$_3$), 4.25(t, $^3J_{H-H}$=7.0 Hz, 2H, CH$_2$N), 6.47 (d, $^3J_{H-H}$=13.6 Hz, 1H), 6.72 (t, $^3J_{H-H}$=13.2 Hz, 1H), 7.2-8.4 (m, 10H). ESI-MS: 500 (M−Na+2H)$^+$.

Preparation of Thiol-Reactive S-TBA-IAA (1f), S—SO—IAA (2e), and I—SO—IAA (4e) Dyes. 9H-Fluoren-9-ylmethyl 2-Methyl-1,3-benzothiazol-6-ylcarbamate (10). A 1.64 g (0.01 mol) sample of 2-methyl-6-aminobenzothiazole was added in small portions to 40 mL of a 1:1 mixture of FMOC—Cl in chloroform (2.59 g, 0.01 mol) and saturated aqueous sodium bicarbonate solution at room temperature. After addition was completed, stirring was continued for 1 h. The organic layer was separated, washed with water (2×20 mL), and dried over MgSO$_4$. The solvent was removed in a vacuum, and the solid residue was recrystallized from methanol to give 3.0 g (80%) of protected amine. $^1$H NMR (400 MHz, CDCl$_3$): δ 2.79 (s, 3H, CH3), 4.27 (t, $^3J_{H-H}$=6.2 Hz, 2H, OCH$_2$), 4.58 (d, $^3J_{H-H}$=6.2 Hz, 1H, CH) 6.8-7.8 (m, 11H, aromatic rings), 8.3 (bs, 1H, NH). ESI-MS: 387 (MH$^+$).

9H-Fluoren-9-ylmethyl 2,3,3-trimethyl-3H-indol-5-ylcarbamate (11). The title compound was prepared by the same method as 10. Protected amine was purified by chromatography on silica using dichloromethane as eluent. The yield was 2.85 g (72%). $^1$H NMR (400 MHz, CDCl$_3$): δ 2.79 (s, 3H, CH$_3$), 4.27 (t, 3J$_{H-H}$=6.2 Hz, 2H, OCH$_2$), 4.58 (d, $^3J_{H-H}$=6.2 Hz, 1H, CH) 6.8-7.8 (m, 11H, aromatic rings), 8.3 (bs, 1H, NH). ESI-MS: 397 (MH$^+$).

9H-Fluoren-9-ylmethyl 2-Methyl-3-(3-sulfonatopropyl)-1,3-benzothiazol-6ylcarbamate (12). A mixture of 8 mmol of protected amine and 1,3-propane sulfone (1.83 g, 15 mmol) in 10 mL of 1,2-dichlorobenzene was heated at 120° C. for 12 h. The solid was filtered and washed with hot benzene and hot methanol to produce a white solid. The yield was 3.45 g (87%). $^1$H NMR (500 MHz, DMSO-d$_6$): δ 2.18 (p, $^3J_{H-H}$=6.2 Hz, 2H, CH$_2$CH$_2$CH$_2$), 2.68 (t, $^3J_{H-H}$=6.2 Hz, 2H, CH$_2$—SO$_3$), 3.20 (s, 3H, CH$_3$), 4.42 (t, $^3J_{H-H}$=6.6 Hz, 1H, CH—CH$_2$), 4.66 (d, $^3J_{H-H}$=6.6 Hz, 2H, CH—CH$_2$), 4.91 (t, t, $^3J_{H-H}$=6.2 Hz, 2H, CH$_2$—N), 7.3-8.5 (m, 10H), 10.34 (bs, 1H). ESI-MS: 509 (MH$^+$).

3-(5-{[(9H-Fluoren-9-yloxy)carbonyl]amino}-2,3,3-trimethyl-3H-indolium-1-yl)propane-1-sulfonate (13). The title compound was prepared by the same method as 12. The yield was 80%. $^1$H NMR (500 MHz, DMSO-d$_6$): δ 1.55 (s, 6H, 2×CH$_3$), 2.21 (p, $^3J_{H-H}$=6.2 Hz, 2H, CH$_2$CH$_2$CH$_2$), 2.70 (t, $^3J_{H-H}$=6.2 Hz, 2H, CH$_2$—SO$_3$), 2.84 (s, 3H, CH$_3$), 4.40 (t, $^3J_{H-H}$=6.6 Hz, 1H, CH—CH$_2$), 4.56 (d, $^3H_{H-H}$=6.6 Hz, 2H, CH—CH$_2$), 4.67 (t, $^3J_{H-H}$=6.2 Hz, 2H, CH$_2$—N), 7.3-8.1 (m, 10H), 10.34 (bs, 1H). ESI-MS: 519 (MH$^+$).

Preparation of Protected Dyes 1d, 2c, and 4c. The dyes were prepared using general procedure B from quaternary salt 12 or 13 and enol ether 8 or 9.

Sodium 3-[(2Z)-{[(9H-Fluoren-9-yloxy)carbonyl]amino}-2-[(2E)-4-(1,3-dimethyl-4,6-dioxo-2-thioxotetrahydropyrimidin-5(2H)-ylidene)-but-2-enylidene]-1,3-benzothiazol-3(2H)-yl]propane-1-sulfonate (1d). The yield was 90%. $^1$H NMR (500 MHz, DMSO-d$_6$): δ 2.09 (p, $^3J_{H-H}$=7.0 Hz, 2H, CH$_2$CH$_2$CH$_2$), 2.49 (t, $^3J_{H-H}$=7.0 Hz, 2H, CH$_2$—SO$_3$), 3.66 (s, 6H, 2×CH$_3$), 4.40 (t, $^3J_{H-H}$=6.2 Hz, 1H, CH—CH2), 4.60-4.70 (m, 4H, CH—CH$_2$, N—CH$_2$), 6.8-8.5 (m, 15H), 10.15 (bs, 1H). MALDI-FTMS: MH$^+$ found 739.1343, expected 739.1325.

Sodium 3-[(2E)-6-{[(9H-Fluoren-9-yloxy)carbonyl]amino}-2-[(2E,4Z)-4-(1,1-dioxido-3-oxo-1-benzothien-2(3H)-ylidene)but-2-enylidene]-1,3-benzothiazol-3(2H)-yl]propane-l-sulfonate (2c). The yield was 85%. $^1$H NMR (500 MHz, DMSO-d$_6$): δ 2.03 (p, $^3J_{H-H}$=7.0 Hz, 2H, CH$_2$CH$_2$CH$_2$), 2.61 (t, $^3J_{H-H}$=7.0 Hz, 2H, CH$_2$—SO$_3$), 4.39 (t, $^3J_{H-H}$=6.2 Hz, 1H, CH—CH2), 4.50-4.70 (m, 4H, CH$_2$—N, CH—CH$_2$), 6.5-8.0 (m, 19H), 10.2 (bs, 1H). MALDI-FTMS: MH$^+$ found 749.1033, expected 749.1056.

Sodium 3-{(2Z)-5-{[(9H-Fluoren-9-yloxy)carbonyl]amino}-2-[(2E,4Z)-4-(1,1-dioxido-3-oxo-1-benzothien-2(3H)-ylidene)but-2-enylidene]-3,3-dimethyl-2,3-dihydro-1H-indol-1-yl}propane-1-sulfonate (4c). The yield was 90%. $^1$H NMR (500 MHz, DMSO-d$_6$): δ 1.67(s, 6H, 2×CH$_3$), 2.05 (p, $^3J_{H-H}$=7.0 Hz, 2H, CH$_2$CH$_2$CH$_2$), 2.65 (t, $^3J_{H-H}$=7.0 Hz, 2H, CH$_2$—SO$_3$), 4.24 (t, $^3J_{H-H}$=7.0 Hz, 2H, CH$_2$—N), 4.38 (t, $^3J_{H-H}$=6.6 Hz, 1H, CH—CH$_2$), 4.54 (d, $^3J_{H-H}$=6.6 Hz, 2H, CH—CH$_2$), 6.4-8.5 (m, 19H), 9.95 (bs, 1H). ESI-MS: 737.2 (M−Na+2H)$^+$.

General Procedure for Deprotection of Fmoc Group. Preparation of Dyes 1e, 2d, and 4d. A mixture of Fmoc-protected dye (1.00 mmol) and sodium acetate (10 mg, 0.12 mmol) in 15 mL of dimethyl sulfoxide was stirred at 100° C. for 10 min. The mixture was cooled to 20° C., and the dye was precipitated by addition of 50 mL of diethyl ether. The dye was used without further purification in the next step.

Sodium 3-[(2Z)-6-Amino-2-[(2E)-4-(1,3-dimethyl-4,6-dioxo-2-thioxotetrahydropyrimidin-5(2H)-ylidene)but-2-enylidene]-1,3-benzothiazol-3(2H)-yl]propane-1-sulfonate (1e). The yield was 93%. $^1$H NMR (400 MHz, DMSO-d$_6$): δ 2.00 (p, $^3J_{H-H}$=7.0 Hz, 2H, CH$_2$CH$_2$CH$_2$), 2.55 (t, $^3J_{H-H}$=7.0 Hz, 2H, CH$_2$—SO$_3$), 3.61 (s, 6H, 2×CH$_3$), 4.56 (t, $^3J_{H-H}$=7.0 Hz, 2H, CH$_2$—N), 5.83 (s, 2H, NH$_2$), 6.8-7.8 (m, 7H). ESI-MS: 495 (M−Na+2H)$^+$.

Sodium 3-[(2E)-6Amino-2-[(2E,4Z)-4-(1,1-dioxido-3-oxo-1-benzothien-2(3H)-ylidene)but-2-enylidenel]-1,3-benzothiazol-3(2H)-yl]-propane-1-sulfonate (2d). The yield was 95%. $^1$H NMR (500 MHz, DMSO-d$_6$): δ 2.08 (p, $^3J_{H-H}$=7.0 Hz, 2H, CH$_2$—CH$_2$—CH$_2$), 2.64 (t, $^3J_{H-H}$=7.0 Hz, 2H, CH$_2$—SO$_3$), 4.57 (t, $^3J_{H-H}$=7.0 Hz, 2H, CH$_2$—N), 5.78 (s, 2H, NH$_2$), 6.4-7.8 (m, 11H). ESI-MS: 505 (M−Na+2H)$^+$.

Sodium 3-{(2Z)-5-Amino-2-[(2E,4Z)-4-(1,1-dioxido-3-oxo-i-benzothien-2(3H)-ylidene)but-2-enylidenel]-3,3-dimethyl-2,3-dihydro-1H-indol-1-yl}propane-1-sulfonate (4d). The yield was 80%. $^1$H NMR (500 MHz, DMSO-d$_6$): δ 1.58 (s, 6H, 2×CH$_3$), 2.03 (p, $^3J_{H-H}$=6.2 Hz, 2H, CH$_2$—CH$_2$—CH$_2$), 2.63 (t, $^3J_{H-H}$=6.2 Hz, 2H, CH$_2$—SO$_3$), 4.24 (t, $^3J_{H-H}$=6.2 Hz, 2H, CH$_2$—N), 5.42 (s, 2H, NH$_2$), 6.4-8.5 (m, 11H). ESI-MS: 515 (M−Na+2H)$^+$.

Sodium 3-{(2Z)-5-[(Iodoacetyl)amino]-2-[(2E,4Z)-4-(1,1-dioxido-3-oxo-1-benzothien-2(3H)-ylidene)but-2-enylidene]-3,3-dimethyl-2,3-dihydro-1H-indol-1-yl}propane-1-sulfonate (I—SO—IAA, 4e). A solution of chloroacetyl chloride (200 mg, 1.78 mmol) in 2 mL of DMF was added dropwise to a cooled (−40° C.) solution of 250 mg (0.47 mmol) of dye 21 and 100 mg of triethylamine in 10 mL of DMF. After addition was completed, the reaction mixture was stirred at −40° C. for an additional hour. Methanol (10 mL) was added to the reaction mixture, and the temperature was slowly raised to room temperature. Diethyl ether was added to the mixture to precipitate the dye. The crude dye was chromatographed over silica gel, eluting with acetone-methanol (3:1) to yield 201 mg (70%) of pure chloroacetamido dye. This dye was refluxed in 10 mL of methanol containing 600 mg of sodium iodide for 3 h. The solution was cooled, filtered, and concentrated in a vacuum to 5 mL. The dye was precipitated by addition of 50 mL of acetone, filtered, and dried. The dye was purified by recrystallization from methanol. The yield was 209 mg (63% based on starting dye 21). $^1$H NMR (500 MHz, DMSO-d$_6$): δ 1.69 (s, 6H, C(CH$_3$)$_2$), 2.03 (p, $^3J_{H-H}$=7.0 Hz, 2H, CH$_2$—CH$_2$—CH$_2$), 2.63 (t, $^3J_{H-H}$=7.0 Hz, 2H, CH$_2$—SO3), 3.91 (s, 2H, CH$_2$I), 4.24 (t, $^3J_{H-H}$=7.0 Hz, 2H, CH$_2$—N), 6.4-8.3 (m, 11H), 10.53 (s, 1H, NH). MALDI-FTMS: MH$^+$ found 705.0219, calculated 705.0197.

Sodium 3-[(2Z)-2-[(2E)-4-(1,3-Dimethyl-4,6dioxo-2-thioxotetrahydro-pyrimidin-5(2H)-ylidene)but-2-enylidenel-6-(iodoacetyl)-amino]-1,3-benzothiazol-3(2H)-yl]propane-1-sulfonate (S-TBA-IAA, 1f). The dye was prepared using the same method as for dye 4e starting from dye 1e. The dye was purified by recrystallization from methanol. The yield was 65%. $^1$H NMR (400 MHz, DMSO-d$_6$): δ 2.07 (p, $^3J_{H-H}$=7.0 Hz, 2H, CH$_2$—CH$_2$—CH$_2$), 2.61 (t, $^3J_{H-H}$=7.0 Hz, 2H, CH$_2$—SO$_3$), 3.57 (s, 6H, 2×CH$_3$), 3.93

(s, 2H, CH$_2$I), 4.59 (t, $^3J_{H-H}$=7.0 Hz, 2H, CH$_2$—N), 6.8-8.5 (m, 7H), 10.5 (s, 1H, NHCO). ESI-MS: 663 (M–Na+2H)$^+$.

Sodium 3-[(2E)-6-[(Iodoacetyl)amino]-2-[(2E,4Z)-4-(1,1-dioxido-3-oxo-1-benzothien-2(3H)-ylidene)but-2-enylidene]-1,3-benzothiazol-3(2H)-yl]propane-1-sulfonate (S—SO—IAA, 2e). The dye was prepared using the same method as for dye 4e starting from dye 2d. The dye was purified by recrystallization from methanol. The yield was 60%. $^1$H NMR (500 MHz, DMSO-d$_6$): δ 2.08 (p, 3JH—H) 7.0 Hz, 2H, CH$_2$—CH$_2$—CH$_2$), 2.67 (t, $^3J_{H-H}$=7.0 Hz, 2H, CH$_2$—SO$_3$), 3.93 (s, 2H, CH$_2$I), 4.57 (t,$^3J_{H-H}$=7.0 Hz, 2H, CH2-N), 6.6-8.5 (m, 11H), 10.74 (s, 1H, NHCO). MALDI-FTMS: MH$^+$ found 694.9431, expected 694.9448.

Preparation of Amino-Reactive I—SO—OSu (4f) and S—SO—OSu (2f) Dyes. N-(2,3,3-Trimethyl-3H-indol-5-yl)acetamide (14) and N-(2-Methyl-1,3-benzothiazol-6-yl)acetamide (15). Amine (2,3,3-trimethyl-3H-indol-5-amine or 2-methyl-1,3-benzothiazol-6-amine), 3mmol, was mixed with acetic anhydride (10 mL), and the mixture was heated at 60° C. for 20 min. The solvents were evaporated in a vacuum, and the residue was purified by recrystallization from alcohol (benzothiazole derivative) or by column chromatography on silica using ethyl acetate as eluent (indolenine derivative).

N-(2,3,3-Trimethyl-3H-indol-5-yl)acetamide. The yield was 60%, yellow powder. $^1$H NMR (400 MHz, CDCl$_3$): δ 1.26 (s, 6H, 2×CH3), 2.15 (s, 3H, COCH$_3$), 2.24 (s, 3H, CH$_3$), 6.8-7.8 (m, 3H, aromatic ring), 8.0 (bs, 1H, NH). ESI-MS: 217 (MH$^+$).

N-(2-Methyl-1,3-benzothiazol-6-yl)acetamide. The yield was 80%, white powder. $^1$H NMR (500 MHz, CDCl3): δ 2.27 (s,3H, COCH$_3$), 2.86 (s, 3H, CH$_3$), 7.3-8.5 (m, 4H, aromatic ring, NH). ESI-MS: 207 (MH$^+$).

N-Methyl-N-(2,3,3-trimethyl-3H-indol-5-yl)acetamide (16) and N-Methyl-N-(2-methyl-1,3-benzothiazol-6-yl)acetamide (17). The acetamide (14 or 15) from the previous synthesis (2.00 mmol) was dissolved in 30 mL of methyl sulfoxide. Sodium hydride (60% suspension in mineral oil, 2.20 mmol) was added to this solution in small portions with stirring. Hydrogen was evolved, and the mixture was kept at room temperature for 30 min. Then, methyl iodide (2.2 mmol) in dimethyl sulfoxide was added dropwise over 10 min. When addition was complete, the mixture was stirred at room temperature for 1 h, then diluted with water (100 mL). Organics were extracted with methylene chloride (3×50 mL). The combined organic layers were washed with water (2×50 mL) and dried. Evaporation of solvent gave N-methylacetamides, which were purified by chromatography on silica using ethyl acetate as eluent.

N-Methyl-N-(2-methyl-1,3-benzothiazol-6-yl)acetamide (16). The yield was 87%, white solid. $^1$H NMR (500 MHz, DMSO-d$_6$): δ 1.87 (s, 3H, COCH$_3$), 2.84 (s, 3H, CH$_3$), 3.29 (s, 3H, NCH$_3$), 7.3-8.5 (m, 3H, aromatic ring). ESI-MS: 221 (MH$^+$).

N-Methyl-N-(2,3,3-trimethyl-3H-indol-5-yl)acetamnide (17). The yield was 72%, white solid. $^1$H NMR (500 MHz, CDCl$_3$): δ 1.31 (s, 6H, 2×CH$_3$),1.85 (s, 3H, COCH$_3$), 2.29 (s, 3H, CH$_3$), 3.26 (s, 3H, NCH$_3$), 7.1-7.6 (m, 3H, aromatic ring). ESI-MS: 231 (MH$^+$).

N,2-Dimethyl-1,3-benzothiazol-6-amine (18) and N,2,3,3-Tetramethyl-3H-indol-5-amine (19). Methylacetamide (18 or 19) from the previous synthesis (1.5 mmol) was mixed with concentrated hydrochloric acid (10 mL), and the mixture was stirred under reflux for 4 h. After cooling, a solution of 6 g of sodium hydroxide in 50 mL of water was added to the mixture. The separated organics were extracted with methylehe chloride (3×50 mL). The combined organic extracts were washed with water (2×50 mL) and dried. Evaporation of solvent gave crude methylamines, which were purified by column chromatography on silica using ethyl acetate as eluent.

N,2-Dimethyl-1,3-benzothiazol-6-amine (18). The yield was 90%, white solid. $^1$H NMR (500 MHz, CDCl$_3$): δ 2.82 (s, 3H, CH$_3$), 2.94 (s, 3H, NCH$_3$), 3.7 (bs, 1H, NH), 6.8-7.3 (m, 3H, aromatic ring). ESIMS: 179 (MH$^+$).

N,2,3,3-Tetramethyl-3H-indol-5-amine (19). The yield was 86%, yellow solid. $^1$H NMR (500 MHz, CDCl$_3$): δ 1.34 (s, 6H, 2×CH$_3$), 2.29 (s, 3H, CH$_3$), 2.94 (s, 3H, NCH$_3$), 3.52 (s, 1H, NH), 6.5-7.5 (m, 3H, aromatic ring). ESI-MS: 189 (MH$^+$). {2-[Methyl(2,3,3-trimethyl-3H-indol-5-yl)amino]-2-oxoethoxy}-acetic Acid (20) and {2-[Methyl(2-methyl-1,3-benzothiazol-6-yl)-amino]-2-oxoethoxy}acetic Acid (21). N-Methylamine from the previous synthesis (1.0 mmol) was dissolved in 20 mL of chloroform. A 1.1 mmol sample of diglycolic anhydride was added, and the mixture was stirred under reflux for 2 h. After cooling, the solvent was evaporated. The solid was recrystallized from acetone to give pure acids.

{2-[Methyl(2,3,3-trimethyl-3H-indol-5-yl)amino]-2-oxoethoxy}-acetic Acid (20). The yield was 75%, white powder. $^1$H NMR (500 MHz, CDCl$_3$): δ 1.33 (s, 6H, 2×CH$_3$), 2.32 (s, 3H, CH$_3$), 3.33 (s, 3H, NCH$_3$), 4.05 (s, 2H, CH$_2$CON), 4.15 (s, 2H, CH$_2$COOH), 3.52 (s, 1H, NH), 7.1-7.7 (m, 3H, aromatic ring). ESI-MS: 305 (MH$^+$).

{2-[Methyl(2-methyl-1,3-benzothiazol-6-yl)amino]-2-oxoethoxy}-acetic Acid (21). The yield was 82%, white powder. $^1$H NMR (500 MHz, DMSO-d$_6$): δ 2.80 (s, 3H, CH$_3$), 3.21 (s, 3H, NCH$_3$), 3.94 (s, 2H, CH$_2$CON), 4.03(s, 2H, CH$_2$COOH), 7.4-8.2 (m, 3H, aromatic ring). ESI-MS: 295 (MH$^+$).

3-{5-[[(Carboxymethoxy)acetyl](methyl)amino]-2,3,3-trimethyl-3H-indolium-1-yl}propane-1-sulfonate (22) and 3-{6-[[(Carboxymethoxy) acetyl](methyl)amino]-2-methyl-1,3-benzothiazol-3-ium-3-yl}propane-1-sulfonate (23). To a solution of acid (21 or 22, 1.00 mmol) in 25 mL of dry acetonitrile was added propane sulfone (10 mmol). This mixture was stirred under reflux for 48 h. After cooling the hygroscopic salt was filtered, washed with acetone, and immediately used in the next step.

3-{5-[[(Carboxymethoxy)acetyl](methyl)amino]-2,3,3-trimethyl-3H-indolium-1-yl}propane-1-sulfonate (22). The yield was 72%, white solid. ESI-MS: 427 (MH$^+$).

3-{6-[[(Carboxymethoxy)acetyl](methyl)amino]-2-methyl-1,3-benzothiazol-3-ium-3-yl}propane-1-sulfonate (23). The yield was 64%, white solid. ESI-MS: 417 (MH$^+$).

Sodium 3-{(2Z)-5-{[(Carboxymethoxy)acetyl]methylamino}-2-[(2E,4Z)-4-(1,1-dioxido-3-oxo-1-benzothien-2 (3H)-ylidene)but-2-enylidene]-3,3-dimethyl-2,3-dihydro-1H-indol-1-yl}propane-1-sulfonate (24) and Sodium 3-{(2Z)-6-{[(Carboxymethoxy)acetyl]-methylamino}-2-[(2E,4Z)-4-(1,1-dioxido-3-oxo-1-benzothien-2(3H)-ylidene)but-2-enylidene]-1,3-benzothiazol-3(2H)-yl}propane-1-sulfonate (25). A mixture of the quaternary salt (22 or 23, 0.5 mmol) and enol ether 9 (0.625 g, 2.50 mmol) in 20 mL of a chloroformacetic acid mixture (1:1) was magnetically stirred at 60° C. under nitrogen. A solution of 0.200 g of sodium acetate in 5 mL of acetic acid was added by drops to the reaction mixture. The stirring was continued for an additional 24 h. After cooling the dye 25 crystallized from the reaction mixture and was separated by filtration and purified by recrystallization from acetic acid. The reaction mixture containing dye 24 was evaporated in a vacuum, and the pure dye was isolated by chromatography over silica gel, eluting with acetone-acetic acid (5:1), followed by recrystallization from acetic acid.

Sodium 3-{(2Z)-5-{[(Carboxymethoxy)acetyl]methylamino}-2-[(2E,4Z)-4-(1,1-dioxido-3-oxo-1-benzothien-2(3H)-ylidene)but-2-enylidene]-3,3-dimethyl-2,3-dihydro-1H-indol-1-yl}propane-1-sulfonate (24). The yield was 60%. $^1$H NMR (500 MHz, DMSO-d6): δ 1.69 (s, 6H, 2×CH3), 2.04 (p, $^3J_{H-H}$=7.0 Hz, 2H, CH$_2$—CH$_2$—CH$_2$), 2.65 (t, $^3J_{H-H}$=7.0 Hz, 2H, CH$_2$—SO$_3$), 3.25 (s, 3H, CH$_3$N), 4.05 (bs, 2H, CH$_2$COOH), 4.19 (bs, 2H, CH$_2$CON), 4.24 (t, $^3J_{H-H}$=7.0 Hz, 2H, CH$_2$—N), 6.4-8.5 (m, 11H). MALDI-FTMS: MNa+ found 689.1203, expected 689.1210.

Sodium 3-{(2Z)-6-{[(Carboxymethoxy)acetyl]methylamino}-2-[(2E,4Z)-4-(1,1-dioxido-3-oxo-1-benzothien-2(3H)-ylidene)but-2-enylidene]-1,3-benzothiazol-3(2H)-yl}propane-1-sulfonate (25). The yield was 54%. $^1$H NMR (500 MHz, DMSO-d$_6$): δ 2.09 (p, $^3J_{H-H}$=7.0 Hz, 2H, CH$_2$—CH$_2$—CH$_2$), 2.67 (t, $^3J_{H-H}$32 7.0 Hz, 2H, CH$_2$—SO$_3$), 3.27 (s, 3H, CH$_3$), 4.09 (bs, 2H, CH$_2$COOH), 4.17 (bs, 2H, CH$_2$—CON), 4.57 (t, $^3J_{H-H}$=7.0 Hz, 2H, CH$_2$—N), 6.8-8.0 (m, 11H). ESIMS: 635 (M−Na+2H)+.

Sodium 3-{(2Z)-5-[({2-[(2,5-Dioxopyrrolidin-1-yl)oxy]-2-oxoethoxy}acetyl)methylamino]-2-[(2E,4Z)-4-(1,1-dioxido-3-oxo-1-benzothien-2(3H)-ylidene)but-2-enylidene]-3,3-dimethyl-2,3-dihydro-1H-indol-1-yl}propane-1-sulfonate (I—SO—OSu, 4f) and Sodium 3-[(2E)-6-[({2-[(2,5-Dioxopyrrolidin-1-yl)oxy]-2-oxoethoxy}acetyl)-methylamino]-2-[(2E,4Z)-4-(1,1-dioxido-3-oxo-1-benzothien-2(3N)-ylidene)but-2-enylidene]-1,3-benzothiazol-3(2N)-yl]propane-1-sulfonate (S—SO—OSu, 2f). To a solution of 0.50 mmol of free acid dye from the previous synthesis in 10 mL of dimethylformamide were added tetramethyl(succinimido)uronium tetrafluoroborate (301 mg, 1.00 mmol) and diisopropylethylamine (200 mg). The solution was stirred under nitrogen at room temperature for 1 h. The solvent was removed under high vacuum. The residue was treated with acetone (5 mL), and ether (25 mL) was added to precipitate the reactive dye.

Sodium 3-{(2Z)-5-[({2-[(2,5-Dioxopyrrolidin-1-yl)oxy]-2-oxoethoxy}acetyl)methylamino]-2- [(2E,4Z)-4-(1,1-dioxido-3-oxo-1-benzothien-2(3H)-ylidene)but-2-enylidene]-3,3-dimethyl-2,3-dihydro-1H-indol-1-yl}propane-1-sulfonate (I—SO—OSu, 4f). The yield was 90%. $^1$H NMR (500 MHz, DMSO-d$_6$): δ 1.69 (s, 6H, 2×CH$_3$), 2.04 (p, $^3J_{H-H}$=7.0 Hz, 2H, CH$_2$—CH$_2$—CH$_2$), 2.65 (t, $^3J_{H-H}$=7.0 Hz, 2H, CH$_2$—SO$_3$), 2.92 (s, 4H, CH$_2$CH$_2$), 3.25 (s, 3H, CH$_3$N), 4.12-4.17 (m, 4H, CH$_2$CON, CH$_2$COOSu), 4.24 (t, $^3J_{H-H}$=7.0 Hz, 2H, CH$_2$—N), 6.4-8.5 (m, 11H). ESI-MS: 742 (M−Na+2H)+.

Sodium 3-[(2E)-6-[({2-[(2,5-Dioxopyrrolidin-1-yl)oxy]-2-oxoethoxy}-acetyl)methylaminol]-2-[(2E,4Z)-4-(1,1-dioxido-3-oxo-1-benzothien-2(3H)-ylidene)but-2-enylidene]-1,3-benzothiazol-3(2H)-yl]propane-1-sulfonate (S—SO—OSu, 2f). The yield was 87%. $^1$H NMR (500 MHz, DMSO-d$_6$): δ 2.09 (p, $^3J_{H-H}$=7.0 Hz, 2H, CH$_2$—CH$_2$—CH$_2$), 2.67 (t, $^3J_{H-H}$=7.0 Hz, 2H, CH$_2$—SO$_3$), 2.80 (s, 4H, CH$_2$CH$_2$), 3.26 (s, 3H, CH$_3$), 4.13-4.19 (m, 4H, CH$_2$CON CH$_2$COOSu), 4.57 (t, $^3J_{H-H}$=7.0 Hz, 2H, CH$_2$—N), 6.4-8.4 (m, 11H). ESI-MS: 732 (M−Na+2H)+.

Preparation of Sodium 3-[(2Z)-6(Acetylamino)-2-[(2E)-4-(1,3-dimethyl-4,6-dioxo-2-thioxotetrahydropyrimidin-5(2M)-ylidene)but-2-enylidene]-1,3-benzothiazo]-3(2H)-yl] propane-1-sulfonate (1g). The suspension of dye 1e (200 mg) in 10 mL of acetic anhydride was stirred at 80° C. for 12 h under nitrogen. After cooling the crude dye was separated by filtration and purified by recrystallization from methanol. The yield was 120 mg (55%). $^1$H NMR (400 MHz, DMSO-d$_6$): δ 1.90 (s, 3H, CH$_3$CO), 2.00 (p, $^3J_{H-H}$=7.0 Hz, 2H, CH$_2$—CH$_2$—CH$_2$), 2.55 (t, $^3J_{H-H}$=7.0 Hz, 2H, CH$_2$—SO3), 3.61 (s, 6H, 2×CH$_3$), 4.56 (t, $^3J_{H-H}$=7.0 Hz, 2H, CH$_2$—N), 6.8-7.8 (m, 7H), 10.56 (1H, NH). MALDI-FTMS: MH+ found 559.0762, expected 559.075.

Preparation of Dyes 1h, 2g, and 4g. Reactions of lodoacetamides 1f, 2e, and 4e with 2-Mercaptoethanol. A 30 mg sample of iodoacetamido dye (1f, 2e, 4e) was added to a solution of 2-mercaptoethanol (30 mg) in 2.0 mL of NaHCO$_3$—Na$_2$CO$_3$ buffer (pH ) 8.0), and the mixture was stirred for 2 h at room temperature. Silica gel TLC (MeOH—H$_2$O, 90:10) showed complete consumption of starting dye. The conjugates were isolated by chromatography on a C18 column using a water-acetonitrile gradient.

Sodium 3-[(2Z)-6-({[(2-Hydroxyethyl]thiolacetyl}amino)-2-[(2E)-4-(1,3-dimethyl-4,6-dioxo-2-thioxotetrahydropyrimidin-5(2H)-ylidene)-but-2-enylidene]-1,3-benzothiazol-3(2H)-yl]propane-1-sulfonate (1h). $^1$H NMR (500 MHz, DMSO-d$_6$): δ 2.03 (p, $^3J_{H-H}$=7.0 Hz, 2H, CH$_2$—CH$_2$—CH$_2$), 2.65 (t, $^3J_{H-H}$=7.0 Hz, 2H, CH$_2$—SO3), 2.80 (t, $^3J_{H-H}$=6.6 Hz, 2H, CH$_2$S), 3.40 (s, 2H, COCH$_2$S), 3.60 (s, 6H, 2×CH$_3$), 3.64 (q, $^3J_{H-H}$=6.6 Hz, 2H, CH$_2$—OH), 4.57 (t, $^3J_{H-H}$=7.0 Hz, 2H, CH$_2$—N), 4.94 (bs, 1H, OH), 6.8-8.0 (m, 11H), 10.47 (s, 1H, NHCO). ESIMS: 613 (M−Na+2H)+;

Sodium 3-[(2Z)-6-({[(2-Hydroxyethyl)thio]acetyl}amino)-2-[(2E,4Z)-4-(1,1-dioxido-3-oxo-1-benzothien-2(3H)-ylidene)but-2-enylidene]-1,3-benzothiazol-3(2H)-yl]propane-1-sulfonate (2g). 1H NMR (500 MHz, DMSO-d6): δ 2.08 (p, $^3J_{H-H}$=7.0 Hz, 2H, CH$_2$—CH$_2$—CH$_2$), 2.66 (t, $^3J_{H-H}$=7.0 Hz, 2H, CH$_2$—SO$_3$), 2.79 (t, J$_{H-H}$=6.6 Hz, 2H, SCH$_2$—CH$_2$), 3.47 (s, 2H, COCH$_2$S), 3.64 (q, $^3J_{H-H}$=6.6Hz, 2H, CH$_2$OH), 4.57 (t, $^3J_{H-H}$=7.0 Hz, 2H, CH$_2$—N), 4.95 (t, $^3J_{H-H}$=6.6 Hz, 1H, OH), 6.6-8.5 (m, 11H), 10.50 (s, 1H, NHCO). MALDIFTMS: MH+ found 645.0464, calculated 645.0458.

Sodium 3-{(2E)-5-({[(2-Hydroxyethyl)thio]acetyl}amino)-2-[(2E,4Z)-4-(1,1-dioxido-3-oxo-1-benzothien-2(3H)-ylidene)but-2-enylidene]-3,3-dimethyl-2,3-dihydro-2,3-dihydro-1H-indol-1-yl}propane-1-sulfonate (4g). $^1$H NMR (500 MHz, DMSO-d$_6$): δ 1.70 (s, 6H, 2×CH3), 2.08 (p, $^3J_{H-H}$=6.9 Hz, 2H, CH$_2$—CH$_2$—CH$_2$), 2.67 (t, $^J_{H-H}$=6.9 Hz, 2H, CH$_2$—SO$_3$), 2.81 (t, $^3J_{H-H}$=6.6 Hz, 2H, CH$_2$—CH$_2$S), 3.43 (s, 2H, COCH$_2$S), 4.26 (t, $^3J_{H-H}$=6.9 Hz, 2H, CH2-N), 6.4-8.3 (m, 11H), 10.31 (s, 1H, NHCO). MALDI-FTMS: MNa+ found 677.1032, calculated 677.1028.

Protein Labeling. A fragment of Wiskott Aldrich Syndrome Protein (WASP, residues 201-320), mutated to contain a single cysteine (F271C), was labeled with S—SO—IAA, Cy3,71 or Cy571 dyes. A stock solution of the dye in DMSO (10-20 mM) was added to 200 μL of protein solution (200 μM in sodium phosphate buffer, pH=7.5) to produce a final dye concentration of 1-2 mM. The reaction mixture was incubated for 4 h at room temperature then quenched by addition of 1 μL of mercaptoethanol. The reaction mixture was spun at 12,000 rpm for 2 min to remove any precipitates that might have formed during the reaction, and the supernatant was purified using G25 Sepharose gel filtration. The dye-protein adduct was clearly separated from free dye during gel filtration. Purity of the conjugates was confirmed by SDS-PAGE electrophoresis. No free dye was seen in purified protein conjugates. Control samples of free dye were clearly visible on the gel at a lower molecular weight than protein. Conjugates formed single, highly colored fluorescent protein bands with molecular weights corresponding to the WASP fragment. The dye-to-protein ratio was calculated by measuring protein and dye concentrations using absorbance spectroscopy as previously described. Haugland, R. P. *Handbook of*

*Fluorescent Probes and Research Chemicals*; Molecular Probes Inc.: Eugene, Oreg., 1996. In each case this ratio was between 0.9 and 1.0. Concentration of CBD was independently confirmed by Coomassie Plus assay (Pierce) calibrated with bovine serum albumin as a standard. Aliquots of the labeled CBD (15-50 $l$M) were stored at −80° C. No significant loss of binding ability was observed after 6 months of storage.

Analysis of Cdc42 Activation. A solution of the WASP conjugate (300 nM) in a assay buffer (50 mM Tris-HCl, pH 7.6, 50 mM NaCl, 5 mM MgCl$_2$, 1 mM DTT) was mixed 1:1 (v/v) with solutions of Cdc42, pre-equilibrated with 10 mM GDP or GTPγS as described below. Emission at 630 nm and excitation at 600 nm were used to acquire excitation and emission spectra, respectively. For nucleotide dependence, Cdc42 (500 nM) was preincubated with varying concentrations of GTPγS (1-500 nM).

Photo-bleaching. All samples contained 1 mM dye in a final volume of 10 mL. For nitrogen and oxygen saturation the samples were bubbled with solvent-saturated gas for 30 min. A 90 W halogen tungsten lamp was employed for irradiation, with a fan used for cooling. The temperature of samples was 25±1° C. during reactions. The absorption spectrum of each sample was measured before irradiation and after every 10 h period. For the trapping experiment thioanisole (1.0 M) was added to oxygen-saturated butanol solution of dye 1b. After 60 h of irradiation the reaction mixture was analyzed by GC-MS for products formed. The products, methylphenylsulfoxide and methylphenyl sulfone, were identified by comparison with authentic samples.

Results

Merocyanine Dyes with Improved Water Solubility and Reduced Aggregation in Water. The goal was to make useful, water-soluble derivatives of the 1a dye. New analogues were made, for example, by substitution of a quaternary amino group in the 1a dye with a much more hydrophilic sulfonato group (—SO$_3$Na). In some analogues, cysteine-selective iodoacetamido groups were also added for covalent attachment to proteins. The solubility of the sulfonato analogues 1c and 1d was significantly improved over the original structure 1a, and the ability of dye 1d to attach covalently to cysteine was confirmed by reacting it with, β-mercaptoethanol. However, the new dyes still could not be dissolved in aqueous buffers at concentrations suitable for protein labeling. Labeling was accomplished only by including greater than 5% DMSO as cosolvent. Attempts to label a fragment of Wiskott Aldrich Syndrome Protein (WASP) containing a single cysteine showed that it was still very difficult to remove noncovalently bound dye from the labeled protein (dialysis, size exclusion, and ion-exchange chromatography were all unsuccessful).

The protein conjugates contained more than one equivalent of dye even when labeling was done at low dye concentrations, yet the fluorescence of the conjugates was extremely weak. These data led us to hypothesize that the dyes were forming non-fluorescent H-aggregates in water, as reported previously for other merocyanines. Wurthner et al. *Angew. Chem., Int. Ed.* 2000, 39, 1978-1981; Lu et al. *J. Am. Chem. Soc.* 1999, 121, 8146-8156; and Valdes-Aguilera et al. *Acc. Chem. Res.* 1989, 22, 171-177. These may have been the actual reactive species in aqueous solution. Analysis of dye 1c absorbance spectra supported the formation of H-aggregates. The spectrum in water differed in shape from spectra in more hydrophobic solvents such as methanol or butanol, and aqueous spectra showed a concentration-dependent shift to a shorter wavelength peak at 515 nm (FIG. 1), consistent with the formation of non-fluorescent H aggregates. Mandal et al. *J. Phys. Chem. A* 1999, 103, 8156-8159. Furthermore, the excitation and absorbance spectra were different, indicating the presence of multiple species in water (FIG. 1). Together, these data suggested that the essentially planar dye was aggregating to reduce the exposure of its hydrophobic surfaces to water, as previously described for other merocyanine dyes. Nakahara et al. *J. Phys. Chem.* 1986, 90, 6144-6148.

Figure 3:
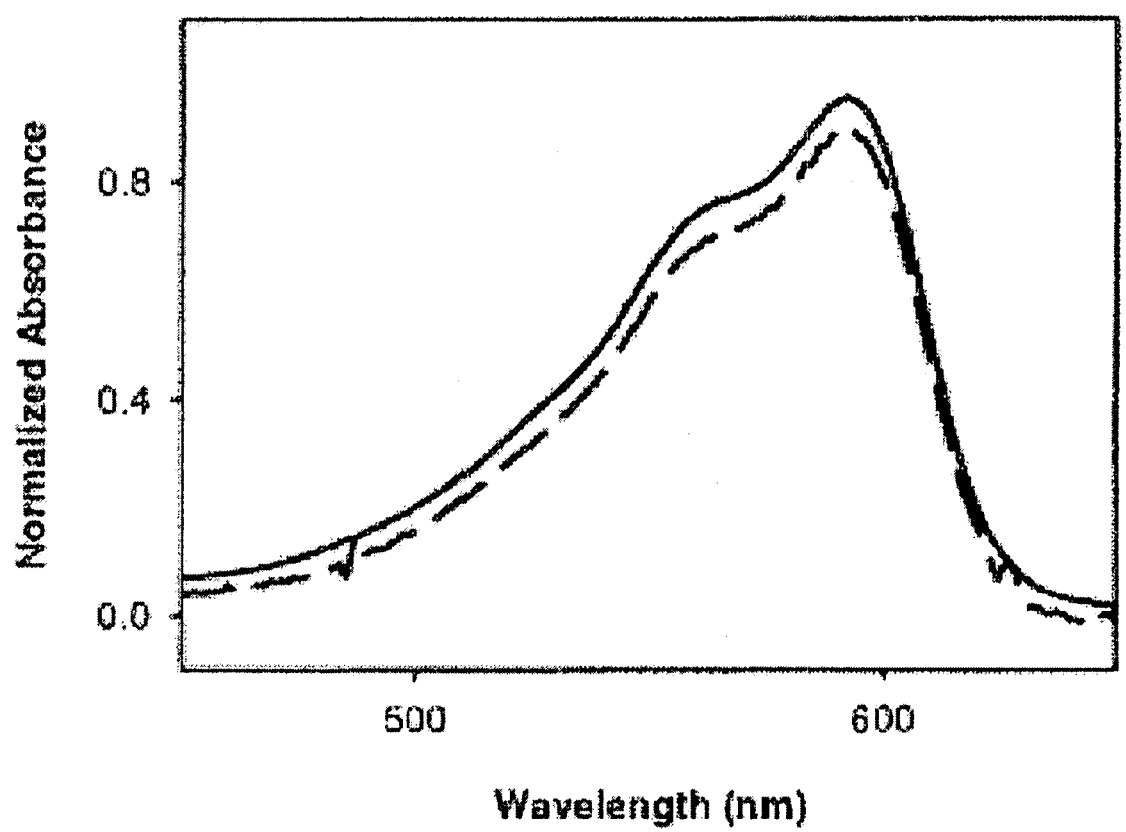
FIG. 3 provides an absorbance spectrum of the I—SO dye 4b in water at 1.25 µM (-) and 250 µM ( - - - ).

Such aggregation can be energetically favorable only if the planar dye molecules can get closer to each other than the size of a water molecule. To decrease aggregation, we incorporated bulky, nonplanar substituents with tetragonal geometry in the aromatic rings to make stacking unfavorable (see Formulae 1-4). This strategy allowed the dyes to retain a relatively hydrophobic character using geminal dimethyl and/or sulfonato groups. The effects of the groups on aggregation were assessed by incorporating them individually or in combination into a series of dyes (1c, 2b, 3b, 4b; see FIG. 2). Dyes 2b and 3b each had one of the tetragonal substituents, while dye 4b combined both in one structure. As shown in FIG. 2, the ratio $A_H/A_M$ ($A_H$ is absorbance of H-aggregates and $A_M$ is absorbance at longer wavelength from monomeric dye) showed that the tetragonal groups strongly decreased aggregation. The aqueous absorbance spectrum of dye 4b, which contained both out-of-plane substituents, did not depend on concentration, indicating that it did not aggregate even at concentrations greater than 250 μM, well within the range typically used for protein labeling (FIG. 3). Introduction of the nonplanar substituents not only reduced aggregation but also greatly improved the dyes' water solubility. Dye 4b showed excellent water solubility presumably because the substituents made the dye less symmetric and/or because H-aggregation contributes to poor water solubility.

In summary, the new fluorophores showed excellent water solubility and little aggregation and retained substantial hydrophobic character for interaction with proteins. They were named on the basis of the heterocycles at their termini, using a previous nomenclature system described in Hahn, K. M.; Waggoner, A. S.; Taylor, D. L. *J. Biol. Chem.* 1990, 265, 20335-20345.

Attributes for Sensing Protein Activity in Vivo: Spectral Properties and Chemical and Photochemical Stability. The fluorophores in the S-TBA, S—SO, I-TBA, and I—SO dyes all absorb light at long wavelengths advantageous in live cell imaging (Table 2).

TABLE 2

Photophysical Properties of Dyes in Various Solvents

| dye | solvent | dielectric constant | $\eta^a$ cP | Abs. $\lambda_{max}$, nm ($\epsilon^b$) | Emission $\lambda_{max}$, nm | $\Phi^c$ | $\epsilon \times F$ |
|---|---|---|---|---|---|---|---|
| 1b S-TBA | C$_6$H$_6$ | 2.27 | 0.604 | 600 (184000) | 617 | 0.37 | 68000 |
| 1b S-TBA | OcOH | 3.4 | 7.288 | 598 (220000) | 615 | 0.52 | 115000 |
| 1b S-TBA | BuOH | 17.8 | 2.544 | 595 (188000) | 613 | 0.26 | 49000 |
| 1b S-TBA | MeOH | 32.6 | 0.793 | 583 (134000) | 606 | 0.13 | 18000 |
| 1b S-TBA | DMF | 36.7 | 0.794 | 595 (194000) | 613 | 0.32 | 62000 |
| 2a S-SO | C$_6$H$_6$ | 2.27 | 0.604 | 591 (152000) | 617 | 0.16 | 24000 |

TABLE 2-continued

Photophysical Properties of Dyes in Various Solvents

| dye | solvent | dielectric constant | $\eta^a$ cP | Abs. $\lambda_{max}$, nm ($\epsilon^b$) | Emission $\lambda_{max}$, nm | $\Phi^c$ | $\epsilon \times F$ |
|---|---|---|---|---|---|---|---|
| 2a S-SO | OcOH | 3.4 | 7.288 | 606 (168000) | 623 | 0.17 | 29000 |
| 2a S-SO | BuOH | 17.8 | 2.544 | 604 (163000) | 622 | 0.12 | 20000 |
| 2a S-SO | MeOH | 32.6 | 0.793 | 598 (143000) | 617 | 0.05 | 7000 |
| 2a S-SO | DMF | 36.7 | 0.794 | 602 (173000) | 619 | 0.22 | 38000 |
| 4a I-SO | C$_6$H$_6$ | 2.27 | 0.604 | 571 (109000) | 603 | 0.42 | 46000 |
| 4a I-SO | OcOH | 3.4 | 7.288 | 587 (125000) | 617 | 0.98 | 123000 |
| 4a I-SO | BuOH | 17.8 | 2.544 | 587 (134000) | 618 | 0.54 | 72000 |
| 4a I-SO | MeOH | 32.6 | 0.793 | 586 (143000) | 615 | 0.08 | 12000 |
| 4a I-SO | DMF | 36.7 | 0.794 | 586 (143000) | 615 | 0.97 | 140000 |
| 3a I-TBA | C$_6$H$_6$ | 2.27 | 0.604 | 584 (127000) | 605 | 0.20 | 26000 |
| 3a I-TBA | OcOH | 3.4 | 7.288 | 590 (180000) | 609 | 0.99 | 178000 |
| 3a I-TBA | BuOH | 17.8 | 2.544 | 589 (190000) | 609 | 0.61 | 116000 |
| 3a I-TBA | MeOH | 32.6 | 0.793 | 583 (173000) | 603 | 0.26 | 45000 |
| 3a I-TBA | DMF | 36.7 | 0.793 | 589 (183000) | 611 | 0.94 | 172000 |

[a]Solvent shear viscosity (from Onganer, Y.; Yin, M.; Bessire, D.; Quitevis, E. J. Phys. Chem. 1993, 97, 2344-2354).
[b]Molar extinction coefficient, error ±5%.
[c]Quantum yield of fluorescence, error ±10%.

Figures 4A, 4B:
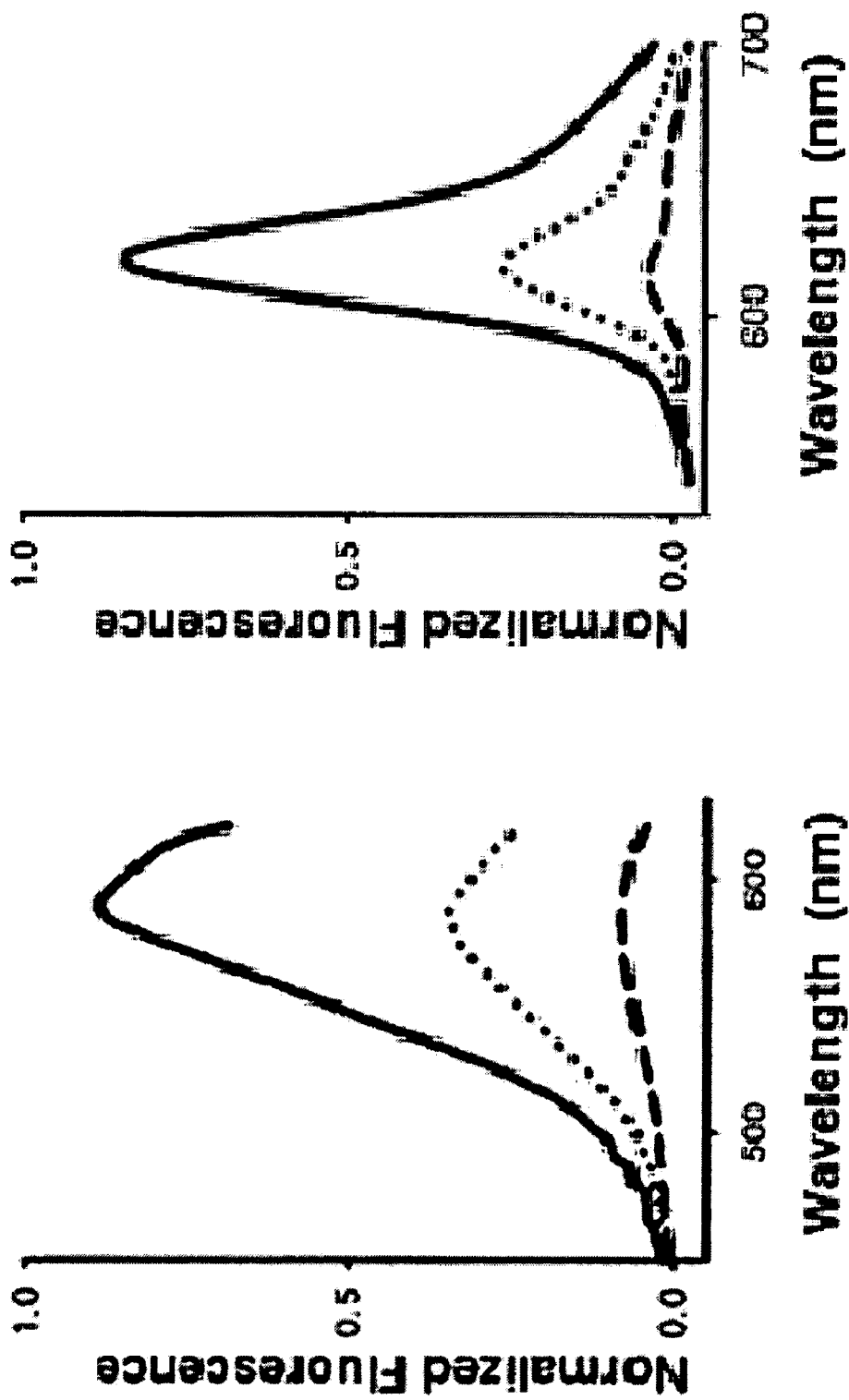
FIG. 4A-B provides normalized excitation and emission spectra of S-SO dye 2b in different solvents: butanol (-), methanol (•••), and water ( - - - ). Excitation spectra acquired with emission at 640 nm. Emission spectra acquired with excitation at 530 nm. C(2b) =0.01 µM.

Their extinction coefficients and quantum yields were characterized in different solvents (Table 2, FIGS. 4, 5), showing a dramatic solvent-dependent change in fluorescence intensity, which was primarily due to changes in quantum yield. For I—SO, the quantum yield changed more than 12-fold, from 0.97 in DMF to 0.08 in methanol. In the same solvents, S—SO showed a 4.4-fold change in quantum yield. Changes were even greater in water, but this was difficult to quantify precisely for S—SO due to some remaining aggregate formation. The dyes are extraordinarily bright when in a nonpolar environment, comparing very favorably with the brightest dyes currently used in living cells. Although their quantum yields are solvent sensitive, the dyes showed only moderate changes in absorbance and emission maxima with changes of solvent polarity.

Dyes used in living cells must be photostable to provide many sequential images and to obtain sufficient light from minimal amounts of exogenous labeled material. The photostability of the new dyes was characterized by exposing them to constant illumination from a tungsten lamp filtered through glass, a broad spectrum light source that provided essentially equal intensity throughout the spectral range where the dyes would be irradiated in vivo. A fan was used to prevent heating, and dye solutions were adjusted for equal maximal absorbance, kept below 1 µM to minimize the inner filter effect. Photo-bleaching of dyes 1b, 2a, 3a, and 4a was compared in two solvents that do not lead to dye aggregation, methanol and butanol, so that all reactions could be attributed to uniformly monomeric dye. Photo-bleaching followed first-order kinetics in all cases.

Figure 6A:
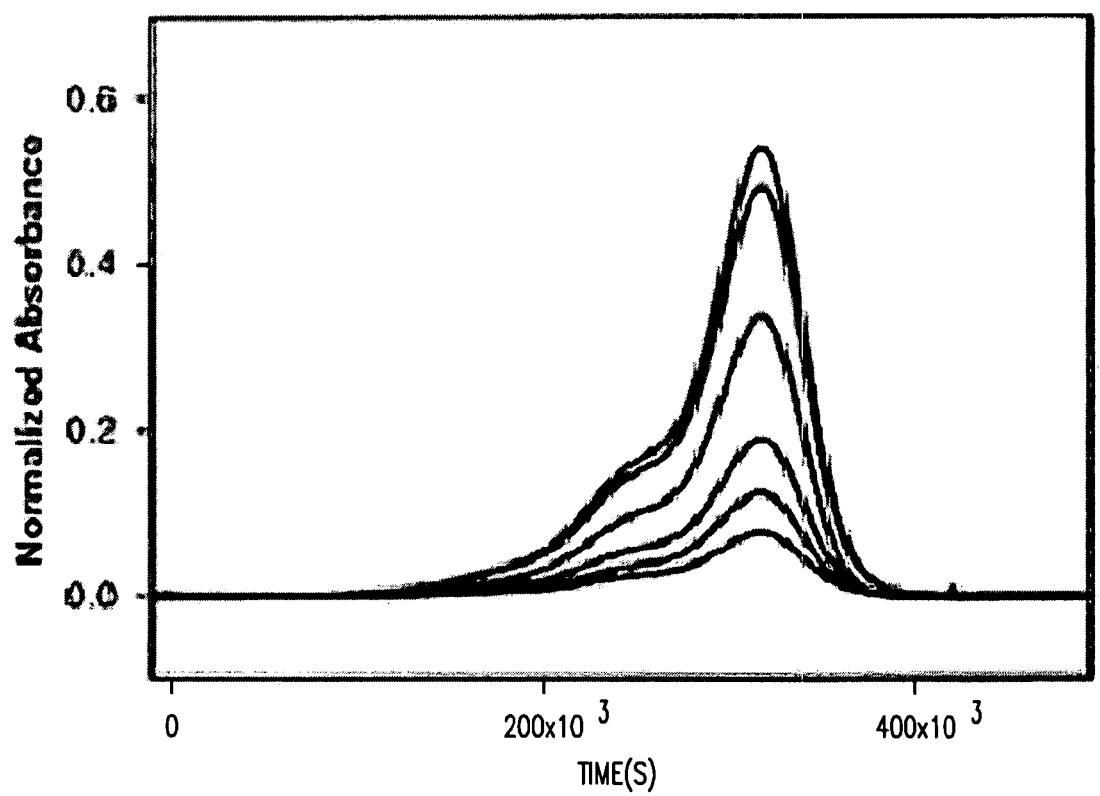
FIGS. 6A-B illustrate the absorbance properties of the S-TBA dye 1b.
Figure 6B:
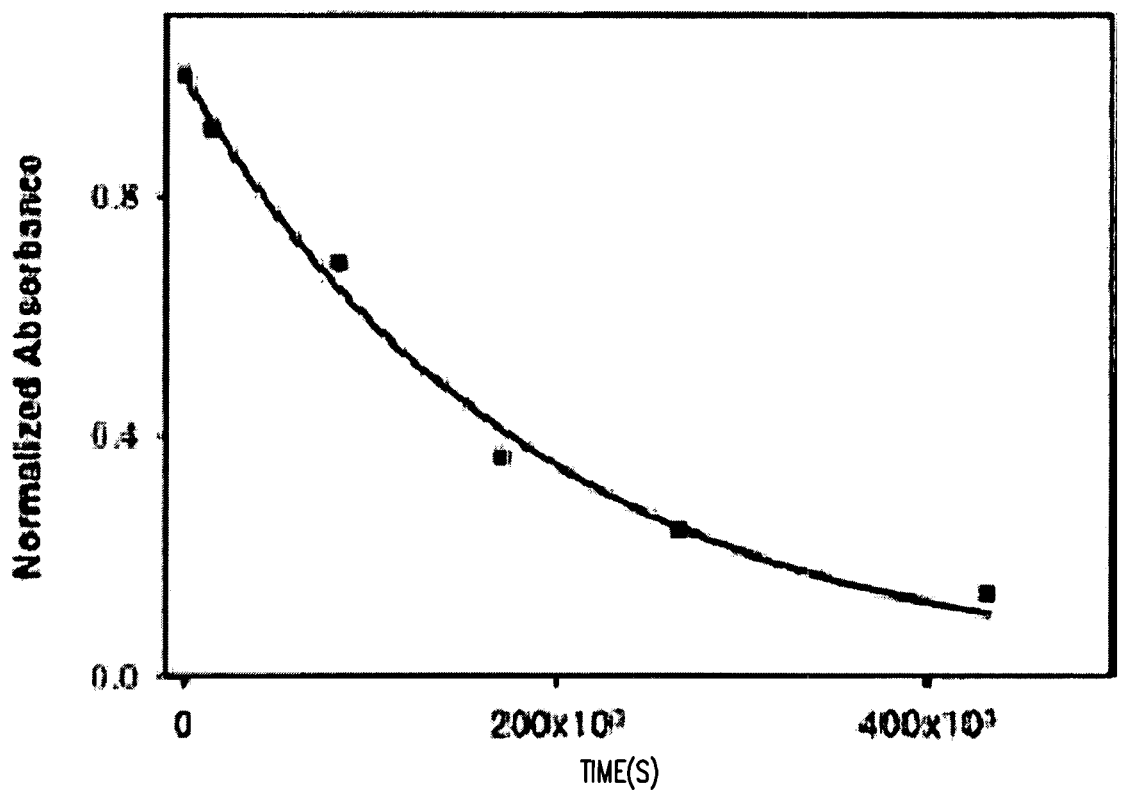

The bleaching rates were compared to Cy5, a frequently used live cell imaging dye with known photo bleaching rates. Toomre, D.; Manstein, D. J. *Trends Cell Biol.* 2001, 11, 298-303. The results of this comparison are provided in Table 3 and FIG. 6.

TABLE 3

Absolute Rate Constants of Dye Photo-bleaching[a]

| | $k_{ph} \times 10^6$, s$^{-1}$ | | |
|---|---|---|---|
| dye | MeOH | BuOH | $\Phi T^b$ |
| I-SO, 4a | 0.28 | 0.65 | |
| I-TBA, 3a | 0.18 | 0.78 | 0.003 |
| S-SO, 2a | 3.0 | 5.2 | |
| S-TBA, 1b | 4.3 | 5.2 | 0.008 |
| Cy5 | 1.0 | 0.77 | |

[a]The error in $k_{ph}$ is ±10%.
[b]Quantum yield of triplet state formation in ethanol determined as described in Benniston, A.; Gulliya, K.; Harriman, A. J. Chem. Soc., Faraday Trans. 1997, 93, 2491-2501.

As shown in Table 3, I—SO showed excellent photostability, bleaching with only 28% the rate of Cy5 in methanol.

Bleaching most likely occurred through one of three possible mechanisms, generating reactive oxygen species that destroyed the fluorophore. The triplet excited state of the dye could react with oxygen to produce singlet oxygen, or electron transfer from the singlet excited state dye could generate a reactive oxygen radical anion. Kanony, C.; Akerman, B.; Tuite, E. *J. Am. Chem. Soc.* 2001, 123, 7985-7995. The third possible mechanism is a free radical chain reaction between the ground state of the dye and oxygen, initiated by photogenerated peroxides. Such an autoxidation is common for olefins. Collman, J. P.; Kubota, M.; Hosking, J. W. *J. Am. Chem. Soc.* 1967, 89, 4809-4811; Zombeck, A.; Hamilton, D. E.; Drago, R. S. *J. Am. Chem. Soc.* 1982, 104, 6782-6784. However, it was unlikely in these systems, because neither a long induction period nor a strong dependence on oxygen concentration was observed.

To differentiate between the other two possibilities, the reaction was repeated in the presence of thioanisole, a trapping agent that reacts with singlet oxygen or superoxide to produce a sulfoxide or a sulfone. Foote, C. S.; Peters, J. W. *J. Am. Chem. Soc.* 1971, 93, 3795-3796; Correa, P. E.; Hardy, G.; Riley, D. P. *J. Org. Chem.* 1988; 53, 1695-1702. Butanol solutions of 1b generated 90% phenylmethylsulfoxide and 10% phenylmethyl sulfone, consistent with a mechanism mediated by singlet oxygen. Watanabe, Y.; Kuriki, N.; Ishiguro, K.; Sawaki, Y. *J. Am. Chem. Soc.* 1991, 113, 2677-2682. Formation of singlet oxygen was also supported by a 7.5-fold increase in bleaching rates upon switching from methanol to deuterated methanol-d4 40 and by the fact that rates were highest for dyes containing the most sulfur. Sulfur can enhance triplet formation through the inner heavy atom effect. Benniston, A.; Gulliya, K.; Harriman, A. *J. Chem. Soc., Faraday Trans.* 1997, 93, 2491-2501: Turro, N. *J. Tetrahedron* 1985, 41, 2089-2098. Sparging the solution with nitrogen did not affect the rate because very small concentrations of dissolved oxygen are sufficient to saturate the reaction.

Altering the pH between 6 and 9 had no effect on the dye's absorbance, fluorescence intensity, or excitation and emission maxima. Incubation in aqueous buffers at pH 6 or 9 for 3 h at room temperature had no effect.

Derivatives for Site-Specific Protein Labeling. The fluorophores S—SO and I—SO, which showed the most favorable characteristics for live biosensors, were derivatized to make reactive forms which could be site-specifically attached to proteins. Analogues were made with succinimidyl ester for attachment to lysine or with iodoacetamide for selective reaction with cysteine. Use of these groups for site-specific protein labeling is well established. Dent, A.; Aslarn, M. *Bioconjugation* 1998, 364-482. During synthesis of the reactive dyes (FIG. 8), starting materials carried an amino group, which was used for attachment of side chains at the end of the synthesis. It proved challenging to find an amine protecting group which could survive the quatemization reaction in the initial steps of the synthesis, yet could be removed without destroying the completed fluorophore. This hurdle was overcome using novel deprotection conditions for the Fmoc group, which could be cleanly removed with sodium acetate in dimethyl sulfoxide (rather than the stronger bases such as piperidine which are usually used). A 3-sulfonatopropyl substituent was also incorporated in each dye during these syntheses to further enhance water solubility.

Attachment of reactive side chains affected the quantum yields of both S—SO and I—SO dyes (Table 4).

TABLE 4

Photophysical Properties of Reactive Forms of Merocyanine Dyes

| dye | solvent | absorption $\lambda_{max}$, nm ($\epsilon^a$) | emission $\lambda_{max}$, nm | $\Phi^b$ | $\epsilon \times \Phi$ |
|---|---|---|---|---|---|
| 2e S-SO-IAA | H$_2$O | 552, 592 | 618 | c | c |
| 2e S-SO-IAA | MeOH | 610 (140000) | 628 | 0.034 | 3000 |
| 2e S-SO-IAA | BuOH | 618 (160000) | 636 | 0.06 | 9600 |
| 2f S-SO-OSu | H$_2$O | 552, 591 | 618 | c | c |
| 2f S-SO-OSu | MeOH | 603 (142000) | 621 | 0.06 | 9000 |
| 2f S-SO-OSu | BuOH | 608 (134000) | 626 | 0.12 | 28000 |
| 2g S-SO-βME | MeOH | 610 (138000) | 629 | 0.054 | 8000 |
| 4e I-SO-IAA | H$_2$O | 599 (143000) | 630 | 0.004 | 600 |
| 4e I-SO-IAA | MeOH | 601 (138000) | 634 | 0.01 | 1400 |
| 4e I-SO-IAA | BuOH | 607 (150000) | 639 | 0.06 | 9000 |
| 4f I-SO-OSu | H$_2$O | 594 (150000) | 616 | 0.01 | 1500 |
| 4f I-SO-OSu | MeOH | 586 (140000) | 620 | 0.05 | 7000 |
| 4f I-SO-OSu | BuOH | 590 (134000) | 623 | 0.19 | 26000 |
| 4g I-SO-βME | H$_2$O | 600 (140000) | 620 | 0.02 | 3000 |
| 4g I-SO-βME | MeOH | 601 (140000) | 621 | 0.04 | 6000 |
| 4g I-SO-βME | BuOH | 609 (142000) | 628 | 0.12 | 17000 |

$^a$Molar extinction coefficient, error ±5%.
$^b$Quantum yield of fluorescence, error ±10%.
$^c$Not determined because of aggregation in water.

Although all side chains were attached to the fluorophore via an amide linkage, the effects were very different for each side chain and fluorophore. For example, when adding succinimidyl esters to the fluorophores, the quantum yield in methanol did not change for S—SO, yet decreased 38% for I—SO. The iodoacetamido group decreased the quantum yield of both fluorophores (32% decrease for S—SO, 87% decrease for I—SO in methanol). Such a large decrease in the brightness of the I—SO iodoacetamido would severely limit its utility. The decrease may have been caused by the presence of iodine, which is known to quench fluorescence. McGlynn, S. P.; Azumi, T.; Kinoshita, M. *Molecular Spectroscopy of the Triplet State*; Prentice Hall: Englewood Cliffs, N.J., 1969. If this was so, iodine was lost during the reaction with protein, so this source of reduction in quantum yield would not be a problem. The effect of iodine on fluorescence was tested by reacting the I—SO and S—SO dyes with β-mercaptoethanol (dyes 2g, 4g, Table 4), which returned the quantum yield of S—SO to that of the underivatized fluorophore, and that of I—SO to half that of the unaltered fluorophore.

To further explore the mechanisms by which amine substituents affected quantum yield, S-TBA dyes bearing different substituents were characterized (Table 5). Attachment of an underivatized amino group directly to the fluorophore reduced the dye's extinction coefficient by 63% and the quantum yield by >13-fold. However, this effect was nearly eliminated when the amine was acetylated, as in the final reactive dye derivatives.

Figure 7:
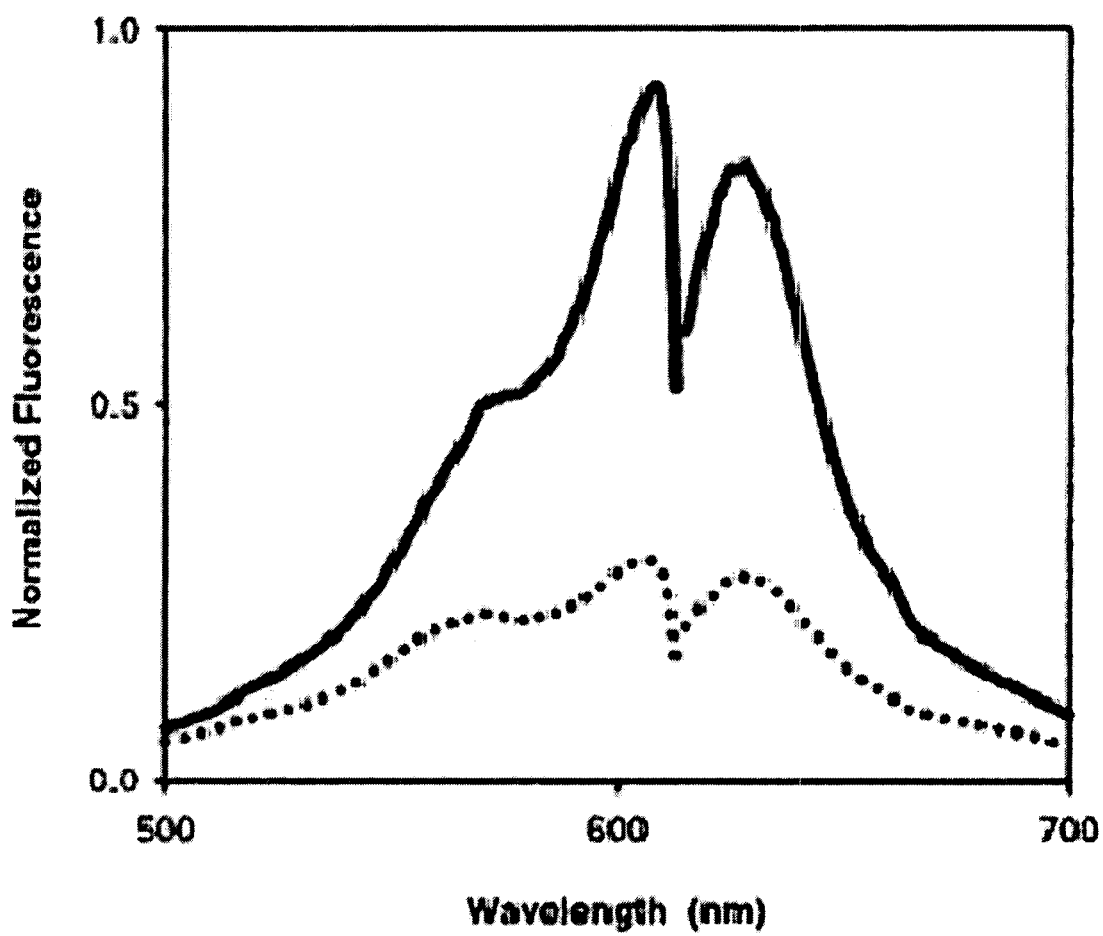
FIG. 7 provides excitation and emission spectra of the S—SO dye attached to a fragment of Wiskott Aldrich Syndrome Protein (WASP) in the presence of GDP-Cdc42 (•••) and GTPγS-Cdc42 (-). As shown, binding of the biosensor to Cdc42 results in changes in the fluorescence spectrum. Excitation spectra were acquired with emission at 630 nm, emission spectra with excitation at 600 nm. [CBD]=150 nM, [Cdc42]=300 nM, [GNP]=10 µM.

S—SO and I—SO in a Biosensor of Cdc42 Activation. The ability of the S—SO and I—SO dyes to respond to changes in protein environment was demonstrated by using these dyes to make a novel biosensor of Cdc42 activation. Wiskott Aldrich Syndrome Protein (WASP) binds only to the activated, GTP-bound form of Cdc42, not to the GDP-bound form. Machesky, L.; Insall, R. *J. Cell. Biol.* 1999, 146, 267-272. A fragment of WASP that retains this selective binding ability (residues 201-320 in the original protein) was derivatized with S—SO dye 2e. Guided by the crystal structure of the WASP-Cdc42 complex (Abdul-Manan et al., *Nature* 1999, 399, 379-383), a cysteine was introduced into the fragment to attach the dye where it could interact with several hydrophobic amino acids (F271C mutation of WASP fragment). The labeled WASP fragment showed a 300% increase in fluorescence intensity when incubated with activated Cdc42, but not with GDP-bound, inactive Cdc42 (FIG. 7). Moreover, the apparent equilibrium binding constant for Cdc42 (150±50 nM) was measured in vitro by titrating a fixed concentration of the labeled WASP fragment with various amounts of cdc42-GTPγS. This value is in good agreement with the results of Kim et al. (*Nature* 2000, 404, 151-158)(133±9 mM) for the WASP-Cdc42 interaction and indicative that the binding properties of the WASP domain were not greatly affected by incorporation of the solvent-sensitive fluorophore into the WASP fragment.

Further studies were conducted using the I—SO dye 4b attached at position F271 C of the WASP fragment. This biosensor had properties similar to the S—SO biosensor described above. Like the S—SO biosensor, the I—SO dye showed the greatest fluorescence response at position 271. In particular, the I—SO-WASP biosensor exhibited a 2.8-fold increase in fluorescence intensity upon binding to Cdc42-GTPγS, relative to either biosensor alone or GDP-loaded Cdc42. The NMR structure of the Cdc42-WASP complex indicated that the dye at position 271 was inserted into a hydrophobic pocket formed from amino acids of both Cdc42 and WASP. To determine the specificity of the biosensor, interactions with different activated GTPases were examined. The biosensor distinguished proteins closely related to Cdc42 from other members of the Rho family. It did not interact with RhoA or Rac at concentrations well above physiological levels, but responded to both Cdc42 and the closely related protein TC10, which bind WASP with similar affinity.

The I—SO labeled WASP fragment provided a straightforward means to assay Cdc42 activation in cell lysates. By simply adding the biosensor to the lysate, the fluorescence readout of Cdc42 activation. This method was used to determine the kinetics of Cdc42 activation in neutrophils after stimulation with chemoattractant fMetLeuPhe (FMLP) peptide. Results obtained paralleled those previously reported using well-established methods (Benard et al., J. Biol. Chem. 275: 36457 (2000). Fluorescence of the biosensor was also used to monitor the real-time kinetics of Cdc42 GDP/GTP exchange in vitro. Because the labeled WASP fragment responded to activated Cdc42 through fluorescence intensity modulation, a ratiometric imaging approach was used to correct for effects of varying cell thickness, uneven illumination, and other factors that could affect imaging of dye intensity (Bright et al., Methods Cell Biol. 14: 157 (1989). The biosensor was fused to enhanced green fluorescent protein (EGFP) to provide a fluorescence signal insensitive to Cdc42 binding, but with the same subcellular distribution as the sensitive dye. The dye image could be divided by the EGFP image to normalize changes in dye intensity not originating from Cdc42 binding. A proline-rich region of WASP (amino acids 315 to 321) was also deleted to preclude possible binding to proteins containing SH3 domains. Fluorescence response and Cdc42 binding of the biosensor remained intact after these modifications. It was named Mero-CBD, for the combination of the Cdc42 binding domain with a merocyanine dye.

The biosensor was injected into living fibroblasts, where it showed localized Cdc42 activation even in unstimulated cells, which was highest at cell extensions. In cells expressing constitutively active Cdc42-Q61L (Miller et al., Mol. Cell. Biol. 14: 1075 (1994)), the overall levels of activity shown by MeroCBD were much higher, and activation was distributed throughout the cell.

To show that the dye was not binding nonspecifically to membranes or to other hydrophobic cell components that could produce spurious fluorescence intensity increases, MeroCBD was compared to a control biosensor with severely reduced Cdc42 binding. This mutant biosensor showed no localized activation for either endogenous or dominant positive Cdc42, and showed only slightly increased total activity in cells expressing Cdc42-Q61L. Unlike the MeroCBD biosensor of the invention, simple localization of the CBD-EGFP provided no data relating to Cdc42 activation.

The ability to detect endogenous protein with the high sensitivity provided by the dye was important in studying Cdc42. High sensitivity enabled detection of protein activation at native concentrations, unlike previous fluorescence resonance energy transfer (FRET) biosensors that required overexpression of Cdc42 (Seth et al., Biochemistry 42: 3997 (2003))), and showed more uniform activation. MeroCBD did not require modification of the Cdc42 terminus with a GFP mutant for FRET as was required in previous studies (Itoh et al., Mol. Cell. Biol. 22: 6582 (2002)). Thus, MeroCBD maintained normal regulation by guanosine dissociation inhibitors (GDIs). For information on guanosine dissociation inhibitors see Hoffinan et al., Cell 100: 345 (2000).

Cdc42 is known to be important for maintaining cell polarity in motility (S. Etienne-Manneville, J. Cell. Sci. 117: 1291 (2004))), but the role of localized Cdc42 activation is poorly understood. Cdc42 promotes leading-edge extension through activation of Rac and of WASP, which causes Arp2/3 to nucleate actin filaments. See Bishop et al. Biochem J. 348: 241 (2000); Higgs et al. J.Cell. Biol. 150: 1311(2000). Cdc42 also induces the fine cell extensions known as filopodia. See, Nobes et al., Biochem. Soc. Trans. 23: 456 (1995); Kozma et al., Mol. Cell. Biol. 15:1942 (1995).

The relative spatiotemporal dynamics of Cdc42 activation, protrusion, and filopodia formation were examined in fibroblasts as they attached and spread on fibronectin. At 30 to 45 min after plating, Cdc42 was activated in a thin band at cell edges extending filopodia. No activation was observed within the filopodia themselves. Regions of lower activation sometimes extended into the cell body at the base of filopodia, consistent with studies showing that actin bundles in filopodia extend into the cell body. At 90 to 120 min after attachment, activity became localized within larger dynamic protrusions, and overall activity increased; protrusions had more than twice the average activity of any other region (n=22 cells). See, Nalbant et al., Science 305: 1615 (2004) (which is incorporated in its entirety by reference herein), for images and further details. Controls showed that biosensor levels did not perturb spreading or motility.

Microtubules or actin may direct Cdc42 activation to specific peripheral locations. This possibility was explored by treating cells with the microtubule-depolymerizing agents nocodazole and colchicine, or with cytochalasin D, an inhibitor of actin polymerization. Only nocodazole and colchicine markedly affected peripheral Cdc42 activation. Microtubules may therefore localize interactions between Cdc42 and guanine nucleotide exchange factors by directing vesicle trafficking or regulating events at adhesion complexes.

Cdc42 has been implicated in intracellular trafficking. The MeroCBD biosensor consistently showed activation in the trans-Golgi apparatus of endothelial cells and sometimes also in fibroblasts. Activation in this major secretory compartment suggests that Cdc42 regulates directional sorting or trafficking of polarity cues, or that microtubules mediate trafficking of activated Cdc42 to specific portions of the periphery.

Using the dye's ability to obtain more than a hundred sequential images at low biosensor concentrations, high-resolution kinetic studies of Cdc42 activation were carried during extension and retraction of individual protrusions. Using an algorithm to objectively determine the boundaries of protrusions, the changing areas of individual protrusions were against the protrusions' total activation per unit area. The rise and fall of Cdc42 activity was markedly correlated with both extension and retraction. This close correlation suggested that Cdc42 activation and deactivation could be rate-determining steps for extension and retraction. Alternatively, upstream signals might coordinately inhibit Cdc42 activity while inducing retraction. These possibilities were distinguished by blocking retraction using an inhibitor of Rho kinase (Y27632). This caused protrusions to continue expanding even after Cdc42 activity decreased, indicating that upstream signals (possibly regulated by the microtubule cytoskeleton) control Cdc42 activity and retraction in parallel. Cdc42 activity did not remain elevated during protrusion, suggesting that Cdc42 initiates rather than maintains extension.

Therefore, MeroCBD exemplifies a biosensor approach that combines the ability to sense endogenous molecules with the sensitivity provided by direct excitation of a fluorescent dye. This extends our ability to examine proteins that cannot be derivatized or overexpressed for live cell studies, and enabled detailed kinetic analysis of rapid cellular processes. The biosensor revealed Cdc42 activation in the trans-Golgi compartment, microtubule-dependent activation at the cell periphery but not in filopodia, and tightly coordinated kinetics of cell extension, retraction, and Cdc42 activation.

Spectral Properties Valuable for Live Cell Biosensors. Solvent-sensitive dyes currently used in vitro are poorly suited for use in living cells. They are not sufficiently bright to quantify spectral changes from small amounts of labeled protein, and their short excitation and emission wavelengths damage cells and overlap cellular autofluorescence. To be bright and fluoresce at longer wavelengths, dyes must have extended conjugation, which unfortunately reduces water solubility and leads to self-aggregation. The frequently used dyes designed for use in living cells were specifically selected to be insensitive to their environment, because they are used to quantify protein distribution (i.e., Fluorescein, Rhodamine, Alexa, Cy3/5). In such dyes, solubility problems could be overcome by incorporating charged groups around the dyes' edges. This may not be desirable in dyes that are intended to be used for detecting proteins, because those dyes must interact with hydrophobic protein regions in order to be useful for reporting protein conformational changes. Dyes must interact with the protein surface so that protein conformational changes affect their interactions with water, hydrogen bonding, or hydrophobic interactions. For domain- or antibody-based sensors, dyes must be able to move from water to hydrophobic pockets during protein binding events. Prior to the development of the present dyes, use of solvatochromic dyes to monitor protein activity in vivo was restricted to proteins that could be labeled with hydrophobic dyes in organic cosolvents. Hahn, K. M.; Waggoner, A. S.; Taylor, D. L. *J. Biol. Chem.* 1990, 265, 20335-20345.

For the new dyes described here, solubility problems were overcome while maintaining hydrophobic moieties for protein interaction. Aliphatic or weakly charged substituents were incorporated that projected out of the plane of the aromatic ring to generate merocyanines that were water soluble and showed minimal or no aggregations at concentrations used for protein labeling. Screening structures containing such out-of-plane groups led to the identification of two fluorophores, S—SO and I—SO, which had both the desired solubility and excellent solvent-sensitive spectral properties for reporting protein conformational changes in vivo.

I—SO showed more than a 12-fold change in fluorescence intensity ($\epsilon^*\Phi$), Table 2) in DMF vs. methanol, and S—SO showed a 5.4-fold change in the same solvents. Changes of this magnitude are much larger than any seen in live cell biosensors to date. The magnitude of changes produced in different solvents is useful for comparing different structures and demonstrates potential maximum changes and dye brightness in a biosensor. Nonetheless, it was important to show that the S—SO dye underwent a 3-fold change in florescence intensity in an actual biosensor, the indicator of Cdc42 activation described here. This change is substantially better than that of the majority of biosensors used successfully in living cells to date.

Biosensor Application of the S—SO dye. The utility of the dyes was proven by using them to build a new biosensor that reported activation of endogenous, untagged Cdc42. By examining the crystal structure of the WASP-Cdc42 complex, hydrophobic pockets formed when the two proteins bound were identified. S—SO was attached to an amino acid that would place it in this pocket when a WASP fragment bound to Cdc42. This fragment bound only to activated, GTP-bound Cdc42, producing a 3.0-fold change in fluorescence intensity. Such a change can be readily detected in vivo.

In control experiments where the WASP fragment was labeled with Cy3 and Cy5 fluorophores, no change in fluorescence intensity was observed. These dyes are known to experience a large increase in fluorescence intensity when transferred to more hydrophobic or more viscous environments, but are not sensitive to hydrogen bonding with the solvent. Soper, S. A.; Mattingly, Q. L. *J. Am. Chem. Soc.* 1994, 116, 3744-3752; Ischenko, A. *Russ. Chem. Rev.* 1991, 60, 865-884. Thus, the lack of response with the cyanine-labeled WASP fragments suggests that the present dyes are responding to a change in hydrogen bonding, as they move into the hydrophobic pocket and decrease exposure to water.

Experiments illustrating the construction and use of this biosensor demonstrate the utility of these types of biosensors for studying the many proteins that cannot be modified without severely affecting their biological activity. Thus, the approach provides a valuable alternative in living cells. The dyes will also be valuable when attached directly to proteins, enabling conformational changes to be followed in vivo for proteins incorporated in large molecular machines. For in vitro applications, the dyes provide a substantially brighter signal than current solvent-sensitive fluorophores. Thus they can enhance sensitivity for studying high-affinity binding interactions, small amounts of protein in high-throughput assays, or protein changes that produce only small effects on other dyes.

EXAMPLE 2

Methods for Making and Using Biosensors

This Example illustrates how to make and use the biosensors of the invention. The specific biosensor described here was based on the HIV-1 neutralizing antibody Fab fragment X5, which binds to HIV envelope protein gp120 after forming a complex with the host cell receptor CD4. See Moulard, M. et al., Broadly Cross-reactive HIV-1-Neutralizing Human Monoclonal Fab Selected for Binding to gp120-CD4-CCR5 Complexes. *Proc Natl Acad Sci USA* 99, 6913-6918 (2002).

Materials

The SB medium and phagemid pComb3X employed were obtained as described in Barbas et al., Phage Display: A Laboratory Manual. (Cold Spring Harbor Laboratory Press, Cold Spring Harbor; 2001). Soluble CD4 and IgG 2G12 were obtained from the National Institute of Health AIDS Research and Reference Program (ARRRP); soluble CD4 was also obtained from Progenics Pharmaceuticals, Inc. Gp $120_{BaL}$ was obtained from Quality Biological Inc. (HIV BaL rgp120).

Recombinant DNA Procedures

ScFv X5 mutants were engineered by oligonucleotide site-directed mutagenesis using the QuikChange Kit (Stratagene) with pComb3X vector DNA, encoding wildtype scFv X5, as template. The sequences of the mutant clones were verified by DNA sequencing.

The scFv X5 fragment was in $V_L$-$V_H$ orientation with an 18-residue linker (GGGGS GGGGS GGGGS RSS, SEQ ID NO:26) and a C-terminal $His_6$- and HA-tag.

ScFv X5 Production and Purification

Wild type and mutant scFv X5 fragments were periplasmically expressed using *E. coli* strain TOP 10F' (Invitrogen). The bacterial cultures (4 L) were grown at 37° C. until $A_{600}$=0.8, induced with 1 mM IPTG and expressed at 30° C. overnight. The cells were pelleted by centrifugation and resuspended in lysis buffer (50 mM Sodium phosphate, pH 8, 0.3 M NaCl). Cell disruption was achieved by sonication. After centrifugation for 30 min at 13,000 rpm, the supernatant was incubated with pre-equilibrated Ni—NTA beads (Qiagen, 0.75 ml of resin for one liter of culture) for 2 h at 4° C. The bound scFv X5 molecules were washed with 10 mM imidazole then eluted with 100 mM imidazole in lysis buffer. Fractions containing scFv X5 were pooled and dialyzed into PBS at 4° C. overnight. The yield of purified scFv X5 varied with each mutant and was between 0.2 and 1.2 mg/L of culture medium.

Expression and Purification of Fc-gp120:

Recombinant Fc-gp120 was expressed using glutamine synthetase gene as selection marker. Bebbington, C. R. et al. High-level Expression of a Recombinant Antibody from Myeloma Cells Using a Glutamine Synthetase Gene as an Amplifiable Selectable Marker. *Biotechnology (NY)* 10, 169-175 (1992). The host cells employed were CHO-K1 cells (provided by Aymeric de Parseval and John Elder, TSRI). Selection was performed in glutamine-free Glasgow minimum essential medium (GMEM, Sigma, St. Louis, Mo.) supplemented with 5% Ultra Low IgG Fetal Bovine Serum (GIBCO Invitrogen Corp., Grand Island, N.Y.), MEM non-essential amino acids (Gibco Invitrogen, Grand Island, N.Y.), lmM MEM sodium pyruvate (Gibco-BRL), 500 µM 1-glutamic acid, 500 µM 1-asparagine, 30 µM adenosine, 30 µM adenosine, 30 µM guanosine, 30 µM cytidine, 30 µM uridine, 10 µM thymidine (Sigma), 100 U of penicillin/mL, 100 µg of streptomycin/mL, and 50 L -methionine sulfoximine (Sigma) in a 3-liter spinner flask.

The supernatant was sterile filtered and purified over protein A-Sepharose Fast Flow (Pharmacia, Arlington Heights, Ill.). Fc-gp120 was eluted in 0.1 M citric acid, pH 3.0. The pH of the protein solution was immediately brought to neutrality by the addition of 2 M Tris (pH 9.0), and the protein was dialyzed against PBS. Protein concentrations were determined by absorbance at 280 nm and confirmed by sodium dodecyl sulfate-polyacrylamide gel electrophoresis (SDS-PAGE). Protein yields using this method ranged from 0.5 to 1.5 mg/Liter.

Fluorophore Coupling

The scFv X5 mutants were labeled with Cys-reactive S—SO—IAA and I—SO—IAA dye, respectively, as described above and in Toutchkine et al., Solvent-sensitive Dyes to Report Protein Conformational Changes in Living Cells. *J Am Chem Soc* 125, 4132-4145 (2003). A stock solution of the dye in DMSO (10-20 mM) was added to 500 µl of protein solution (15-100 µM in PBS, pH 7), to produce a 2.5- to 5-fold molar dye excess. The reaction mixture was incubated for 2.5 h at room temperature. The reaction mixture was centrifuged at 12,000 rpm for 2 min to remove any precipitates which might have formed during the reaction, and the supernatant was purified using Sephadex G25 (Amersham Biosciences) or Bio-Gel P2 (Biorad) gel filtration. The dye-protein adduct was clearly separated from free dye during gel filtration. Purity of the conjugates was confirmed by SDS-PAGE. No free dye was seen in purified protein conjugates. Conjugates formed single, colored fluorescent protein bands with molecular weights corresponding to scFv X5. The dye-to-protein ratio was calculated by measuring protein and dye concentrations using absorbance spectroscopy using $\epsilon_{610\,nm}=140,000\,M^{-1}$ for S—SO and $\epsilon_{599\,nm}=143,000\,M^{-1}$ for I—SO, as previously described in Haugland, R. P. Handbook of Fluorescent Probes and Research Products, Edn. Ninth Edition. (Molecular Probes, Inc., Eugene; 2002). Aliquots of the labeled scFv X5 were stored at −80° C.

Expression and Purification of Cdc42 Biosensor:

DNA encoding the Cdc42-binding fragment of human WASP containing the CRIB motif and surrounding amino acids (WASP amino acids 201 to 321) was amplified by PCR from ATCC clone # 99534. This peptide fragment has the following amino acid sequence (SEQ ID NO:27).

```
DIQNPDITSSRYRGLPAPGPSPADKKRSGKKKISKADIGAPSGFKHVSHV
GWDPQNGFDVNNLDPDLRSLFSRAGISEAQLTDAETSKLIYDFIEDQGGL
EAVRQEMRRQEPLPPPPPS
```

The full sequence of the WASP protein is as follows (SEQ ID NO:28):

```
MSGGPMGGRP GGRGAPAVQQ NIPSTLLQDH ENQRLFEMLG
RKCLTLATAV VQLYLALPPG AEHWTKEHCG AVCFVKDNPQ
KSYFIRLYGL QAGRLLWEQE LYSQLVYSTP TPFFHTFAGD
DCQAGLNFAD EDEAQAFRAL VQEKIQKRNQ RQSGDRRQLP
PPPTPANEER RGGLPPLPLH PGGDQGGPPV GPLSLGLATV
DIQNPDITSS RYRGLPAPGP SPADKKRSGK KKISKADIGA
PSGFKHVSHV GWDPQNGFDV NNLDPDLRSL FSRAGISEAQ
LTDAETSKLI YDFIEDQGGL EAVRQEMRRQ EPLPPPPPS
RGGNQLPRPP IVGGNKGRSG PLPPVPLGIA PPPPTPRGPP
PPGRGGPPPP PPPATGRSGP LPPPPGAGG PPMPPPPPP
PPPPSSGNGP APPPLPPALV PAGGLAPGGG RGALLDQIRQ
GIQLNKTPGA PESSALQPPP QSSEGLVGAL MHVMQKRSRA
IHSSDEGEDQ AGDEDEDDEW DD
```

The DNA fragment encoding SEQ ID NO:27 was subcloned into pET23a (Novagen) as a C-terminal 6His fusion. Site-specific cysteine mutants were constructed by QuikChange (*Stratagene*) mutagenesis using synthetic oligos and the presence of mutations was confirmed by DNA sequencing. Resultant constructs were transformed into BL21DE3 strain of *E. coli* (Novagen), and the proteins were produced by expression at 30° C. for 5 hours in 1 L Leuria-Bertani media (Sigma) in the presence of 100 µg/ml of carbenicilin. Expression was induced with 0.5 mM IPTG at $OD_{600}=0.8$-1. Cells were collected by centrifugation and stored at −20° C. until use.

Cell pellet was resuspended in cold lysis buffer (25 mM Tris-HCl, pH 7.9, 150 mM NaCl, 5 mM $MgCl_2$, 5% glycerol, 1 mM PMSF, 2 mM β-mercaptoethanol), and briefly sonicated on ice. Lysozyme and DNase were added to the suspension to a final concentration of 0.1 mg/ml and 100 U/ml, respectively, and solution was incubated with occasional stirring at 4° C. for 30 min. Lysate was centrifuged (12,000 g, 30 min), and the clarified supernatant was incubated with 1 ml of Talon resin (Clontech) at 25° C. for 30 min. The resin containing bound Cd42 binding domain (CBD) was separated from the lysate by brief low-speed centrifugation and washed twice with 15 ml of lysis buffer. Finally, the resin was washed with the lysis buffer, supplemented with 10 mM imidazole, and poured into a column. Elution was performed with 5 ml of the lysis buffer, containing 60 mM imidazole. Fractions containing bulk of CBD (as evidenced by SDS gel) were combined and dialyzed against 1 L of dialysis buffer (25 mM $Na_2HPO_4$ (pH 7.5), 10 mM NaCl) for 5 hours at 4 C. Solution was then concentrated using Aquacide powder to a final protein concentration of 2 to 10 mg/ml, and dialyzed once again against dialysis buffer. Final preparation was flash-frozen in 100 µL aliquots and stored at −80° C. Generally, 1 to 3 mg of CBD was obtained from 1 L of cell culture. Recombinant 6His-tagged cdc42, RhoA, Rac1, ERK2 and MEK were produced by analogous procedures. The enzymes were determined to be >90% active by the GTP binding assay (Knaus, U. G., Heyworth, P. G., Kinsella, B. T., Cumutte, J. T., and Bokoch, G. M. (1992) *J. Biol. Chem.* 267, 23575-23582).

Conjugation of CBD with fluorescent dyes. Dialyzed CBD samples (100-150 μM) were gently inverted with 6 to 7-fold molar excess of the reactive dye at 25° C. for 3 to 4 hours. The reaction was stopped by addition of 10 mM dithiothreitol (DTT), and the mixture was incubated for 15 min. Unreacted dye was separated from the labeled protein using G25-Sepharose (Pharmacia) gel filtration column equilibrated and developed with 25 mM $Na_2HPO_4$ (pH 7.5). Purity of the eluting fractions was analyzed by running an aliquot on an SDS gel and visualizing the fluorescence. Only the fractions containing minimal amounts of free dye were used in the subsequent experiments. Dye-to-protein ratio was determined by measuring CBD concentration ($\epsilon^{280}$=8,250 $M^{-1}$), and A4C concentration at 617 nm ($\epsilon$=70,000 $M^{-1}$ in dimethylsulfoxide) or Alexa546 at 554 nm ($\epsilon$=104,000 $M^{-1}$ in 50 mM potassium phosphate, pH 7.0). Concentrations of CBD were independently confirmed by Coomassie Plus assay (Pierce) calibrated with bovine serum albumin as a standard. Dye-to-protein ratios thus obtained varied between 0.8 and 1.2, 1.7 and 2.1 for the single-dye and dual-dye conjugates, respectively. Aliquots of the labeled CBD (15 to 50 μM) were stored at −80° C. No significant loss of binding ability was observed after 6 months of storage. In this example, CBD-conjugates were made with the dyes of the invention are referred to as mero-CBD (for merocyanines dye conjugated to CBD).

In vitro Fluorescence Assays

Fluorescence was measured at 25° C. with a Fluorolog 2 Spex 1681 Spectrometer (Jobin Yvon, Horiba), using Rhodamine B as an internal reference. The excitation and emission slit widths were 2 mm. Excitation at 600 mn and emission at 625 nm (S—SO) or 630 nm (I—SO) were used to acquire excitation and emission spectra, respectively. The fluorescence of the scFv X5 conjugates was titrated with increasing concentrations of Fc-gp120/sCD4 (incubation in PBS at 30° C., 5 min).

ELISA Binding Assays

Ninety-six-well plates were coated directly with $gp120_{BaL}$ by incubation of 0.05 ml solution containing 50 ng of the protein at 4° C. overnight. Plates were treated with 3% BSA to prevent nonspecific binding then washed with PBS containing 0.05 % Tween-20. ScFv X5 was added together with 100 ng sCD4 (in 1% BSA containing 0.02 % Tween-20) and incubated for 1.5 h at 37° C. Bound scFv X5 was detected by INDIA HisProbe-HRP (Pierce) and quantified by a colorimetric assay [Immunopure TMB Substrate (Pierce) stopped with sulfuric acid] based on measurement of optical density at 450 nm.

Titration of scFv X5 wildtype, mutants and dye-conjugates was performed using 5-fold dilution series. The data were fitted to the Langmuir adsorption isotherm using Sigma Plot 8.0 [B=($B_{max}$*XS )/($K_D$+X5), where B is the amount of bound X5, $B_{max}$ is the maximal amount of bound X5, X5 is the scFv X5 bulk concentration, and $K_D$ is the equilibrium dissociation constant].

Model of scFv X5:

The homologous model of scFv X5 provided in FIG. 12 was generated directly from the crystal structure of Fab X5. Point mutations were made according to the sequence of scFv using the graphics program O (Jones, T. A., Kjeldgaard, M. Electron-density map interpretation. *Methods in Enzymology* 277, 173-208 (1997)) followed by a geometry optimization. The 18 amino acid linker was not included in the model because the linker is highly flexible with multiple conformations and was not involved in binding.

Cell Culture and Transfection

HEK293T cells were grown in DMEM containing 10% (v/v) fetal bovine serum (Gibco). Cells (1×10⁵ cells) were plated overnight on poly-L-Lysine (10 μg/ml) and transiently transfected using FuGENE 6 (Roche) according to the manufacturer's guidelines.

In vivo Cell Fluorescence Assay

HEK293T cells were transiently cotransfected either with pCAGGS-JRFLgp160wt (Binley, J. M. et al., Redox-triggered Infection by Disulfide-shackled Human Immunodeficiency Virus Type 1 Pseudovirions. *J. Virol* 77, 5678-5684 (2003)) and pCDNA3-EGFP or with pCDNA3-EGFP alone. Thirty-six hours post-transfection cells were lifted with EDTA (5 mM in PBS), washed and resuspended in PBS. The cell suspension was incubated with H96-scFv X5-S—SO (65 and 100 nM) together with sCD4 (50 nM) for 30 min at room temperature. S—SO and EGFP fluorescence was measured using the Fluorolog 2 Spex 1681 Spectrometer. The samples were excited at 600 nm (S—SO) or 488 nm (EGFP), respectively. The emission spectra were taken from 612 to 730 nm (S—SO) and 503 to 700 nm (EGFP).

Immunofluorescence:

HEK293T cells on glass coverslips over-expressing gp120 were fixed 36 hours post transfection in 3.7% formaldehyde-PBS for 10 min and blocked in 2% BSA-PBS for 45 min at room temperature. The cells were incubated first with the primary antibody IgG1 2G12 (50 ug/ml) for 1.5 hours, washed and then incubated with the secondary antibody (20 μg/ml of R-Phycoerythrin-conjugated goat anti-human IgG, F(ab')₂ fragment specific, Jackson InmmunoResearch) for 1 h at 37° C. Coverslips were mounted with Vectashield (Vector Laboratories). Images were taken using a Zeiss Axiovert 100TV microscope, a Quantix-cooled CCD camera (Roper Scientific) and a 40×1.3 NA oil-immersion objective (exposure time: 100 ms, binning 1×1). Fluorescence filters (Chroma) for the R-Phycoerythrin fluorescence were HQ470/40 (excitation) and HQ630/40 (emission).

Results

Design of the scFv Library

Figure 9A:
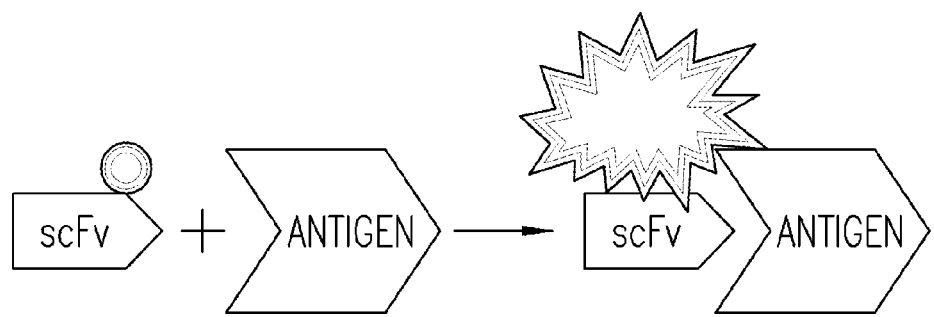
FIGS. 9A and B schematically illustrate the design of the antibody-based biosensor.
Figure 9B:
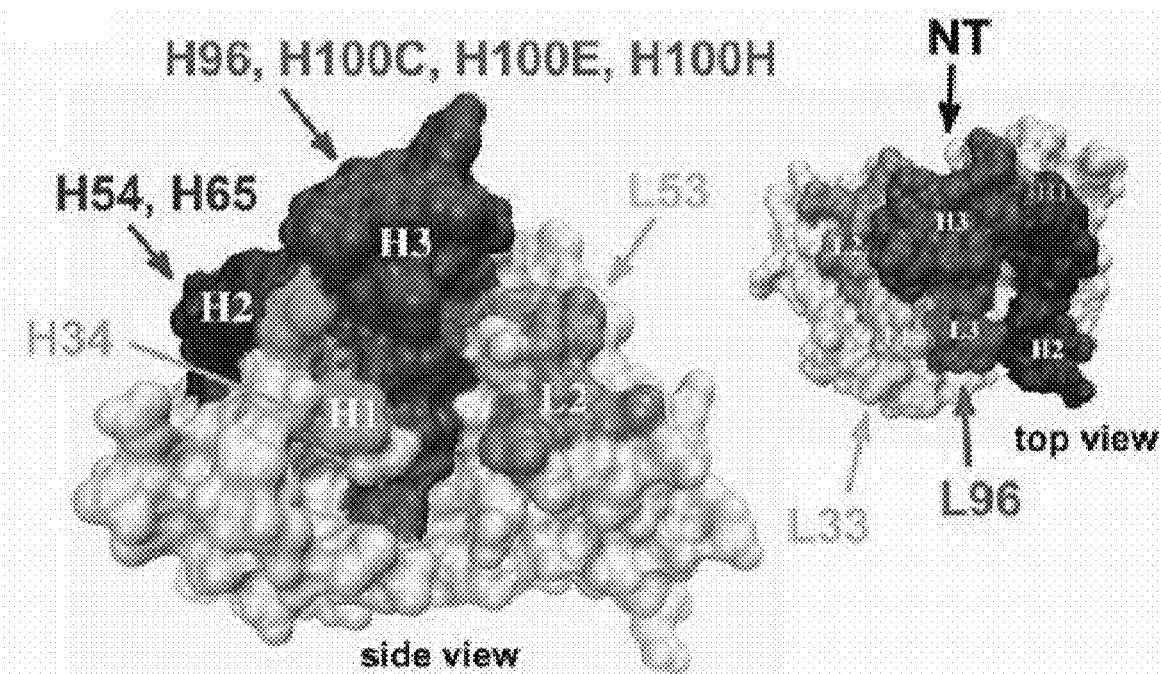
FIG. 9B illustrates the molecular surface of the single chain Fv fragment, showing the six complementary determining regions (CDR) of variable heavy and light chains (H1-3, L1-3). The eleven positions where environmentally-sensitive merocyanine dyes were attached are shown. Amino acid residues are numbered according to the Kabat scheme. Johnson, G. & Wu, T. T. Kabat database and its applications: 30 years after the first variability plot. *Nucleic Acids Res* 28, 214-218 (2000)

Optimal sites of coupling for the solvent-sensitive fluorophore within the single chain X5 fragment were identified. In order to achieve a high fluorescence response upon target binding the attachment site for the fluorescent dye would ideally be as near the binding site as possible while minimally interfering with binding. The antigen binding site of an antibody is formed from six complementary-determining regions (CDR) of the variable heavy and light chain, assembled in the scFv fragment. Crystallographic data for the free Fab X5 fragment were available to the inventors, but the structure of X5 complexed with gp120 or gp120/CD4 has not been determined. Therefore, the residues involved in binding were unknown. Hence, the CDR sequences of several scFv and Fab derived from the same phage library as X5 were compared. Ten relatively non-conserved residues were selected for substitution with cysteines, for site-selective dye attachment using cysteine-reactive dye derivatives. (Non-conserved residues were less likely to be critical to antibody binding.) One dye coupling site was introduced into each CDR of the $V_L$ chain, one into CDR1 of the heavy chain (CDR H1), and two into CDR H2 (FIG. 9B).

X5 has an extended CDR H3 loop (22 residues). Other HIV-1 neutralizing antibodies, for example, IgG1 b12 and IgG 17b, also contain extended H3 loops. Saphire, E. O. et al., Crystal Structure of a Neutralizing Human IGG against HIV-1: a Template for Vaccine Design. *Science* 293, 1155-1159 (2001); Kwong, P. D. et al., Structure of an HIV gp120 Envelope Glycoprotein in Complex with the CD4 Receptor and a Neutralizing Human Antibody. *Nature* 393, 648-659 (1998). In these HIV-1 neutralizing antibodies (IgG1 b12 and IgG 17b), CDR H3 is known to play a major role in antigen binding. Therefore, four dye coupling sites were incorporated in this loop. A cysteine was also introduced at the N-terminus of the H-chain to test whether dye could be placed at this more generally applicable position.

Each of the eleven mutants was expressed in the periplasm of *E. coli* to allow proper folding and disulfide bond formation, and purified using a hexahistidine affinity tag. Wild type and heavy chain mutants were produced in good yields (0.7 to 1.2 mg/L culture medium). Mutants with cysteines incorporated into the light chain showed significantly lower expression level (0.2-0.4 mg/L culture medium).

Each of the eleven mutants was also reacted with the cysteine-specific, iodoacetamide derivative of the solvatochromic fluorophore S—SO. Two of the CDR H3 mutants were derivatized with another dye, I—SO. Id. The fluorophores could be covalently attached to all but one scFv X5 mutant (L-S33C), which proved unreactive. Absorption spectra of the labeled mutants showed a peak at 620 nm corresponding to the dye absorption maximum in aqueous buffer. A colored, fluorescent band corresponding to the molecular weight of scFv X5 was observed on SDS-PAGE gels. Control samples of dye run on the same gel showed that no free dye species were present. From the spectra we could calculate the yield of dye coupling (moles dye per mole scFv molecule). Reaction conditions were adjusted so that labeled scFv had dye/protein values below 1. The characterization of the scFv-dye conjugates was therefore performed on molecular species that did not contain more then one dye molecule per scFv X5 and, importantly, no noncovalently attached dye.

Binding Affinities of Cysteine Mutants and Labeled scFv

Figure 10:
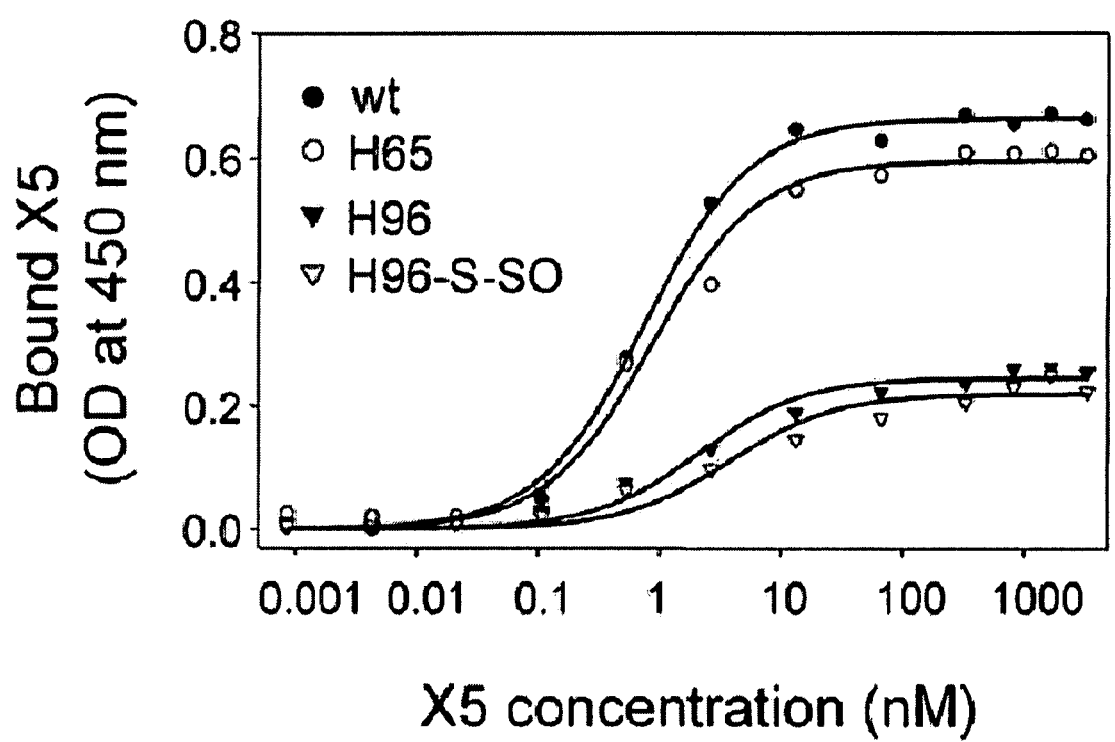
FIG. 10 graphically illustrates binding between gp120 and sCD4, from which the $K_D$ for such binding can be derived. Gp120was coated directly on 96-well plates and washed. The sCD4 was added, followed by 6xHis-scFv X5 at the indicated concentrations. Bound scFv X5 was detected using anti-6xHis-horseradish peroxidase (HRP), and by monitoring the optical density at 450 nm. In this figure, the mean absorption at 450 nm is plotted against varying concentrations of scFv X5, and fit to a monovalent binding isotherm. The graph shows binding of scFv X5 wild type, cysteine mutants (H65 and H96) and dye-conjugate (H96-S—SO).

The effects of cysteine mutation and of coupling with dye on the parameters of interaction between scFv X5 and gp120/CD4 were determined. Equilibrium dissociation constants ($K_D$) were obtained by performing ELISA assays with gp120 and soluble CD4 (sCD4) (FIG. 10).

As shown in Table 5, wild type scFv X5 binds gp120/sCD4 with a high affinity ($K_D$=1.05 nM).

TABLE 5

Binding affinities of scFv X5 mutants and fluorescent conjugates

| Mutation | $K_D$ unconjugated (nM) | $K_D$ S-SO conjugate (nM) | $K_D$ I-SO conjugate (nM) |
|---|---|---|---|
| wt | 1.05 ± 0.045 | 1.09 ± 0.02¶ | 1.06 ± 0.10¶ |
| NT | 0.52 ± 0.04 | 0.78 ± 0.09 | 0.88 ± 0.02 |
| L-Ser33 | 0.43 ± 0.05 | N.A. | * |
| L-Thr53 | 0.96 ± 0.10 | 0.35 ± 0.04 | * |
| L-Tyr96 | 1.34 ± 0.06 | 0.86 ± 0.09 | 2.43 ± 0.25 |
| H-Phe34 | 2.78 ± 0.07 | 0.41 ± 0.05 | * |
| H-Ile54 | 0.70 ± 0.07 | 0.88 ± 0.10 | 0.75 ± 0.10 |
| H-Arg65 | 1.57 ± 0.06 | 3.48 ± 0.12 | * |
| H-Phe96 | 7.22 ± 0.04 | 7.98 ± 1.20 | 8.46 ± 0.14 |

TABLE 5-continued

Binding affinities of scFv X5 mutants and fluorescent conjugates

| Mutation | $K_D$ unconjugated (nM) | $K_D$ S-SO conjugate (nM) | $K_D$ I-SO conjugate (nM) |
|---|---|---|---|
| H-Gly100C | 3.40 ± 0.50 | 1.82 ± 0.01 | * |
| H-Ser100E | 1.98 ± 0.10 | 1.73 ± 0.40 | 1.41 ± 0.28 |
| H-Gly100H | 1.39 ± 0.06 | 1.50 ± 0.14 | * |

N.A. could not be labeled with S-SO
¶treated with dye, but not covalently attached
*conjugate not prepared The effects of the mutations to Cys on binding affinity were minimal, except for one of the CDR H3 mutants (Table 5). H-F96C bound gpI20/sCD4 with somewhat lower affinity, but even this somewhat lower affinity was still quite high ($K_D$=7.22 nM). H-G100cS and H-F34C show slightly lower affinity ($K_D$=3.4 and 2.78 nM, respectively). A comparison of the KD'S for the mutant scFv X5 fragments and their fluorescent derivatives (Table 5) showed that the presence of the fluorophore had very little effect on the interaction with gp120/sCD4. In control experiments, treatment of wild type scFv X5 with fluorophore in the same way as the mutants did not lead to covalent labeling and did not result in a decrease in binding activity. The use of S—SO versus I—SO dye did not appear to be important to effects on binding affinity. This is reasonable given the small differences in their structure. See Toutchkine et al., Solvent-sensitive Dyes to Report Protein Conformational Changes in Living Cells. *J Am Chem Soc* 125, 4132-4145 (2003). These results showed that cysteine could be inserted at a range of positions on the scFv fragment without perturbing affinity to levels that would interfere with biosensor applications. Dye coupling also did not greatly perturb binding affinity, despite the fact that dyes were positioned to show good fluorescence responses (see below).

Fluorescence Responses of the Labeled scFv X5 Fragments in vitro

The fluorescence properties of the scFv S—SO conjugates were characterized as illustrated in FIG. 11. As illustrated in FIG. 11, the fluorescence response of the dye is influenced by its position on the scFv binding domain.

Figure 11A:
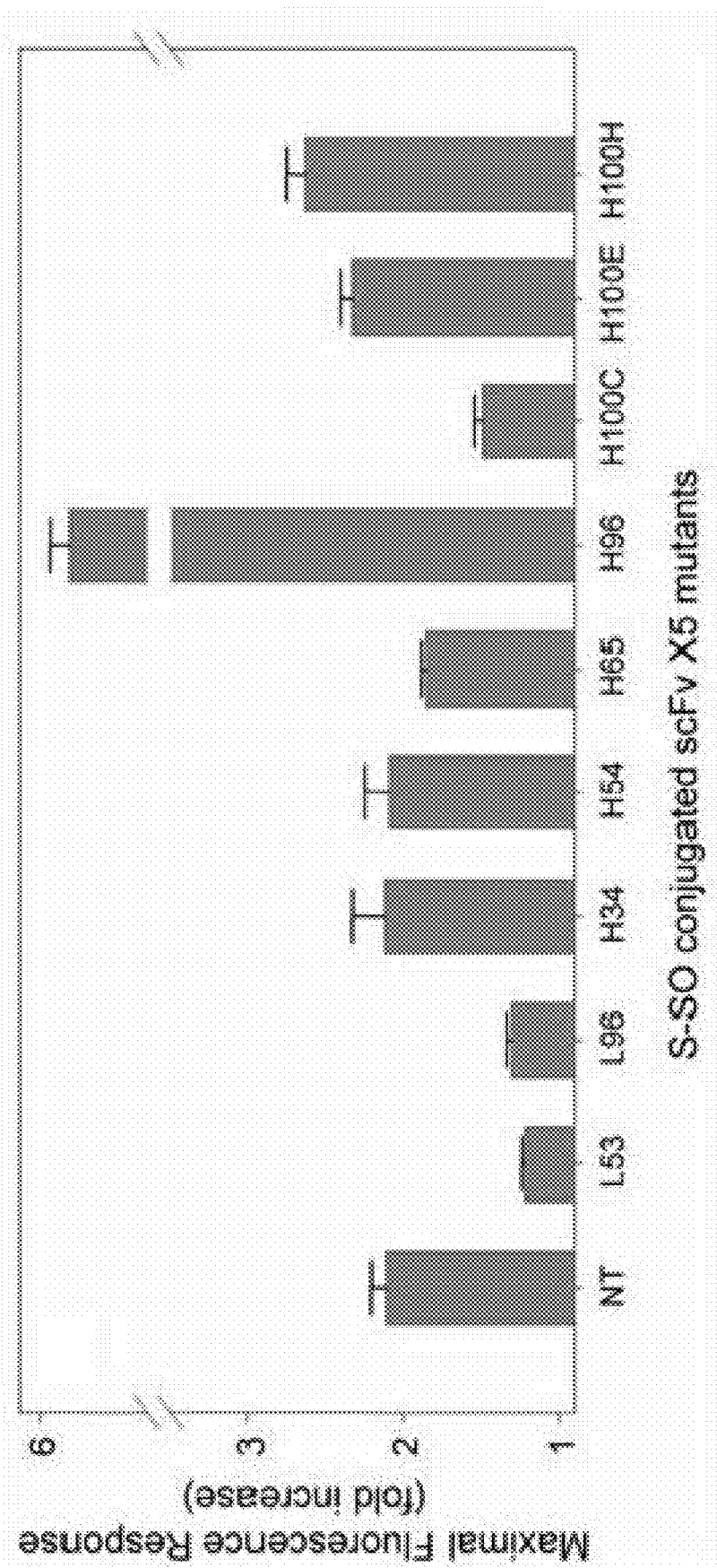
FIGS. 11A-D illustrate the in vitro properties of scFv mutants obtained from a labeled scFv X5 library providing scFv polypeptides with dyes attached at different amino acid residue positions.
Figure 11B:
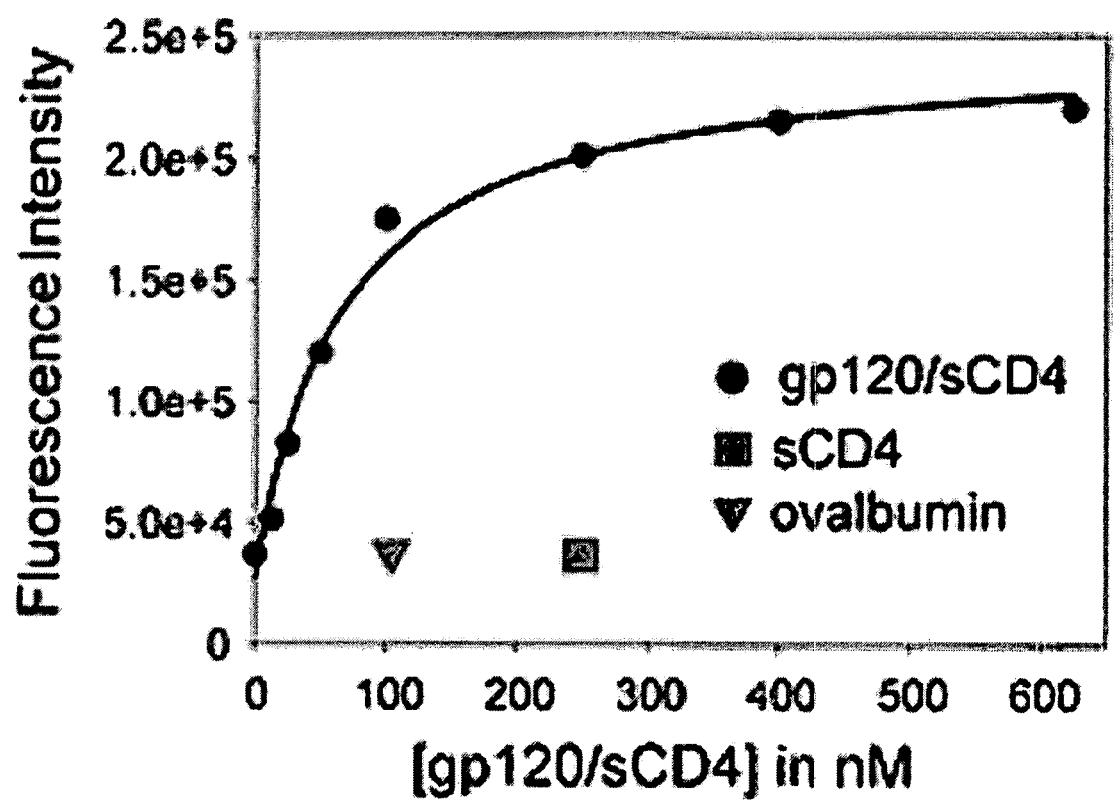
Figure 11C:
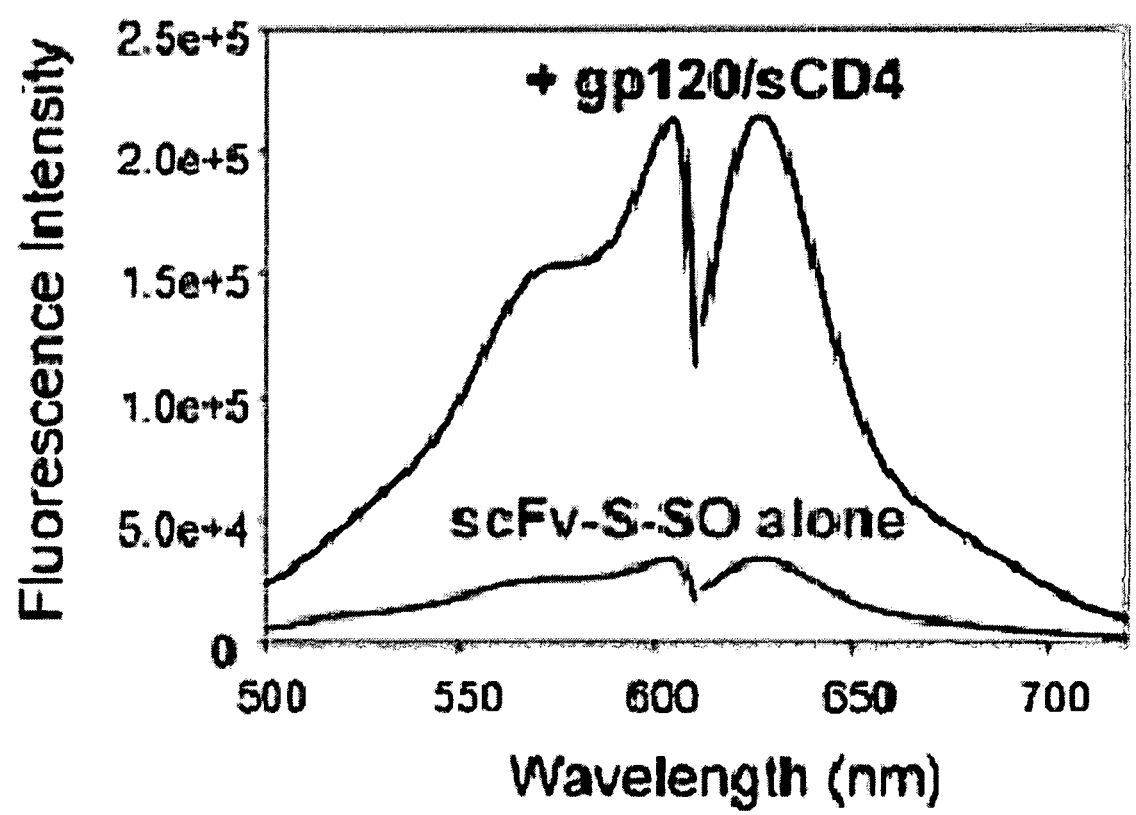

The fluorescence intensities of the dye conjugates were measured in the presence of increasing concentrations of an equimolar ratio of gp120 and sCD4. The maximal value of the fluorescence intensity was attained for an emission wavelength of 625 nm. The fluorescence response was titrated to determine the maximum response and was specific for interactions with gp120/sCD4 (FIG. 11B). Saturation was reached and measured at gp120/sCD4 concentrations five times higher than the scFv X5 conjugate concentration of 130 nM. The maximal fluorescence response varied from a 20% increase to a nearly 6-fold increase (FIG. 11A). The highest fluorescence responses were obtained from three positions in the CDR3 loop of the heavy chain (H96, H100H, H100E), with conjugation at position H96 giving an almost 6-fold increase (FIG. 11C).

Interestingly, the mutant with the highest fluorescence response was also that whose binding affinity was most affected by cysteine mutation and dye attachment. Several of the S—SO labeled positions in different loops led to a fluorescence intensity increase of 2- to 3-fold. The introduction of S—SO near the N-terminus led to a 2.1-fold response. There was a weak response in four positions (1.2- to 1.8-fold). Position CDR L1 could not be tested, because S—SO could not be covalently attached at this site. In control experiments, the labeled scFv were incubated with ovalbumin and with sCD4 alone, in each case producing no response (FIG. 11B).

Figure 11D:
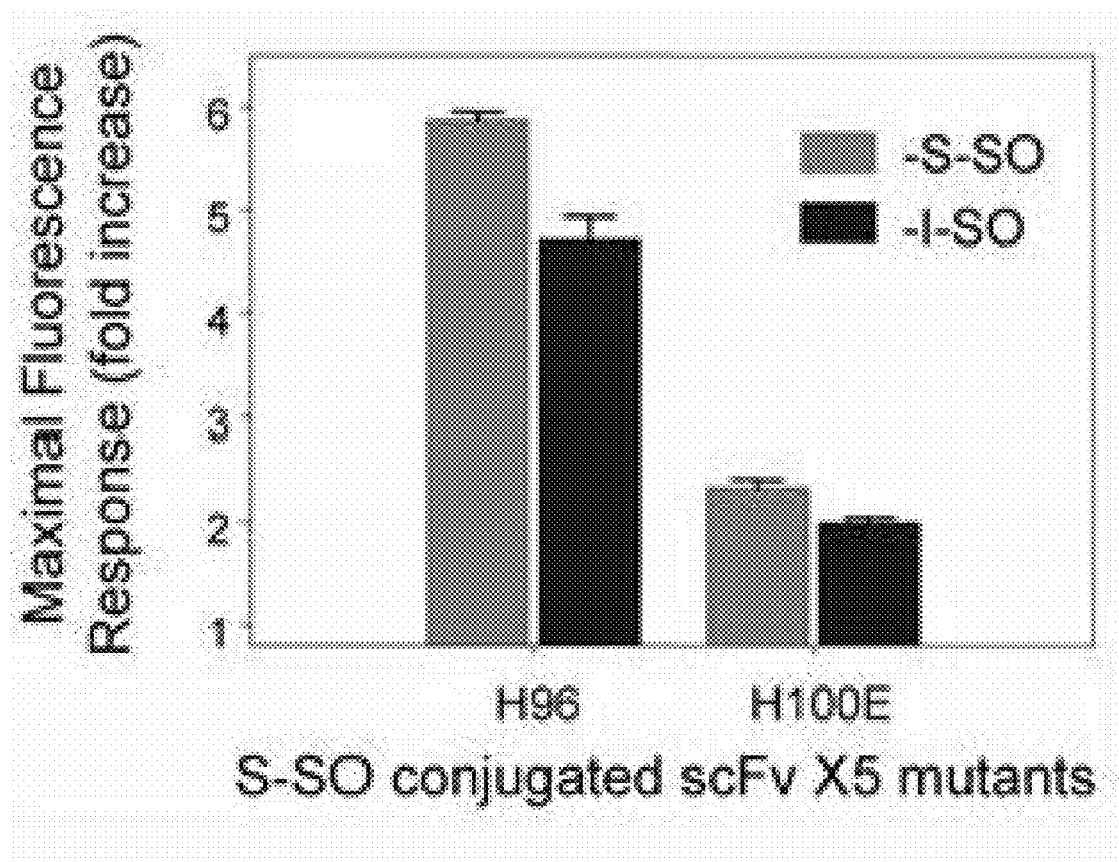

The fluorescence response of two different dyes, S—SO and I—SO, was compared at positions H96 and H100E (FIG. 11D). The two dyes produced similar fluorescence changes. Of eleven labeling positions, six led to scFv-dye conjugates with an excellent response (more than 2-fold), and four to biosensors that respond with 20 to 80% intensity increase.

Model of scFv X5 Structure and Positions of Dye Attachment

A model of the Fv fragment was derived from the Fab X5 crystal structure (unpublished data) to understand how the observed fluorescence responses of the S—SO-conjugates were governed by their position on the binding surface. The N-terminal region of the Fab X5 consisting of the light chain and heavy chain N-terminal domains was used to generate the scFv model. It was assumed that the structural features of the N-terininal region of the Fab remain the same in the scFv. The hydrophobic environment and the solvent accessibility around the eleven residues chosen for Cys point mutations were examined.

Figures 12A, 12B:
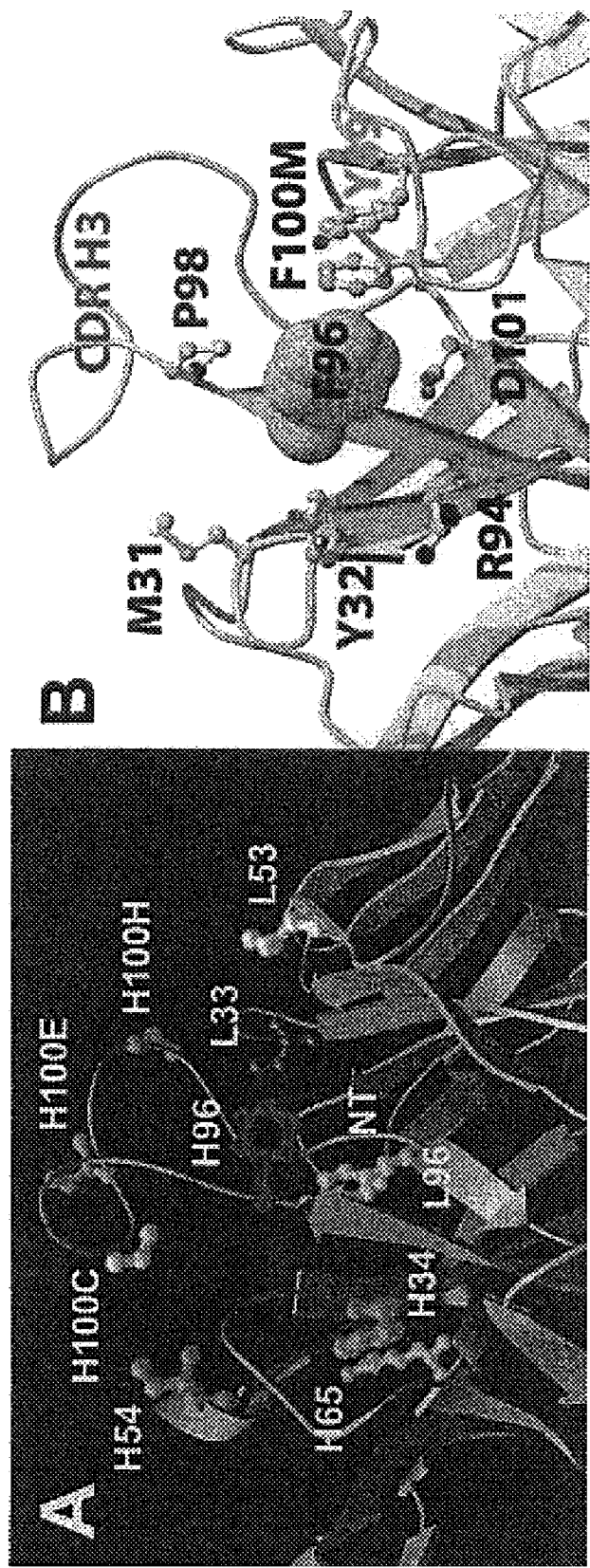
FIGS. 12A and B provide a model of labeled scFv X5.
FIG. 12B provides a schematic representation of the scFv model showing the hydrophobic environment of residue Phe-H96. β-strands are illustrated as gold arrows and loops as gray tubes in the original. Heavy chain residues are labeled in blue and the light chain residue in cyan in the original.

FIG. 12A illustrates the backbone of the scFv fragment as a ribbon diagram, with attachment sites for the solvent-sensitive dye mapped with a color code to show fluorescence response at each position. Out of the eleven residues, H96 has a highly hydrophobic environment along with a significant solvent accessible surface (FIG. 12B), resulting in the highest fluorescence response, with an almost 6-fold increase.

Detection of gp120 Expression on Living Cells

Figure 13A:
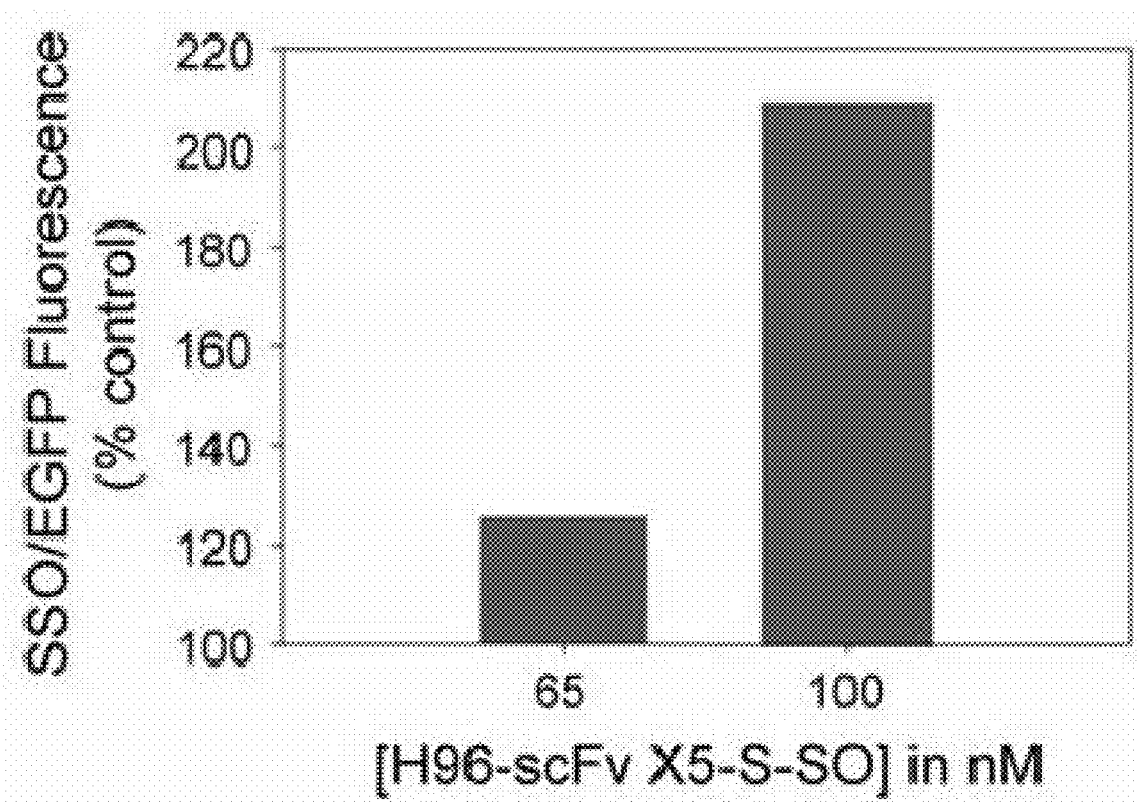
FIGS. 13A-C illustrate detection of gp120 on the surface of living cells.
Figures 13B, 13C:
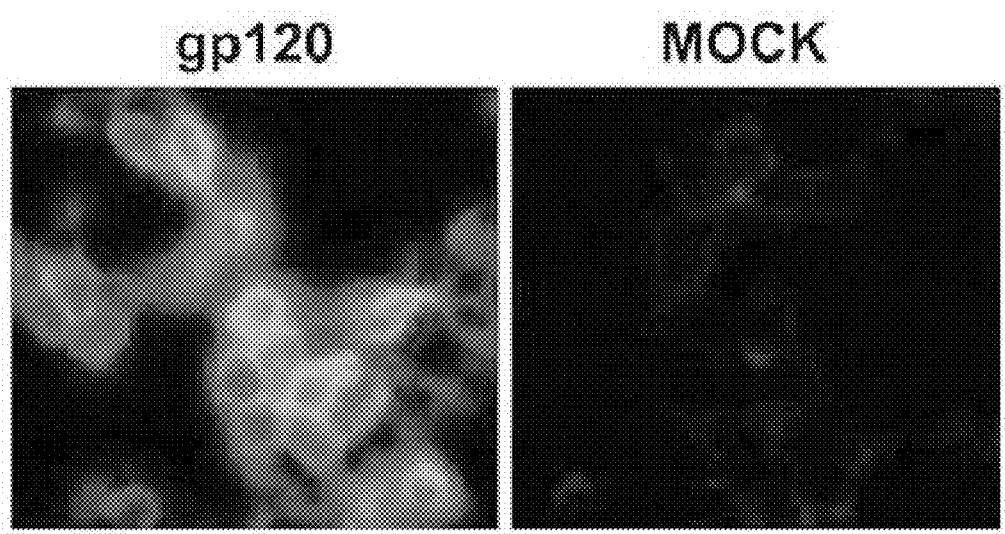

The biosensor was used for rapid and facile quantification of gp120 expression on the surface of living cells. Human embryonic kidney 293T (HEK 293T) cells transiently expressing both EGFP and surface gp120 were incubated with excess sCD4 (50 nM) and two different concentrations of H96-scFv X5-S—SO (65 and 100 nM). Control cells expressing only EGFP were treated identically. The SSO and EGFP fluorescence of cell suspensions was measured in a fluorimeter without washing away unbound biosensor. The ratio of the S—SO to EGFP fluorescence was compared for gp120-expressing versus control cells (FIG. 13A). Depending on the concentration of the scFv X5 S—SO-conjugate, the S—SO/EGFP ratio was 200% that of the control cells, consistent with the biosensor responding to gp120. Surface expression of gp120 was verified by Irmnunofluorescence (FIG. 13B).

EXAMPLE 3

Detecting Phosphorylation Induced Changes in Erk

This Example illustrates that the dyes of the invention can be attached directly to a protein of interest (e.g. Erk), where the dyes respond to conformational changes and phosphorylation. In particular, the I-TBA-3CNPh dye was attached to cysteine 214 of the MAP kinase Erk2, where it responded to Erk phosphorylation. A structure for the I-TBA-3CNPh dye is provided below.

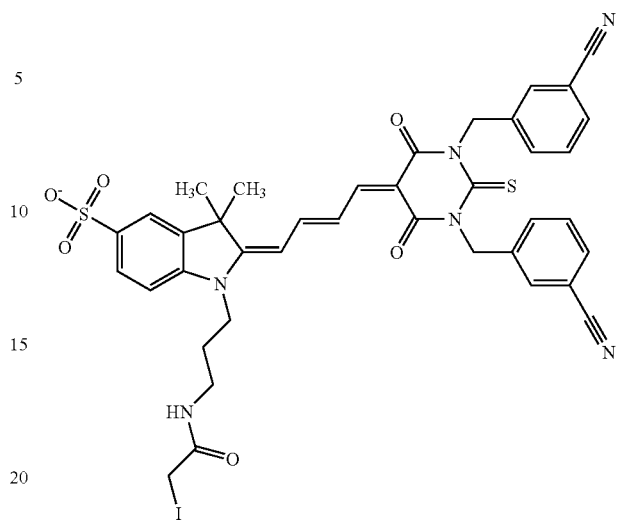

Figure 15A:
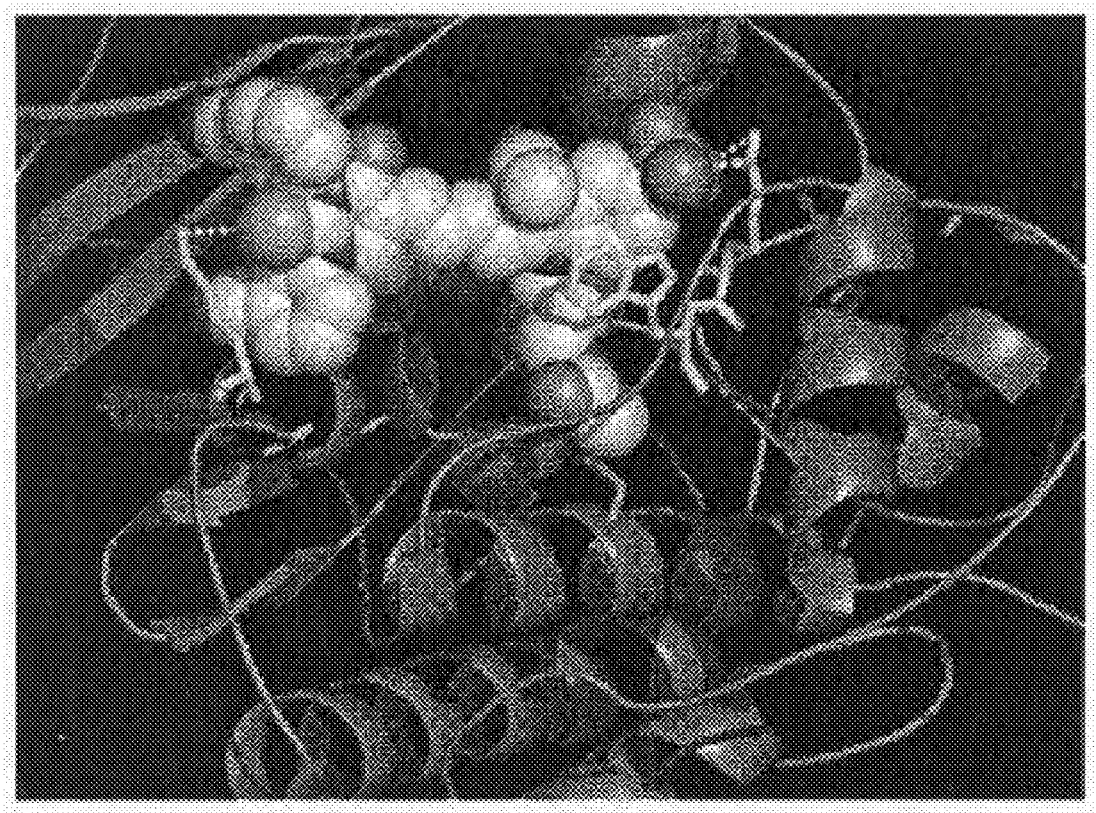
FIG. 15A illustrates that the merocyanine dye fluorescence is affected by hydrogen bonding and π-π stacking interactions with specific residues of MAP kinases Erk2 and Elk1.

FIG. 15A shows the I-TBA-3CNPh dye in a space filling model as it is thought to fit into the Erk2 structure. This model was based on tryptic digestion combined with mass spectroscopic sequencing of the labeled protein, and on docking studies. The lighter (yellow) residues represent two lysines undergoing hydrogen bonding with the dye, and a tryptophan interacting through π-π stacking. Phosphorylation of the purple residues altered the conformation of the protein, affecting the tryptophan interaction and perturbing some of the hydrogen bonds. Such phosphorylation and conformational changes were enough to cause a phosphorylation-induced increase in fluorescence of the I-TBA-3CNPh dye (FIG. 15B) in wild type Erk2 protein upon incubation with MEK kinase (which phosphorylates Erk2) and ATP.

Use of an Erk2 mutant that could not be phosphorylated resulted in no fluorescence change, even with saturating excess MEK. These results indicate that the fluorescence change was due to phosphorylation, not to binding of MEK. The Western blots show normal phosphorylation of the labeled Erk2 protein, and normal phosphorylation of an Erk2 substrate, Elk. Hence, the labeled Erk2 protein retains phosphorylation activity.

Figure 15C:
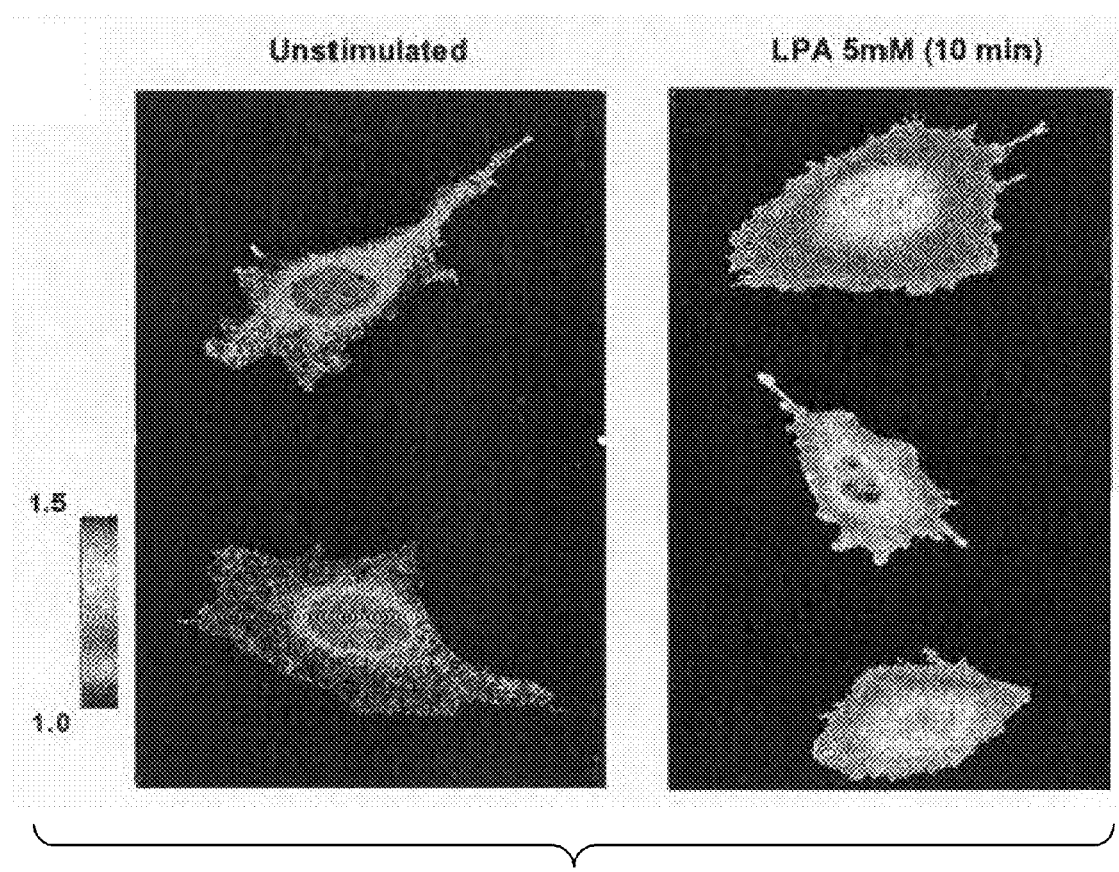
FIG. 15C shows that the dye responded to Erk2 phosphorylation, not MEK binding. Addition of saturating MEK to a phosphorylation-incompetent Erk2 mutant did not produce a fluorescence change.

FIG. 15C shows results of incubating the labeled Erk2 in living cells. Erk2 fluorescence in serum-starved fibroblasts (left) was compared with LPA-stimulated fibroblasts (right). The expected nuclear activation was observed, together with localized activation near what appeared to be adhesion complexes.

These results indicate that the dyes of the invention can be successfully attached to proteins without adversely affecting the normal function of those proteins, and the conformational and functional changes of those dye-labeled proteins can be observed not only in vitro but also in vivo.

REFERENCES

1. Zhang, J., Campbell, R. E., Ting, A. Y. & Tsien, R. Y. Creating new fluorescent probes for cell biology. *Nat Rev Mol Cell Biol* 3, 906-918 (2002).
2. Lippincott-Schwartz, J., Snapp, E. & Kenworthy, A. Studying protein dynamics in living cells. *Nat Rev Mol Cell Biol* 2, 444-456 (2001).

3. Lippincott-Schwartz, J. & Patterson, G. H. Development and use of fluorescent protein markers in living cells. *Science* 300, 87-91 (2003).
4. Wouters, F. S., Verveer, P. J. & Bastiaens, P. I. Imaging biochemistry inside cells. *Trends Cell Biol* 11, 203-211 (2001).
5. Kraynov, V. S. et al. Localized Rac activation dynamics visualized in living cells. *Science* 290, 333-337 (2000).
6. Gardiner, E. M. et al. Spatial and temporal analysis of Rac activation during live neutrophil chemotaxis. *Curr Biol* 12, 2029-2034 (2002).
7. Del Pozo, M. A. et al. Integrins regulate GTP-Rac localized effector interactions through dissociation of Rho-GDI. *Nat Cell Biol* 4, 232-239 (2002).
8. Ting, A. Y., Kain, K. H., Klemke, R. L. & Tsien, R. Y. Genetically encoded fluorescent reporters of protein tyrosine kinase activities in living cells. *Proc Natl Acad Sci USA* 98, 15003-15008 (2001).
9. Zhang, J., Ma, Y., Taylor, S. S. & Tsien, R. Y. Genetically encoded reporters of protein kinase A activity reveal impact of substrate tethering. *Proc Natl Acad Sci USA* 98, 14997-15002 (2001).
10. Mochizuki, N. et al. Spatio-temporal images of growth-factor-induced activation of Ras and Rap1. *Nature* 411, 1065-1068 (2001).
11. Toutchkine, A., Kraynov, V. & Hahn, K. Solvent-sensitive dyes to report protein conformational changes in living cells. *J Am Chem Soc* 125, 4132-4145 (2003).
12. Burton, D. R. & Barbas, C. F., 3rd Human antibodies from combinatorial libraries. *Adv Immunol* 57, 191-280 (1994).
13. Winter, G., Griffiths, A. D., Hawkins, R. E. & Hoogenboom, H. R. Making antibodies by phage display technology. *Annu Rev Immunol* 12, 433-455 (1994).
14. Rader, C. & Barbas, C. F., 3rd Phage display of combinatorial antibody libraries. *Curr Opin Biotechnol* 8, 503-508 (1997).
15. Knappik, A. et al. Fully synthetic human combinatorial antibody libraries (HuCAL) based on modular consensus frameworks and CDRs randomized with trinucleotides. *J Mol Biol* 296, 57-86 (2000).
16. Feldhaus, M. J. et al. Flow-cytometric isolation of human antibodies from a nonimmune *Saccharomyces cerevisiae* surface display library. *Nat Biotechnol* 21, 163-170 (2003).
17. Boder, E. T., Midelfort, K. S. & Wittrup, K. D. Directed evolution of antibody fragments with monovalent femtomolar antigen-binding affinity. *Proc Natl Acad Sci USA* 97, 10701-10705 (2000).
18. Hanes, J., Schaffitzel, C., Knappik, A. & Pluckthun, A. Picomolar affinity antibodies from a fully synthetic naive library selected and evolved by ribosome display. *Nat Biotechnol* 18, 1287-1292 (2000).
19. Schaffitzel, C., Hanes, J., Jermutus, L. & Pluckthun, A. Ribosome display: an in vitro method for selection and evolution of antibodies from libraries. *J Immunol Methods* 231, 119-135 (1999).
20. Moulard, M. et al. Broadly cross-reactive HIV-1-neutralizing human monoclonal Fab selected for binding to gp120-CD4-CCR5 complexes. *Proc Natl Acad Sci USA* 99, 6913-6918 (2002).
21. Saphire, E. O. et al. Crystal structure of a neutralizing human IGG against HIV-1: a template for vaccine design. *Science* 293, 1155-1159 (2001).
22. Kwong, P. D. et al. Structure of an HIV gp120 envelope glycoprotein in complex with the CD4 receptor and a neutralizing human antibody. *Nature* 393, 648-659 (1998).
23. Zaccolo, M. et al. A genetically encoded, fluorescent indicator for cyclic AMP in living cells. *Nat Cell Biol* 2, 25-29 (2000).
24. Renard, M., Belkadi, L. & Bedouelle, H. Deriving topological constraints from functional data for the design of reagentless fluorescent immunosensors. *J Mol Biol* 326, 167-175 (2003).
25. Sloan, D. J. & Hellinga, H. W. Structure-based engineering of environmentally sensitive fluorophores for monitoring protein-protein interactions. *Protein Eng* 11, 819-823 (1998).
26. Iwatani, S., Iwane, A. H., Higuchi, H., Ishii, Y. & Yanagida, T. Mechanical and chemical properties of cysteine-modified kinesin molecules. *Biochemistry* 38, 10318-10323 (1999).
27. Nizak, C. et al. Recombinant antibodies to the small GTPase Rab6 as conformation sensors. *Science* 300, 984-987 (2003).
28. Collis, A. V., Brouwer, A. P. & Martin, A. C. Analysis of the antigen combining site: correlations between length and sequence composition of the hypervariable loops and the nature of the antigen. *J Mol Biol* 325, 337-354 (2003).
29. Mandal, D., Kumar, S., Sukul, D. & Bhattacharyya, K. Photophysical Processes of Merocyanine 540 in Solutions and in Organized Media. *J Phys Chem A* 103, 8156-8159 (1999).
30. Verveer, P. J., Wouters, F. S., Reynolds, A. R. & Bastiaens, P. I. Quantitative imaging of lateral ErbB1 receptor signal propagation in the plasma membrane. *Science* 290, 1567-1570 (2000).
31. Tse, E. & Rabbitts, T. H. Intracellular antibody-caspase-mediated cell killing: an approach for application in cancer therapy. *Proc Natl Acad Sci USA* 97, 12266-12271 (2000).
32. Subauste, M. C. et al. A catalytic antibody produces fluorescent tracers of gap junction communication in living cells. *J Biol Chem* 276, 49164-49168 (2001).
33. der Maur, A. A. et al. Direct in vivo screening of intrabody libraries constructed on a highly stable single-chain framework. *J Biol Chem* 277, 45075-45085 (2002).
34. Proba, K., Worn, A., Honegger, A. & Pluckthun, A. Antibody scFv fragments without disulfide bonds made by molecular evolution. *J Mol Biol* 275, 245-253 (1998).
35. Visintin, M. et al. The intracellular antibody capture technology (IACT): towards a consensus sequence for intracellular antibodies. *J Mol Biol* 317, 73-83 (2002).
36. Tanaka, T., Chung, G. T., Forster, A., Lobato, M. N. & Rabbitts, T. H. De novo production of diverse intracellular antibody libraries. *Nucleic Acids Res* 31, e23 (2003).
37. Jobling, S. A. et al. Immunomodulation of enzyme function in plants by single-domain antibody fragments. *Nat Biotechnol* 21, 77-80 (2003).
38. Barbas, C. F. 3rd., Burton, D. R., Scott, J. K. & Silvermann, G. J. Phage Display: A Laboratory Manual. (Cold Spring Harbor Laboratory Press, Cold Spring Harbor; 2001).
39. Bebbington, C. R. et al. High-level expression of a recombinant antibody from myeloma cells using a glutamine synthetase gene as an amplifiable selectable marker. *Biotechnology (N Y)* 10, 169-175 (1992).
40. Haugland, R. P. Handbook of Fluorescent Probes and Research Products, Edn. Ninth Edition. (Molecular Probes, Inc., Eugene; 2002).
41. Jones, T. A., Kjeldgaard, M. Electron-density map interpretation. *Methods in Enzymology* 277, 173-208 (1997).
42. Binley, J. M. et al. Redox-triggered infection by disulfide-shackled human immunodeficiency virus type 1 pseudovirions. *J Virol* 77, 5678-5684 (2003).

43. Johnson, G. & Wu, T. T. Kabat database and its applications: 30 years after the first variability plot. *Nucleic Acids Res* 28,-214-218 (2000).
44. Soper, S. A.; Mattingly, Q. L. *J. Am. Chem. Soc.* 1994, 116, 3744-3752.
45. Ischenko, A. *Russ. Chem. ReV.* 1991, 60, 865-884.
46. Demas, J. N.; Crosby, G. A. *J. Phys. Chem.* 1971, 75, 991-1024.
47. Flannagan, J. H.; Khan, S. H.; Menchen, S.; Soper, S. A.; Hammer, R. P. *Bioconj. Chem.* 1997, 8, 751-756.
48. Lednev, I. K.; Fydorova, O. A.; Gromov, S. P.; Alfimov, M. V. *Spectrochim. Acta, Part A* 1993, 49A, 1055-1056.
49. Narayanan, N.; Patonay, G. *J. Org. Chem.* 1995, 60, 2391-2395.
50. Regitz, M. *Chem. Ber.* 1965, 98, 36-45.
51. Mujumdar, R. B.; Ernst, L. A.; Mujumdar, S. R.; Waggoner, A. S. *Cytometry* 1989, 10, 11-19.
52. Manning, W. B.; Horak, V. *Synthesis* 1978, 5, 363.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A biosensor comprising:
   (a) a binding domain with specific affinity for a target molecule; and,
   (b) an environmentally sensitive dye covalently linked to the binding domain;
   wherein the dye is a compound of one of the following formulae:

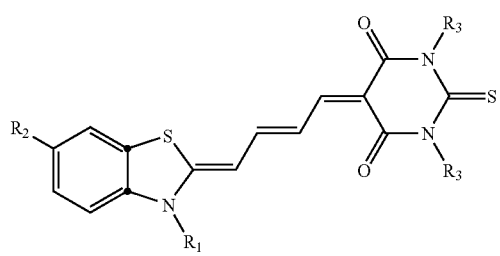

1

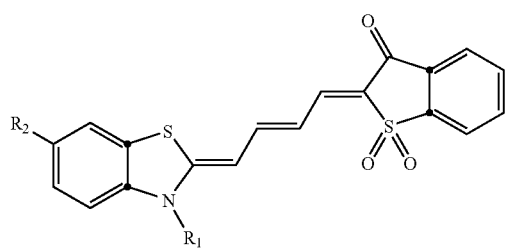

2

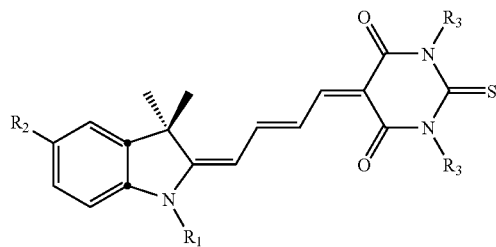

3

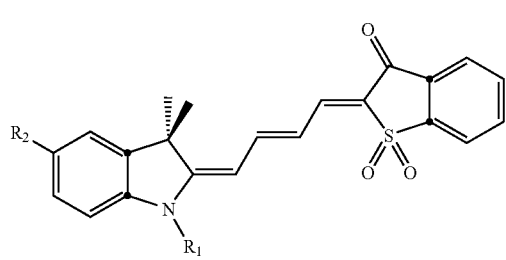

4

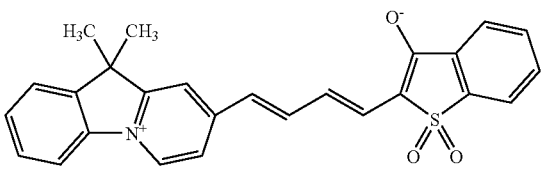

5 wherein:
  $R_1$ is lower alkyl, —$(CH_2)_3$—$SO_3^-$, —$(CH_2)_3$—NH—CO—$CH_2$—I or —$(CH_2)_3$—$N^+(CH_3)_2$—$(CH_2)_2$—NCS;
  $R_2$ is H, —$NH_2$, —$SO_3^-$, $CH_3CONH$—, $ICH_2CONH$—, $HO(CH_2)_2$—S—$CH_2CONH$—; $SuOCOCH_2OCH_2CON(CH_3)$— or a protecting group; and
  $R_3$ is lower alkyl or tolyl-acetonitrile.

2. The biosensor of claim 1, wherein the binding domain binds to the target molecule when the target molecule is in a specific conformation, or when the target molecule has bound to a specific ligand, or when the target molecule has been posttranslationally modified.

3. The biosensor of claim 2, wherein the target molecule has been phosphorylated.

4. The biosensor of claim 3, wherein binding of the binding domain to the target molecule does not block phosphorylation of the target molecule.

5. The biosensor of claim 1, wherein the target molecule comprises a nucleic acid or a protein.

6. The biosensor of claim 1, wherein the binding domain is a polypeptide.

7. The biosensor of claim 1, wherein the binding domain comprises: an aptamer, a complementary determining region (CDR), a VH region, a VL region, a Fv fragment, an F(ab) fragment, an F(ab')2 fragment, an antibody, an antibody fragment, a leucine zipper, a histone, an enhancer, a single chain variable fragment (scFv), a ligand, a receptor, one protein in a protein complex, an aptamer, or a lectin.

8. The biosensor of claim 1, wherein the binding domain comprises any one of SEQ ID NOs: 1, 2, 4, 5, 9, 10, 11, 12, 16, 17, 18, 19, 20, 21, 22 and 27.

9. The biosensor of claim 1, wherein the binding domain comprises any one of SEQ ID NOs: 23 and 24.

10. The biosensor of claim 1, wherein the binding domain comprises SEQ ID NO:5 or SEQ ID NO:12, wherein at least one underlined amino acid residue in SEQ ID NO:5 or SEQ ID NO:12 is cysteine, as indicated below:

```
                                        SEQ ID NO:5
TCT LTQSPGTLSL SAGERATLSC RASQSVSSGS LAWYQQKPGQ
    APRLLIYGAS TRATGIPDRF SGSGSGTDFT LTIGRLEPED
    LAVYYCQQYG TSPYTFGQGT KVDIKR

SEQ ID NO:12
QVQ LVQSGAEVKK PGSSVQVSCK ASGGTFSMYG FNWVRQAPGH
    GLEWMGGIIP IFGTSNYAQK FRGRVTFTAD QATSTAYMEL
    TNLRSDDTAV YYCARDFGPD WEDGDSYDGS GRGFFDFWGQ
124 GTLVTVSSPR GPAG.
```

11. The biosensor of claim 1, wherein the dye comprises an aromatic ring with one or more nonplanar alkyl or heteroatom substituents projecting out of the plane of the aromatic ring.

12. The biosensor of claim 1, wherein the fluorescent signal comprises a light wavelength of about 400 nm or more.

13. The biosensor of claim 1, wherein the fluorescent signal is not fluorescent resonance energy transfer (FRET)-dependent.

14. The biosensor of claim 1, wherein the binding domain is linked to the target molecule by a linker.

15. The biosensor of claim 14, wherein the linker is selected from the group consisting of: hydroxysuccinimides, maleimides, haloacetyls, pyridyl disulfides, hydrazines, ethyldiethylamino propylcarbodiimide and iodoacetamido groups.

16. The biosensor of claim 1, wherein two or more dye molecules are linked to the binding domain.

17. The biosensor of claim 16, wherein a signal from one of the dye molecules changes on binding of the binding domain to the target molecule, and wherein the signal is not generated by fluorescence resonance energy transfer (FRET).

18. The biosensor of claim 1, wherein the dye molecule is linked to the binding domain at a cysteine, a lysine, an arginine, a natural amino acid side chain, a derivitized amino acid side chain, or an unnatural amino acid in the binding domain.

19. The biosensor of claim 1, wherein the binding domain comprises a single chain variable fragment comprising SEQ ID NO:1, SEQ ID NO:2 or SEQ ID NO:4 and wherein:
   SEQ ID NO:1 is LTQSPGTLSLSAGERATLSC(X)nW-YQQ KPGQA PRLLIY(X)nGIPDRFSGSGSGTD-FTLTIGRLEPEDLAVYYC(X)n;
   SEQ ID NO:2 is QVQLVQSGAEVKKPGSSVQVSCK-ASGGTF(X)n WVRQAPGHGLEWMG(X)nRVT-FTADQATSTAYMELTNLRSDDT AVYYCAR(X) nWGQGTLVTVSSPRGPAGQ; and
   SEQ ID NO:4 is TQSPGTLSLSAGERATLSC(X)nW-YQQKPGQA PRLLIY(X)nGIPDRFSGSGSGTD-FTLTIGRLEPEDLAVYYC(X)nG GGGSGGGGSGGGGSRSSQVQLVQSGAE-VKKPGSSVQVSC KASGGTF(X)nWVRQAPGH-GLEWMG(X)nRVTFTADQATSTAY MELTNLRSD-DTAVYYCAR(X)nWGQGTLVTVSSPRGPAGQ; and
   wherein each X separately represents a variable amino acid, n is an integer between about 3 and about 25, and wherein one or more X amino acid can be a cysteine that provides an attachment site for the dye.

20. The biosensor of claim 1 for detecting HIV comprising a binding domain that can bind to HIV, and a dye, wherein the binding domain comprises a CDR fragment consisting essentially of a peptide having sequence RASQSVSSGCLA (SEQ ID NO:9), GASCRAT (SEQ ID NO:10), QQYGTSPCTF-GQGTKVDIKR (SEQ ID NO:11), SMYGCN (SEQ ID NO: 16), GIIPCFGTSNYAQKFRG (SEQ ID NO: 17), GIIPIF-GTSNYAQKFCG (SEQ ID NO: 18), DCGPD-WEDGDSYDGSGRGFFDF (SEQ ID NO: 19), DFGPD-WEDCDSYDG SGRGFFDF (SEQ ID NO:20), DFGPDWEDGDCYDGSGRGFFDF (SEQ ID NO:21) or DFGPDWEDGDSYDCSGRGFFDF (SEQ ID NO:22).

21. A method of detecting a selected target molecule's activity or location within a cell comprising contacting the cell with the biosensor of claim 1 and observing a change in signal produced by the biosensor or a change in location of the signal, wherein the binding domain is a single chain variable fragment (scFv) of an antibody with an attachment site for a dye within a CDR3 region of the scFv.

22. The method of claim 21, wherein the biosensor binding domain comprises SEQ ID NO:1, SEQ ID NO:2 or SEQ ID NO:4.

23. The method of claim 21, wherein the selected target molecule is a protein, receptor, ligand or enzyme.

24. The method of claim 21, wherein the selected target molecule's activity comprises the selected molecule's phosphorylation state, subcellular location, interaction with subcellular structures or interaction with cellular proteins.

25. The biosensor of claim 1, wherein the binding domain comprises SEQ ID NO:12, where Phe-97 is Cys.

26. The biosensor of claim 1, wherein the environmentally sensitive dye linked to the binding domain is a compound of the formula:

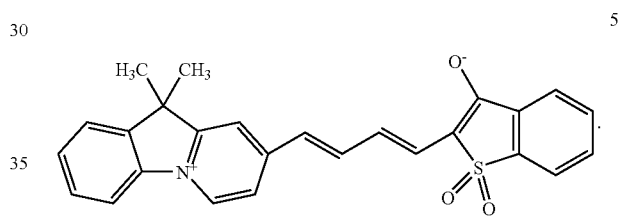

27. The biosensor of claim 1, wherein the environmentally sensitive dye has a quantum yield greater than about 0.5.

28. An environmentally sensitive fluorescent dye, wherein the dye is a compound of any one of the following formulae:

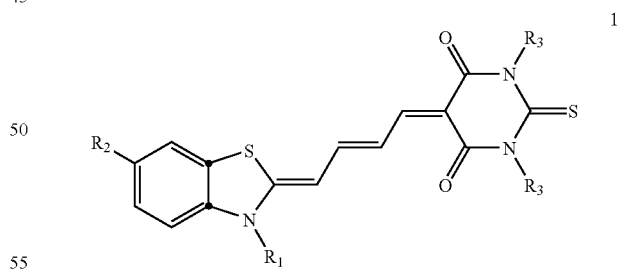

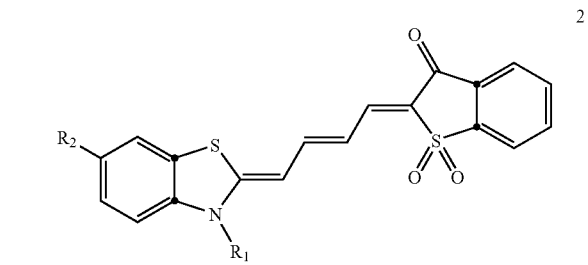

-continued

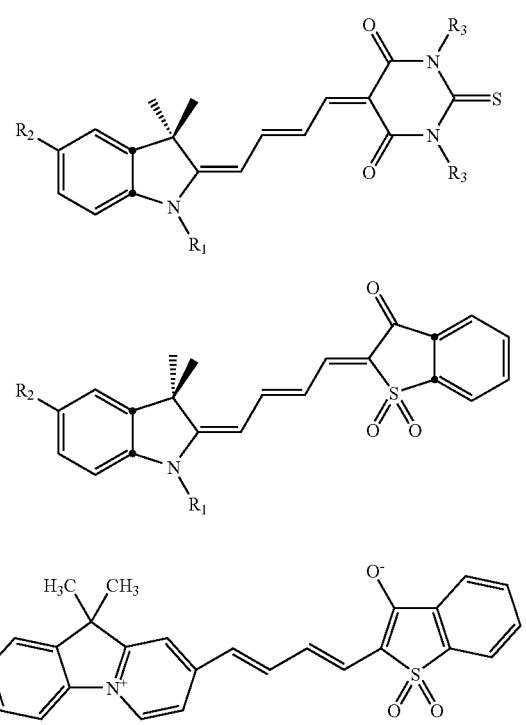

wherein:
R₁ is lower alkyl, —(CH₂)₃—SO₃—, —(CH₂)₃—NH-CO-CH₂—I or
—(CH₂)₃—N⁺(CH₃)₂—(CH₂)₂—NCS;
R₂ is H, —NH₂, —SO₃⁻, CH₃CONH—, ICH₂CONH—, HO(CH₂)₂—S—CH₂CONH—;
SuOCOCH₂OCH₂CON(CH₃)—or a protecting group; and
R₃ is lower alkyl or tolyl-acetonitrile.

29. The dye of claim 28, wherein the dye further comprises one or more linkers.

30. The dye of claim 28, wherein the dye is linked to a biosensor, a binding domain, a biomolecule's binding site, or a target molecule.

31. A kit comprising a dye and instructions for using the dye, wherein the dye is a dye of claim 28.

32. The kit of claim 31, wherein the kit instructions comprise instructions for attaching the dye to a selected binding domain.

33. A method of detecting an interaction between a selected endogenous target biomolecule and a cellular entity, the method comprising:
  a. identifying a cell comprising a selected endogenous target biomolecule;
  b. providing a probe biomolecule comprising a binding domain with specific binding affinity for a binding site on the target biomolecules and the environmentally sensitive dye of claim 28;
  c. incubating the probe biomolecule with the cell;
  d. observing a background signal from the environmentally sensitive dye; and
  e. detecting a signal change from the environmentally sensitive dye to thereby detect an interaction between the target biomolecule and a cellular entity.

34. The method of claim 33, wherein the cellular entity is selected from the group consisting of a cellular nucleic acid, protein, peptide, enzyme, receptor, cytokine, cytoskeleton and signal transduction protein.

35. The method of claim 33, wherein the binding domain of a probe biomolecule can bind the target biomolecule at a phosphorylation site.

36. The method of claim 33, wherein the binding domain has specific affinity for a particular conformation, ligand interaction, or posttranslational modification of the target biomolecule.

37. The method of claim 33, wherein the binding domain comprises SEQ ID NO:1, 2, 4, 5, 9, 10, 11, 16, 17, 18, 19, 20, 21, 22 or 27.

38. The method of claim 33, wherein the dye comprises an excitation or emission light wavelength of about 600 nm or more.

39. The method of claim 33, wherein the environmentally sensitive dye is linked to the binding domain at a site that does not substantially interfere with binding between the probe biomolecule and the target biomolecule.

40. The method of claim 39, wherein the site is selected by examination of a crystal structure for the binding domain or the target biomolecule.

41. The method of claim 33, wherein the probe biomolecule is fused to a TAT peptide.

42. The method of claim 33, wherein the method further comprises introducing the probe biomoleucle into the cell by using electroporation, transduction, microporation, microinjection, surfactants, or projectiles.

43. The method of claim 33, wherein the signal change comprises an at least 50% increase in fluorescence.

44. The method of claim 33, wherein detecting a signal change comprises fluorimetry, spectroscopy, enzymatic alteration of a substrate, microscopy, or mass spectroscopy.

45. The method of claim 33, wherein detecting a signal change comprises: quantifying protein amounts, locating a protein, detecting a conformational change in the target, detecting activation of the target, or detecting phosphorylation of the target.

46. A method of detecting changes in a target molecule of interest, the method comprising:
  (a) providing a target molecule with the environmentally sensitive dye of claim 28 attached to a site on the target molecule; and
  (b) detecting a change in signal from the dye upon exposure of the target molecule to new environment; wherein the hydrophobicity, hydrogen bonding, polarity, polarization, phosphorylation, polypeptide folding, hydration, ligand binding, or subunit interaction of the site on the target molecule changes upon exposure of the target molecule to the new environment.

47. A biosensor to detect Cdc42 activation, the biosensor comprising a Wiskott Aldrich syndrome protein (WASP) polypeptide chain and the dye of claim 28.

48. The biosensor of claim 47, wherein the WASP polypeptide chain comprises SEQ ID NO:27.

49. The biosensor of claim 47, wherein the dye is attached to the WASP polypeptide at a position corresponding to position 271 of SEQ ID NO:28.

50. A biosensor comprising:
  (a) a binding domain comprising SEQ ID NO: 12, where Phe-97 is Cys; and,
  (b) the environmentally sensitive dye of claim 28 linked to the binding domain.

51. A method of detecting a selected target molecule comprising contacting a test sample that may contain the selected target molecule with a biosensor and observing whether a signal is produced by the biosensor, wherein the biosensor comprises a binding domain and an environmentally sensitive dye of claim 28, and wherein the binding domain is a single chain variable fragment (scFv) of an antibody with an attachment site for a dye within a CDR3 region of the scFv.

52. The method of claim 51, wherein the attachment site for the dye is a cysteine.

53. The method of claim 51, wherein the biosensor binding domain comprises SEQ ID NO:1, SEQ ID NO:2 or SEQ ID NO:4.

54. The method of claim 51, wherein the selected target molecule is a protein, receptor, ligand, or enzyme.

55. The method of claim 51, wherein the test sample comprises a living cell, a cell lysate, a cell library, or a cell culture.

56. A biosensor comprising:
(a) a binding domain that is a ligand with specific affinity for a target molecule; and,
(b) an environmentally sensitive dye of the formula:

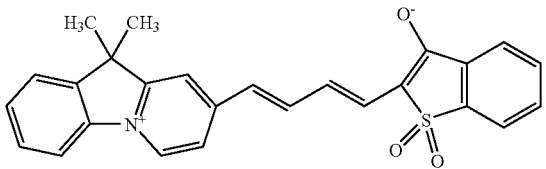

* * * * *

UNITED STATES PATENT AND TRADEMARK OFFICE
CERTIFICATE OF CORRECTION

| | | |
|---|---|---|
| PATENT NO. | : 7,592,188 B2 | Page 1 of 1 |
| APPLICATION NO. | : 11/079907 | |
| DATED | : September 22, 2009 | |
| INVENTOR(S) | : Hahn et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 140 days.

Signed and Sealed this

Fourteenth Day of December, 2010

David J. Kappos
*Director of the United States Patent and Trademark Office*